United States Patent
Longo

(10) Patent No.: US 8,211,700 B2
(45) Date of Patent: Jul. 3, 2012

(54) INDUCTION OF DIFFERENTIAL STRESS RESISTANCE AND USES THEREOF

(75) Inventor: Valter Longo, Playa del Rey, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 12/058,600

(22) Filed: Mar. 28, 2008

(65) Prior Publication Data

US 2008/0242638 A1 Oct. 2, 2008

Related U.S. Application Data

(60) Provisional application No. 60/908,636, filed on Mar. 28, 2007, provisional application No. 60/942,561, filed on Jun. 7, 2007.

(51) Int. Cl.
- *C12Q 1/00* (2006.01)
- *C12N 5/00* (2006.01)
- *C12N 5/02* (2006.01)
- *C12N 5/06* (2006.01)
- *C12N 5/08* (2006.01)
- *C12N 5/10* (2006.01)
- *G01N 33/48* (2006.01)

(52) U.S. Cl. ............ 435/384; 435/4; 435/325; 435/363; 435/366; 435/371; 435/383; 435/392; 436/63; 436/64

(58) Field of Classification Search ............... 435/4, 325, 435/363, 366, 371, 383, 384, 392; 436/63, 436/64
See application file for complete search history.

(56) References Cited

U.S. PATENT DOCUMENTS

| | | | |
|---|---|---|---|
| 4,724,234 A | 2/1988 | Cone, Jr. | |
| 5,292,723 A | 3/1994 | Audry et al. | |
| 6,338,856 B1 | 1/2002 | Allen et al. | |
| 2002/0035071 A1 | 3/2002 | Pitha et al. | |
| 2004/0005294 A1* | 1/2004 | Lee | 424/93.2 |
| 2004/0121407 A1 | 6/2004 | Distefano et al. | |
| 2005/0245462 A1* | 11/2005 | Tidmarsh | 514/23 |
| 2005/0266438 A1 | 12/2005 | Spindler et al. | |
| 2006/0025337 A1 | 2/2006 | Sinclair et al. | |
| 2006/0073514 A1* | 4/2006 | Dedera et al. | 435/7.1 |
| 2006/0233804 A1* | 10/2006 | Deshayes et al. | 424/145.1 |
| 2006/0275506 A1 | 12/2006 | Fisher et al. | |
| 2007/0009576 A1 | 1/2007 | Stillman | |

FOREIGN PATENT DOCUMENTS

| | | |
|---|---|---|
| EP | 0 232 652 A1 | 8/1987 |
| EP | 0 560 989 A1 | 9/1993 |
| GB | 2 029 220 A | 3/1980 |
| WO | 2008/123298 A1 | 12/2009 |

OTHER PUBLICATIONS

Raffaghello et al. Starvation-dependent differential stress resistance protects normal but not cancer cells against high-dose chemotherapy. PNAS 105(24): 8215-8220, Jun. 17, 2008.*
Barvick et al. Effects of combined chemotherapy on sarcoma 180, with special reference to food intake, body-weight changes, and survival time. Journal of the National Cancer Institute 15(1): 177-189, Aug. 1954.*
Rudolf Breuss. The Breuss Cancer Cure, Alive Books, Burnaby, BC, Canada, Jun. 1995.*
International Search Report for corresponding PCT application PCT/US08/58778 lists the references above.
Supplementary European Search Report dated Jan. 25, 2011 in corresponding EP Appn. No. 08733006.4-2107, filed Mar. 28, 2008, 10 pgs.
Supplementary European Search Report dated Aug. 31, 2011 in corresponding EP Appn. No. 09 73 4637, filed Nov. 19, 2010, 1 PG.
International search report for corresponding PCT application PCT/US09/41736 lists the references above.

* cited by examiner

*Primary Examiner* — Alana Harris Dent
(74) *Attorney, Agent, or Firm* — Brooks Kushman P.C.

(57) ABSTRACT

This invention relates to methods of inducing differential stress resistance in a subject with cancer by starving the subject for a short term, administering a cell growth inhibitor to the subject, or reducing the caloric or glucose intake by the subject. The induced differential stress resistance results in improved resistance to cytotoxicity in normal cells, which, in turn, reduces cytotoxic side-effects due to chemotherapy, as well as improved effectiveness of chemotherapeutic agents.

2 Claims, 20 Drawing Sheets

A

B

A

B

A

B

A

B

INDUCTION OF DIFFERENTIAL STRESS RESISTANCE AND USES THEREOF

RELATED APPLICATIONS

This application claims priority to U.S. Provisional Application Ser. No. 60/908,636, filed Mar. 28, 2007, and U.S. Provisional Application Ser. No. 60/942,561, filed Jun. 7, 2007, the contents of which are incorporated herein by reference in their entirety.

FUNDING

The present invention was made, at least in part, with the financial support of NIH/NIA grants AG20642 and AG025135. The government has certain rights in the invention.

FIELD OF THE INVENTION

The present invention, in general, relates to methods for treating cancer. In particular, the present invention provides methods for enhancing the effectiveness of chemotherapy by inducing differential stress resistance in normal cells and cancer cells via short-term starvation, cell growth inhibitors, or reduced caloric or glucose intake.

BACKGROUND OF THE INVENTION

Until recently, the treatment of cancer has been largely focused on the development of therapeutic agents or techniques that kill cancer cells. For example, most chemotherapeutic drugs work by impairing mitosis (cell division), effectively targeting fast-dividing cells. As these drugs cause damage to cells they are termed cytotoxic. Some drugs work by causing cells to undergo apoptosis (so-called "cell suicide"). Unfortunately, scientists have yet to be able to locate specific features of malignant and immune cells that would make them uniquely targetable (barring some recent examples, such as the Philadelphia chromosome as targeted by imatinib). This means that other fast dividing cells such as those responsible for hair growth and for replacement of the intestinal epithelium (lining) are also affected.

Because chemotherapy affects cell division, both normal and cancerous cells are susceptible to the cytotoxic effects of chemotherapeutic agents. Success of conventional chemotherapeutic regiment is based on the principle that tumors with high growth fractions (such as acute myelogenous leukemia and the lymphomas, including Hodgkin's disease) are more sensitive to chemotherapy because a larger proportion of the targeted cells are undergoing cell division at any given time. This strategy often results in undesirable side-effects such as hair loss and normal tissue/organ damage. It also has severe limitations on the dosage of chemotherapeutic agents that can be administered to a patient, thus, limiting the effective range of chemotherapy.

SUMMARY OF THE INVENTION

The present invention provides a novel approach to cancer therapy by providing a method to differentially enhance the resistance of normal cells to chemotherapeutic agents, thereby, improving the effectiveness of chemotherapeutic agents in killing cancerous cells. By making normal cells more resistant to chemotherapeutic agents, a patient's tolerance for cytotoxicity is improved, which, in turn, also improves the effectiveness of chemotherapy.

More specifically, in one aspect, the invention features methods of inducing differential stress resistance in a subject with cancer. One method comprises starving the subject for 24-60 (e.g., 48) hours and administering to the subject a chemotherapy agent. The method may further comprise administering to the subject a cell growth inhibitor.

Another method of the invention comprises administering a cell growth inhibitor to the subject and administering to the subject a chemotherapy agent. For example, by using a cell growth inhibitor, the serum concentration of IGF-I in the subject may be reduced by 75-90%.

Another method of the invention comprises reducing the caloric intake or the glucose intake by the subject and administering to the subject a chemotherapy agent. For example, the caloric intake may be reduced by 10-100%, and the blood glucose concentration in the subject may be reduced by 20-50%.

In another aspect, the invention features methods of contacting a cancer cell with a chemotherapy agent and methods of increasing resistance of a non-cancer cell to a chemotherapy agent. One method comprises starving the cell for 24-60 (e.g., 48) hours and contacting the cell with a chemotherapy agent. The method may further comprise contacting the cell with a cell growth inhibitor.

Another method of the invention comprises contacting the cell with a cell growth inhibitor and contacting the cell with a chemotherapy agent.

Another method of the invention comprises cultivating the cell in a medium with reduced serum, IGF-I, or glucose concentration and contacting the cancer cell with a chemotherapy agent. For example, the serum concentration in the medium may be reduced by 10-90%, the IGF-I concentration in the medium may be reduced by 10-100%, and the glucose concentration in the medium may be reduced by 20-50%.

A chemotherapy agent may be a DNA alkylating agent, oxidant, or topoisomerase inhibitor. Examples of chemotherapy agents include, but are not limited to, methyl methanesulfonate, cyclophosphamide, etoposide, doxorubicin, and menadione. Examples of cancer include, but are not limited to, glioma, neuroblastoma, pheochromocytoma, and prostate cancer.

A cell growth inhibitor inhibits, e.g., IGF-I, IGF-IR, GH, Akt, Ras, Tor, or Erk. Examples of cell growth inhibitors include, but are not limited to, IGFBPs, IGF-R blocking antibodies, and small molecule inhibitors such as octreotide.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

Figure 2:
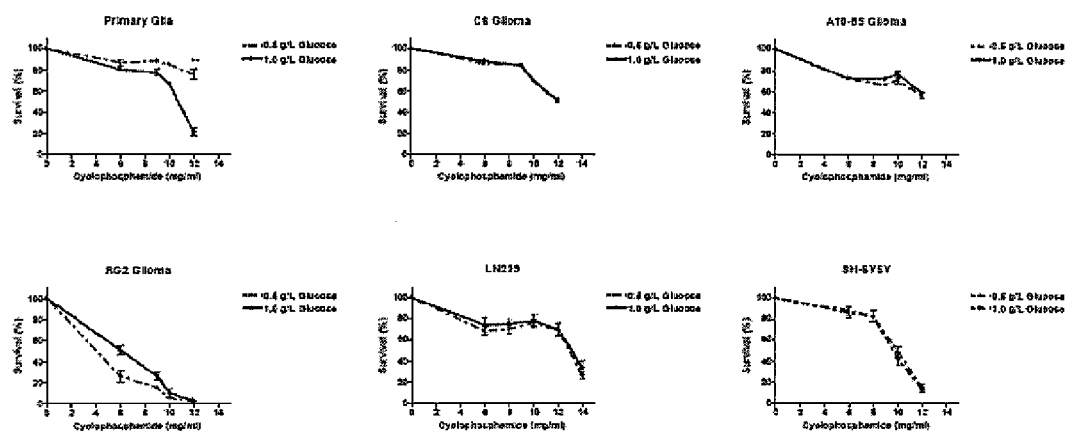
Figure 2:
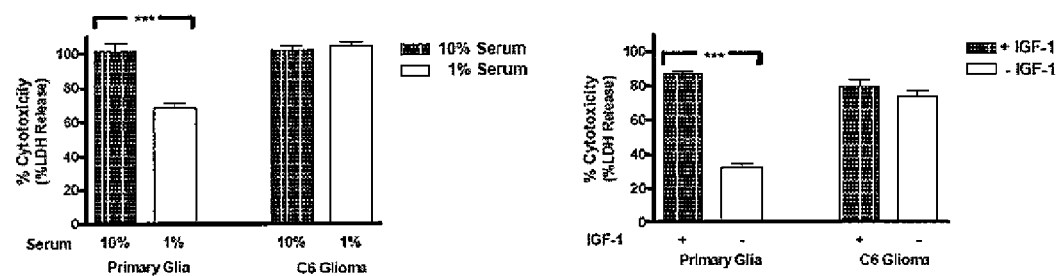
Figure 2:
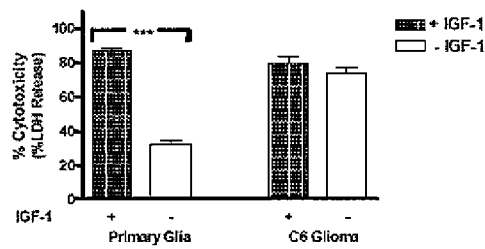
Figure 2:
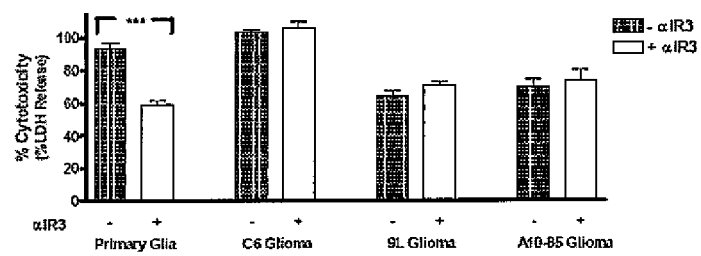

FIG. 2. DSR against a chemotherapeutic drug (CP) in primary rat mixed glial cells and rat glioma cell lines. A) Glucose restriction induced DSR. Cells were incubated in either low glucose (0.5 g/L) (STS) or normal glucose (1.0 g/L), supplemented with 1% serum for 24 hours. Viability was determined by the ability to reduce MTT following CP treatment (dose response range: 6-12 mg/ml) (n=9). B) Serum restriction induced DSR. Cells were incubated in medium with either 1% (STS) or 10% FBS for 24 hours. Cytotoxicity was determined by measuring the relative level of LDH released following CP treatment (15 mg/ml) (n=12). C) Lack of IGF-I induced DSR. Cells were incubated in medium with 1% serum and rhIGF-I (100 ng/ml) for 48 hours. Cytotoxicity was determined by measuring the relative level of LDH released following CP treatment (12 mg/ml) (n=21). D) aIR3 induced DSR. Cells were incubated in DMEM/F12 with 1% serum and neutralizing anti-IGF-IR monoclonal antibody aIR3 (1 μg/ml) for 24 hours. Cytotoxicity was determined by measuring the relative level of LDH released following CP treatment (15 mg/ml) (n=12). All data presented as mean ±SD. P-values were calculated by the Student's t-test (* p<0.05, ** p<0.01).

Figure 3:
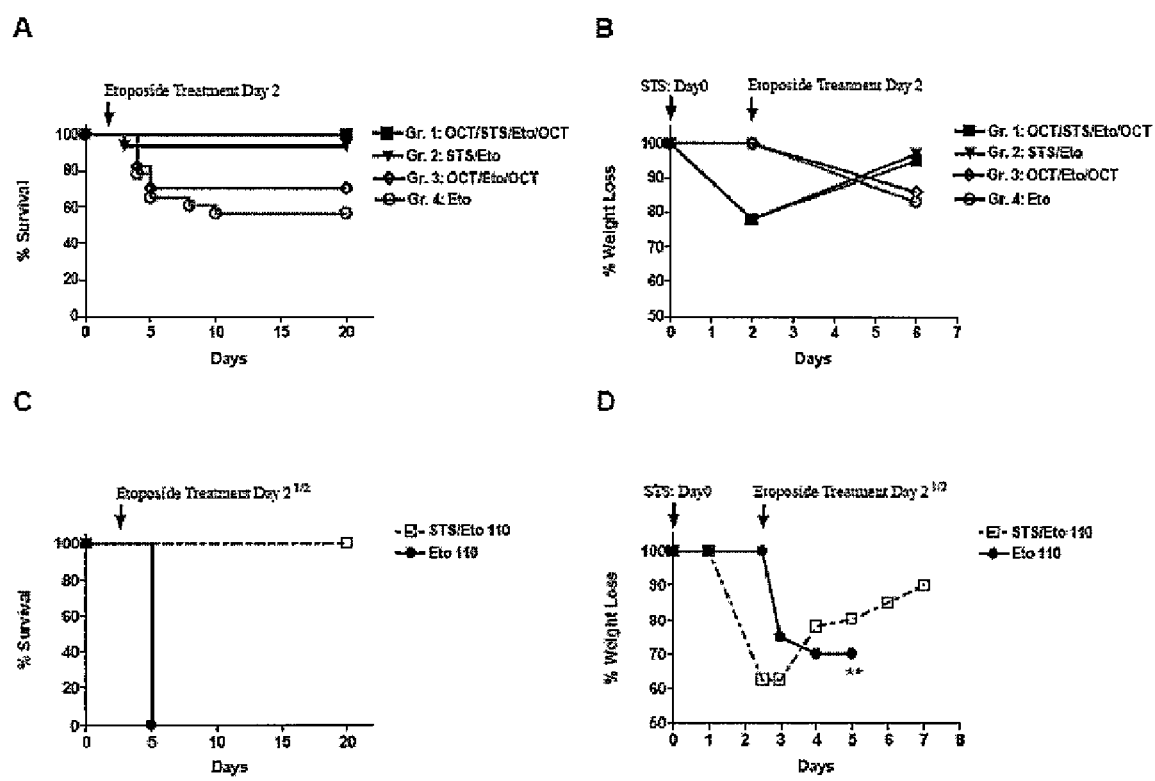

FIG. 3. A) Differential stress resistance in A/J mice after STS and octreotide treatment. All mice received an i.v. injection of 80 mg/Kg etoposide (Eto) on day 7. The different groups were treated as follows: Gr. 1 (35 mice): pre-treatment with a 1 mg/Kg/day octreotide (OCT) for 4 days+48-hour STS (day 4-6)+treatment with 80 mg/Kg Eto on day 7+post-treatment with 1 mg/Kg/day octreotide (OCT) on days 8-11. Gr. 2 (16 mice): 48-hour STS on days 4-6+treatment with 80 mg/Kg Eto on day 7. Gr. 3 (17 mice): pre-treatment with 1 mg/Kg/day octreotide (OCT) for 4 days+treatment with 80 mg/Kg Eto on day 7+post-treatment with 1 mg/Kg/day octreotide (OCT) on days 8-11. Gr. 4 (23 mice): treatment with 80 mg/Kg Eto on day 7. B) Percentage weight loss (a measure of toxicity) after STS and etoposide treatment. C) Differential stress resistance in CD1 mice after STS. All mice (5 mice/group) received an i.v. injection of 110 mg/Kg etoposide (Eto), after a 60-hour starvation. The toxicity, evaluated by percentage of survival, is shown. P values were calculated by Peto's log rank test: (P<0.0001). D) Percentage weight loss (a measure of toxicity) after STS and etoposide treatment. ** day at which all mice died of toxicity.

Figure 4:
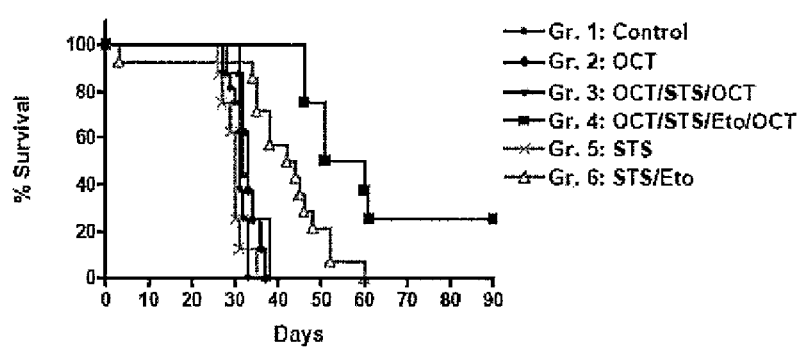
Figure 4:
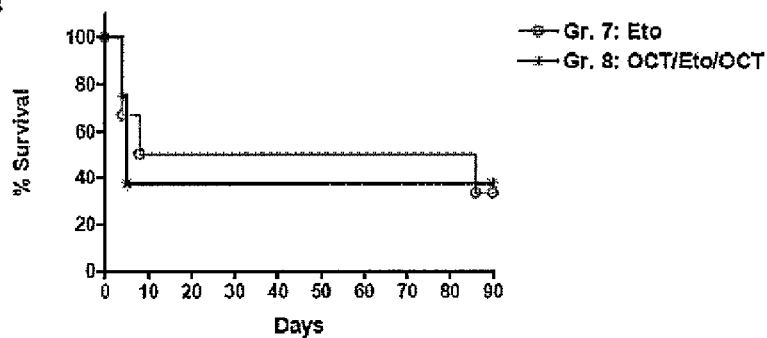

FIG. 4. Survival of neuroblastoma (NXS2)-bearing mice after chemotherapy treatment. All mice were inoculated i.v. with 200,000 NXS2 cells/mouse on day 4. The different groups were treated as follows: A) Gr. 1: Control (8 mice)=i.v. inoculation with NSX2 tumor cells on day 4. Gr. 2: OCT (8 mice)=pre-treatment with 1 mg/Kg/day octreotide (OCT) for 4 days before and after tumor inoculum. Gr. 3: OCT/STS/OCT (8 mice)=pre-treatment with 1 mg/Kg/day OCT before tumor cell inoculum+48-hour STS on days 4-6+post-treatment with 1 mg/Kg/day OCT on days 8-11. Gr. 4: OCT/STS/Eto/OCT (8 mice)=pre-treatment with 1 mg/Kg/day OCT for 4 days before tumor cell inoculum+48-hour STS on day 4-6+i.v. injection of 80 mg/Kg etoposide (Eto) on day 7+post-treatment with 1 mg/Kg/day OCT on days 8-11. Gr. 5: STS (8 mice)=48-hour STS on days 4-6. Gr. 6: STS/Eto (7 mice)=48-hour STS on days 4-6+i.v. injection of 80 mg/Kg etoposide (Eto) on day 7. B) Gr. 7: Eto (6 mice)=i.v. injection of 80 mg/Kg etoposide (Eto) on day 7. Gr. 8: OCT/Eto/OCT=pre-treatment with 1 mg/Kg/day OCT for 4 days before tumor cell inoculum+i.v. injection of 80 mg/Kg etoposide (Eto) on day 7+post-treatment with 1 mg/Kg/day OCT on days 8-11. Statistics: P Gr. 4 vs Gr. 1<0.0001, P Gr. 4 vs Gr. 3<0.0001, P Gr. 6 vs Gr. 1=0.14, P Gr. 8 vs Gr. 1=0.38, P Gr. 7 vs Gr. 1=0.99, P Gr. 4 vs Gr. 6=0.01, P Gr. 8 vs Gr. 5=0.66. Survival of mice was monitored daily. P values were calculated by Peto's log rank test.

Figure 5:
Figure 5:

FIG. 5. A) OCT/STS/OCT treated mice and B) control mice shown after etoposide treatment.

Figure 6:
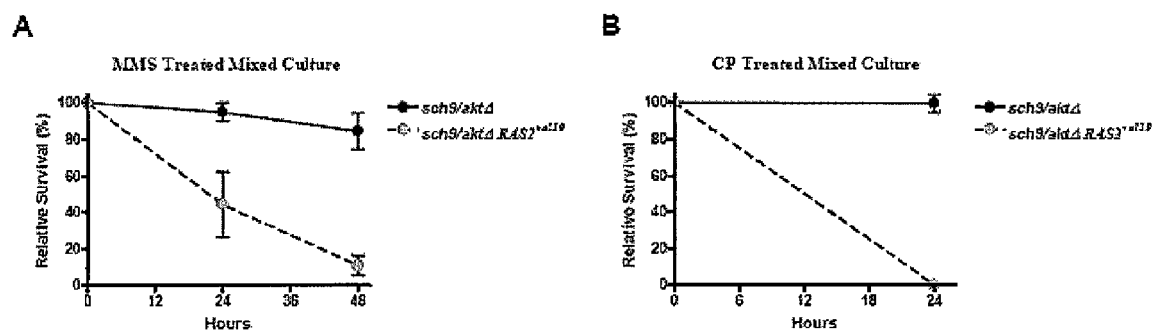

FIG. 6. A, B) Differential stress resistance (DSR) against chronic cyclophosphamide and methyl methanesulfonate treatments in mixed yeast cultures. sch9/aktΔ and sch9/aktΔ RAS2$^{val19}$ cells were inoculated in SDC medium at OD=0.1 and incubated at 30° C. with shaking. 24 hours later (OD~10), sch9/aktΔ and sch9/aktΔ RAS2$^{val19}$ were mixed and incubated for 2 hours at 30° C. with shaking. The initial sch9/akt:sch9/aktΔ RAS2$^{val19}$ ratio, measured by growth on selective media, was 25:1. Mixed cultures were then treated with either CP (0.1 M) or MMS (0.01%). Viability was measured every 24 hours by plating onto appropriate selective media that allows the distinction of the 2 strains. Data from 3 independent experiments are shown as mean ±SD.

Figure 7:
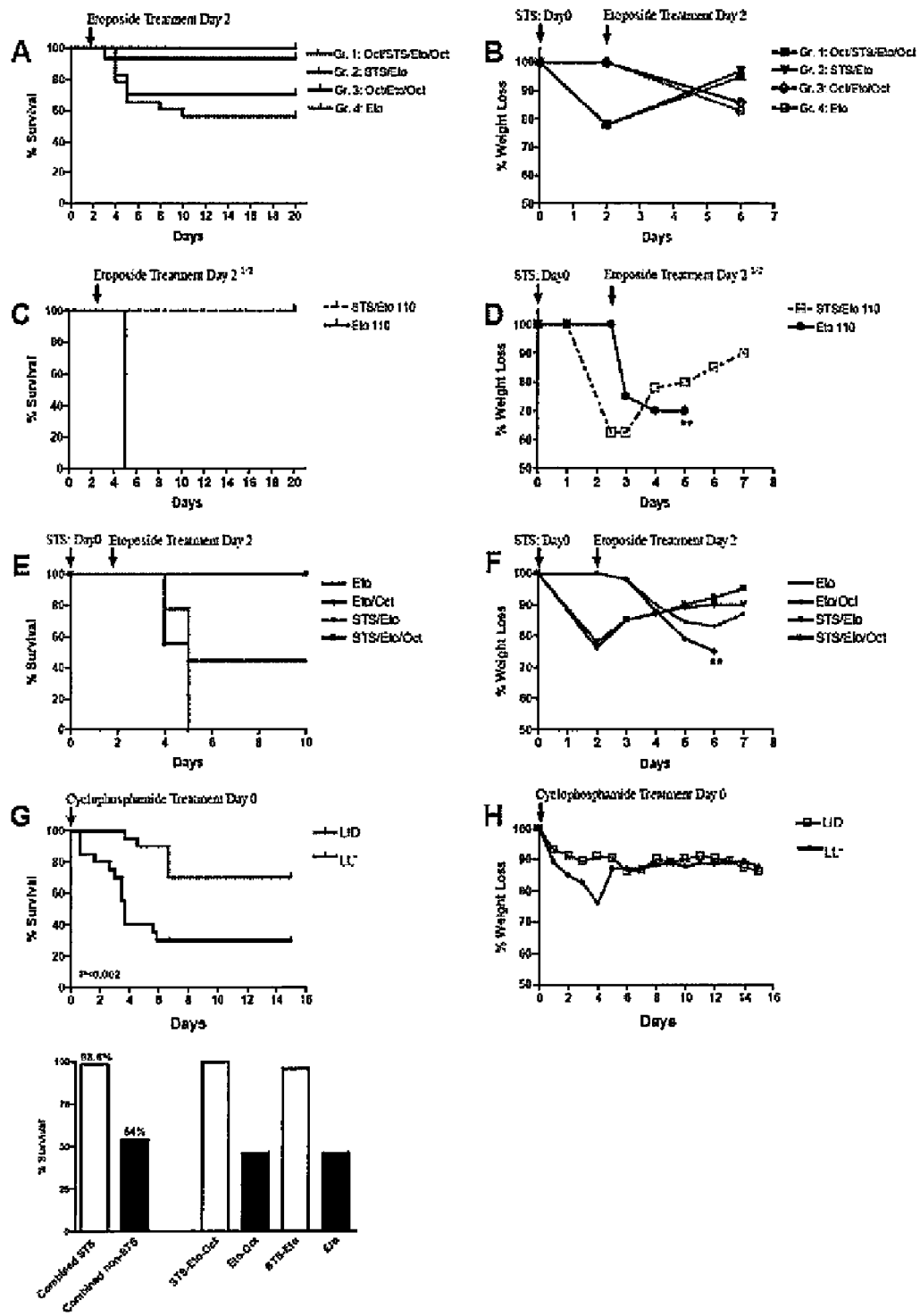

FIG. 7. A) Resistance to high-dose chemotherapy in A/J mice after STS and/or octreotide treatment. Mice were treated as follows: Gr. 1 (35 mice): pre-treatment with 1 mg/kg/day octreotide for 4 days+48-hour STS (day 4-6)+treatment with 80 mg/kg Eto on day 7+post-treatment with 1 mg/kg/day octreotide on days 8-11. Gr. 2 (16 mice): 48-hour STS on days 4-6+treatment with 80 mg/kg Eto on day 7. Gr. 3 (17 mice): pre-treatment with 1 mg/kg/day octreotide for 4 days+treatment with 80 mg/kg Eto on day 7+post-treatment with 1 mg/kg/day octreotide on days 8-11. Gr. 4 (23 mice): treatment with 80 mg/kg Eto on day 7. B) Percent weight loss of A/J mice (a measure of toxicity) after STS and Eto treatment. C) Resistance to high-dose chemotherapy in CD1 mice after STS. All mice (5 mice/group) received an i.v. injection of 110 mg/kg etoposide (Eto), after a 60-hour starvation. The toxicity, evaluated by percent survival, is shown. P values were calculated by Pete's log rank test: (P<0.0001). D) Percent weight loss of CD1 mice (a measure of toxicity) after STS and Eto treatment. ** day at which all mice died of toxicity. E) Resistance to high-dose chemotherapy in athymic (Nude-nu) mice after STS. All mice received an i.v. injection of 100 mg/kg Eto, after a 48-hour starvation. The toxicity, evaluated by percent survival, is shown. F) Percent weight loss (a measure of toxicity) of athymic (Nude-nu) after STS and etoposide treatment. G) Resistance to high-dose chemotherapy in LID mice. All mice received an i.p. injection of 500 mg/kg Cyclophosphomide and were single caged throughout the experiment. The toxicity, evaluated by percent survival, is shown p<0.002). H) Percent weight loss (a measure of toxicity) of LID mice after Cyclophosphamide treatment. I) Survival fraction of STS treated and untreated mice after etoposide injection. Mice from 3 different genetic backgrounds (A/J, CD1 and Nude) were injected with etoposide with or without STS pre-treatment. All treatments with STS have been combined and compared with all treatments without STS and shown as percent survival after etoposide injection. Also, the percent survival of each treatment after etoposide injection is compared and shown.

Figure 8:
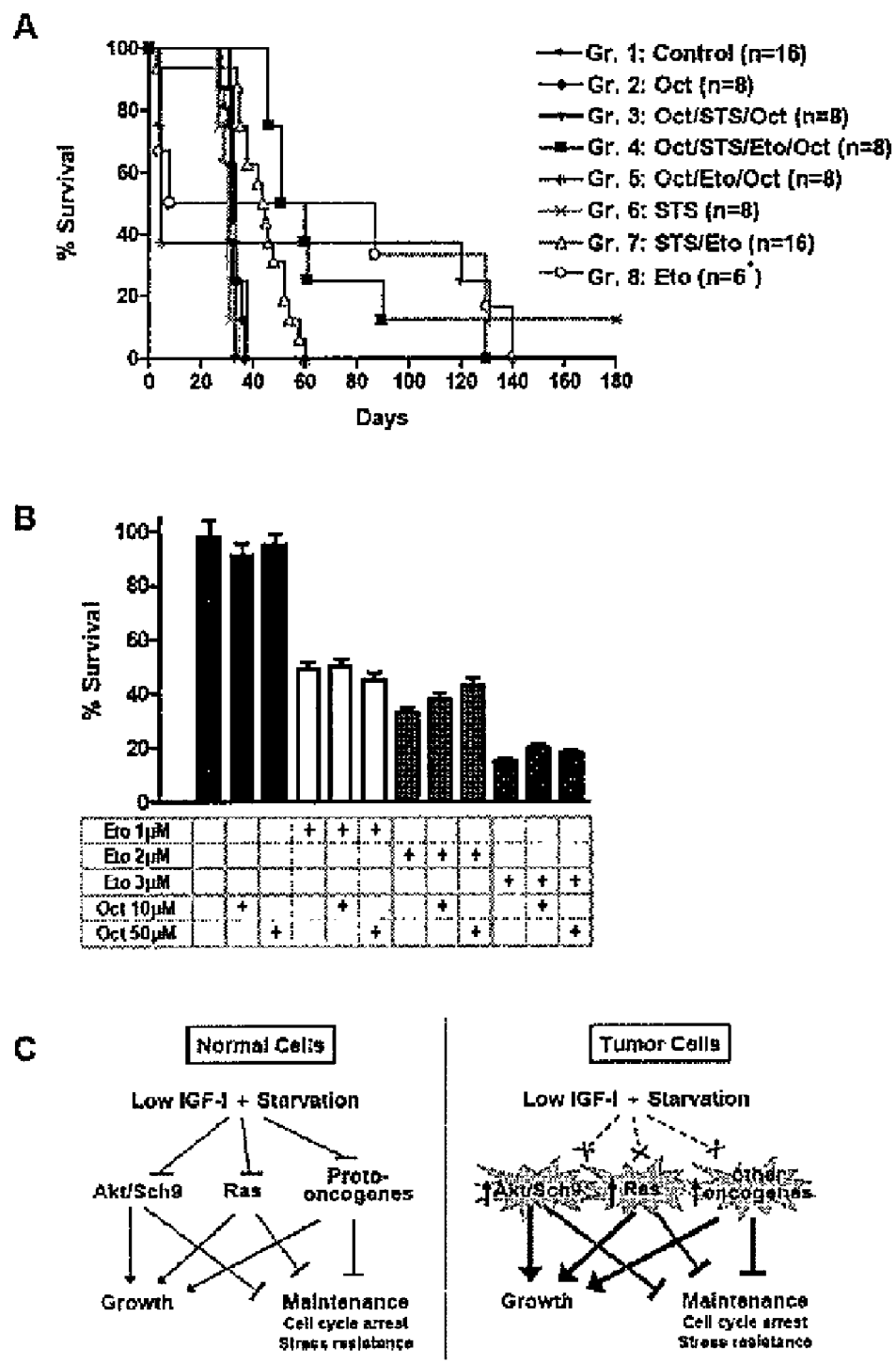

FIG. 8. Survival of neuroblastoma (NXS2)-bearing mice. All mice were inoculated i.v. with 200,000 NXS2 cells/mouse on day 4. The different groups were treated as follows: A) Gr. 1: Control (16 mice)=i.v. inoculation with NSX2 tumor cells on day 4. Gr. 2: Oct (8 mice)=pre-treatment with 1 mg/kg/day octreotide for 4 days before and after tumor injection on day 4. Gr. 3: Oct/STS/Oct (8 mice)=pre-treatment with 1 mg/kg/day Oct before tumor cell injection on day 4+48-hour STS on days 4-6+post-treatment with 1 mg/kg/day Oct on days 8-11. Gr. 4: Oct/STS/Eto/Oct (8 mice)=pre-treatment with 1 mg/kg/day Oct for 4 days before tumor cell injection+48-hour STS on day 4-6+i.v. injection of 80 mg/kg etoposide (Eto) on day 7+post-treatment with 1 mg/kg/day Oct on days 8-11. Gr. 5: Oct/Eto/Oct (8 mice)=pre-treatment with 1 mg/kg/day Oct for 4 days before tumor cell injection+i.v. injection of 80 mg/Kg etoposide (Eto) on day 7+post-treatment with 1 mg/kg/day Oct on days 8-11. Gr. 6: STS (8 mice)=i.v. inoculation with NSX2 tumor cells on day 4+48-hour STS on days 4-6. Gr. 7: STS/Eto (16 mice)=i.v. inoculation with NSX2 tumor cells on day 4+48-hour STS on days 4-6+i.v. injection of 80 mg/kg etoposide (Eto) on day 7. Gr. 8: Eto (6 mice, *2 deaths caused by the injection procedure)=i.v. inoculation with NSX2 tumor cells on day 4+i.v. injection of 80 mg/kg etoposide (Eto) on day 7. B) Effect of octreotide on etoposide cytotoxicity in NXS2 neuroblastoma cells. NXS2 cells treated with different concentrations of etoposide (1-3 microM) in the presence or absence of octreotide (10 and 50 microM) for 72 hours were harvested by scraping, washed with complete medium, and incubated with trypan blue for 1 minute at 37° C. Viability was determined by counting the cells with a contrast phase microscope. The proportion of dead (or living) cells was calculated by dividing the number of dead (or living) cells by the total number of cells per field. C) The DSR model: oncogenes prevent cells from entering into a protective maintenance mode in response to starvation and low IGF-1 signaling. One of the hallmarks of cancer cells is the ability to grow or remain in a growth mode regardless of external regulatory signals including IGF-1R, Ras, Akt and mTor.

Figure 9:
Figure 9:

FIG. 9. A) Oct/STS/Eto/Oct group and B) control group shown after Eto treatment (day 7).

Figure 10:
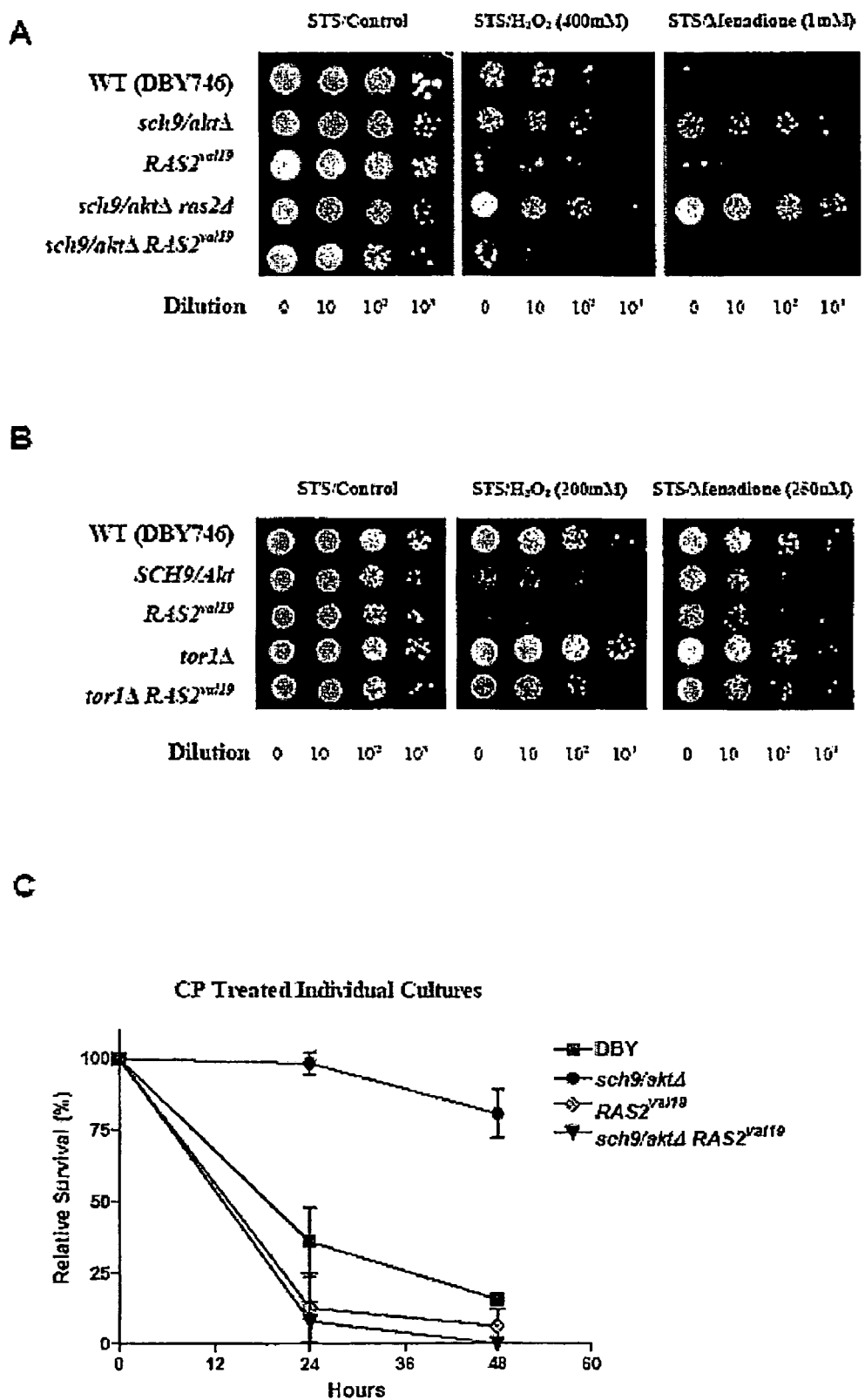

FIG. 10. A, B) Survival of STS-treated yeast cells deficient in Sch9 and/or Ras2 (sch9Δ, and sch9Δras2Δ), and cells overexpressing Sch9 or expressing constitutively active RAS2$^{val19}$ (SCH9, RAS2$^{val19}$, sch9ΔRAS2$^{val19}$, and tor1ΔRAS2$^{val19}$) after treatment with $H_2O_2$ or menadione. 24 hours after the initial inoculation (OD=0.1) in SDC medium, cultures were washed, resuspended and incubated in water for 48 hours with shaking. At day 3, cells were treated with either $H_2O_2$ for 30 min, or menadione for 60 min. Serial dilutions (up to 1,000-fold) of the treated cultures were spotted onto YPD plates and incubated for 2-3 days at 30° C. This experiment was repeated at least 3 times with similar results. A representative experiment is shown. C) DSR against chronic CP treatment. Wild type (DBY746), RAS2$^{val19}$, sch9Δ and sch9ΔRAS2$^{val19}$ strains were inoculated at OD=0.1, grown separately in glucose media, and treated with CP (0.1 M) 24 hours after initial inoculation. Viability was measured as colony forming units (CFU) at 24 and 48 hours.

Figure 11:
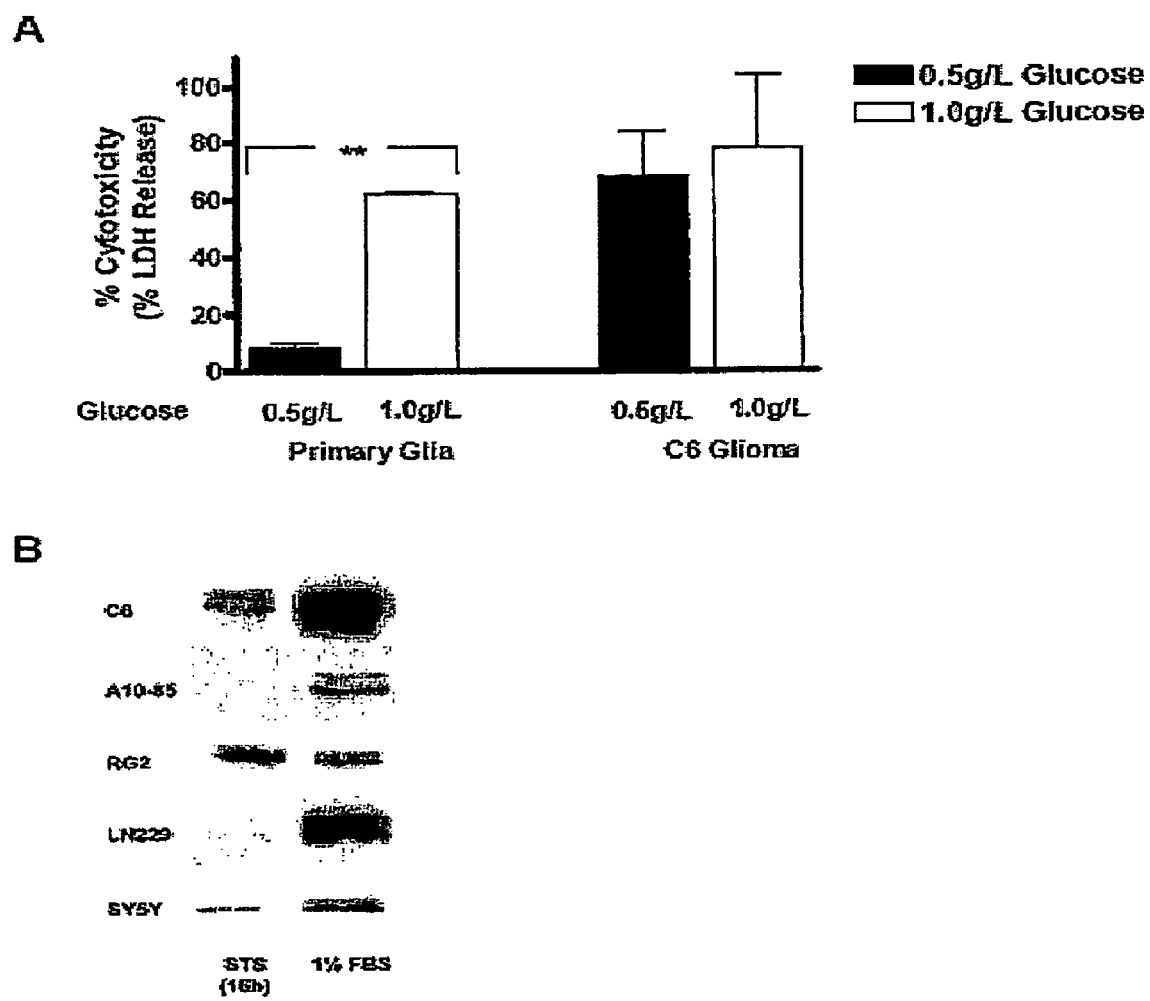

FIG. 11. A) In vitro STS effect on differential stress response (DSR) to cyclophosphamide treatments. Primary rat glial cells and the C6 rat glioma cells were grown to 70% confluency and then incubated in either low glucose (0.5 g/L) (STS) or normal glucose (1.0 g/L), supplemented with 1% serum for 24 hours followed by cyclophosphamide (12 mg/ml) treatment. Cytotoxicity was measured by LDH release. Data represented as mean ±SD. p-values were calculated using Student's t-test (** p<0.005). B) Phosphorylation of Erk1/2 in response to starvation conditions in 5 cancer cell lines. Rat glioma and human neuroblastoma cell lines (FIG. 11A) were starved by preincubation in glucose- and serum-free media for 17 hours (STS), or were kept in glucose- and serum-free media for 16 hours followed by a 1 hour treatment with serum (1% FBS). Western blots show Erk1/2 phosphorylation.

Figure 12:
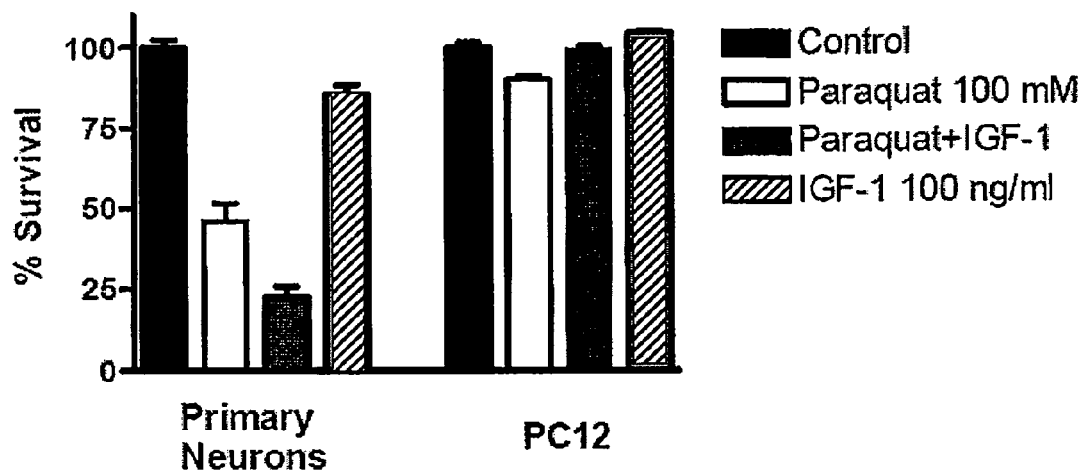

FIG. 12. 24 hr treatment with IGF-I sensitizes cortical neurons but not in PC12 cells to oxidative toxicity. Primary rat cortical neurons or PC12 cells incubated in 1% serum and 4 g/L glucose were treated for 24 hr with vehicle, 100 μM of paraquat, 100 ng/ml of IGF-I followed by 100 μM of paraquat, or 100 ng/ml of IGF-1 alone and were then subjected to MTT reduction activity assay to assess cell viability. Data from 4 independent experiments are normalized to control and expressed as the mean ±S.E.M.

Figure 13:
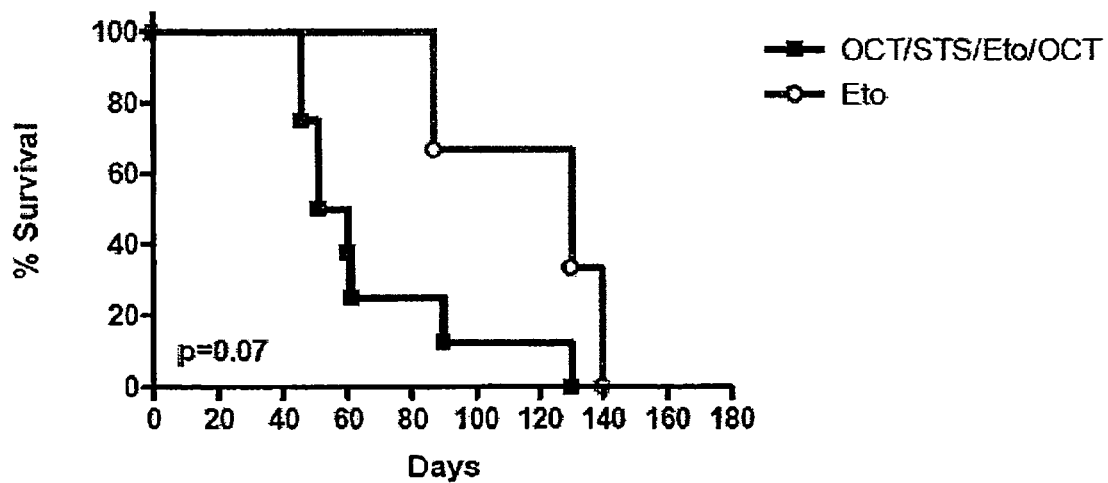

FIG. 13. Comparison of the long-term survival of mice from the Eto group that survived the initial toxicity and mice from the Oct/STS/Eto/Oct group. Statistical evaluation was done using Kaplan-Meier curves and log-rank test.

Figure 14:
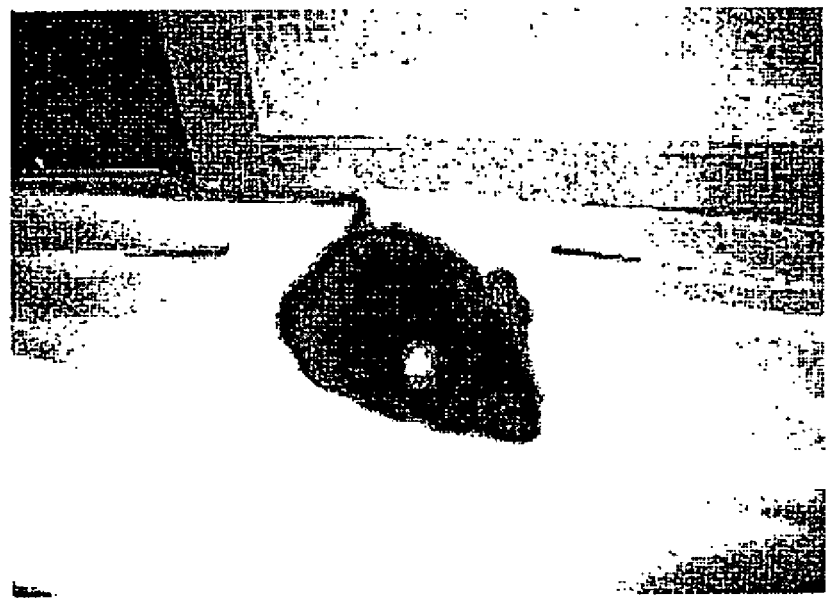
Figure 14:
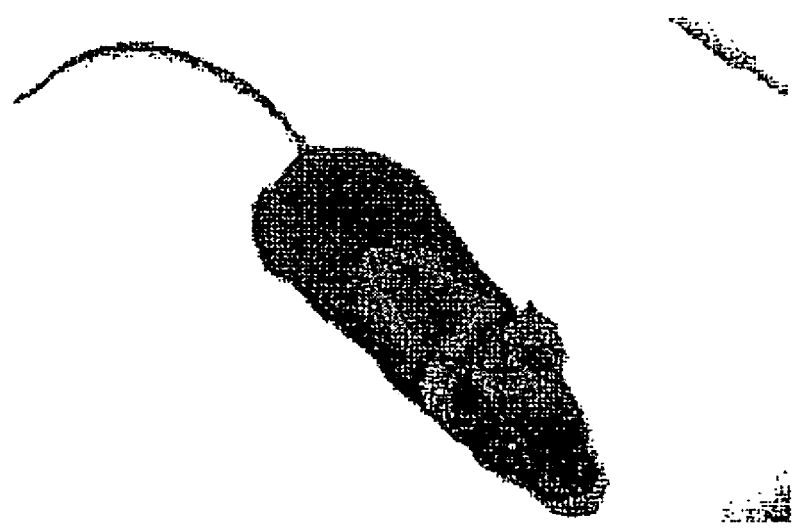

FIG. 14. A mouse from the (A) control group and (B) liver-IGF-1 deleted (LID) group shown after cyclophosphamide treatment.

Figure 15:
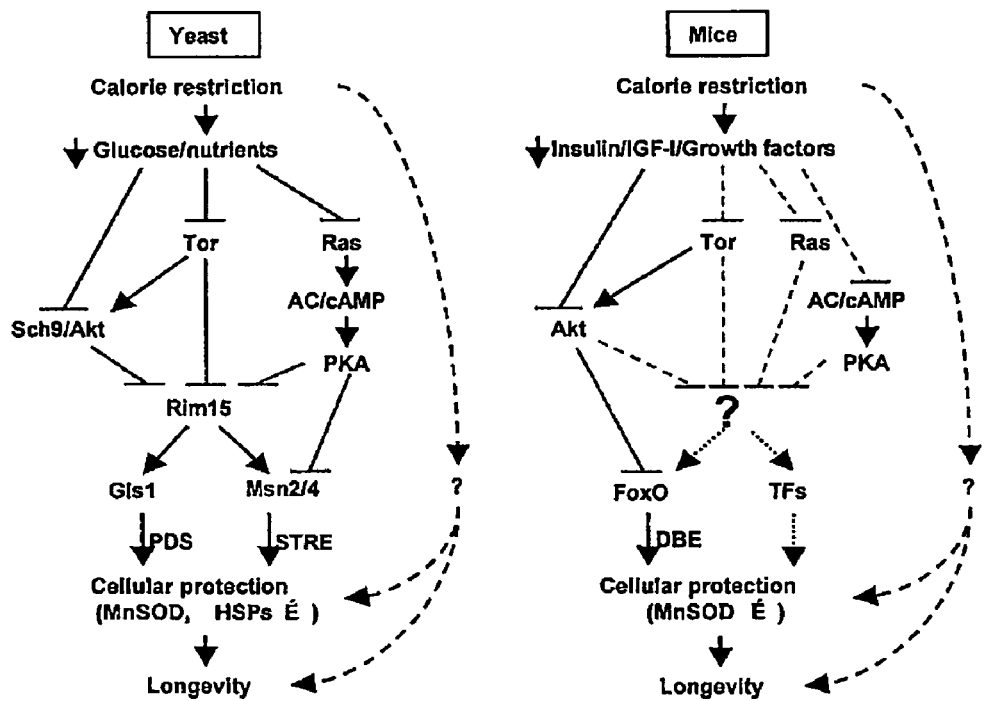

FIG. 15. Similar pathways regulate longevity and resistance to stress in yeast and mice.

Figure 16:
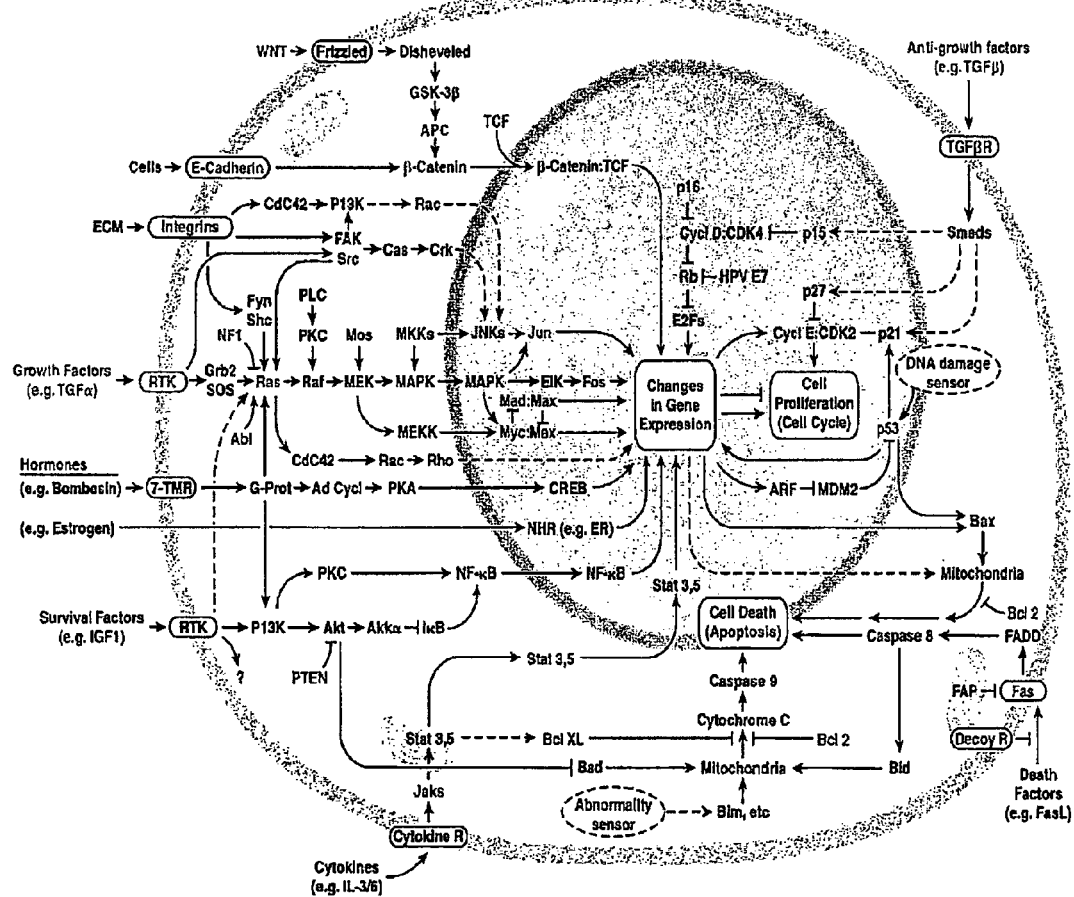

FIG. 16. The IGF-I, Ras and Akt pathways, whose downregulation regulate resistance to damage and aging in different model systems (FIG. 15), play central roles in mitosis and cancer.

Figure 17:
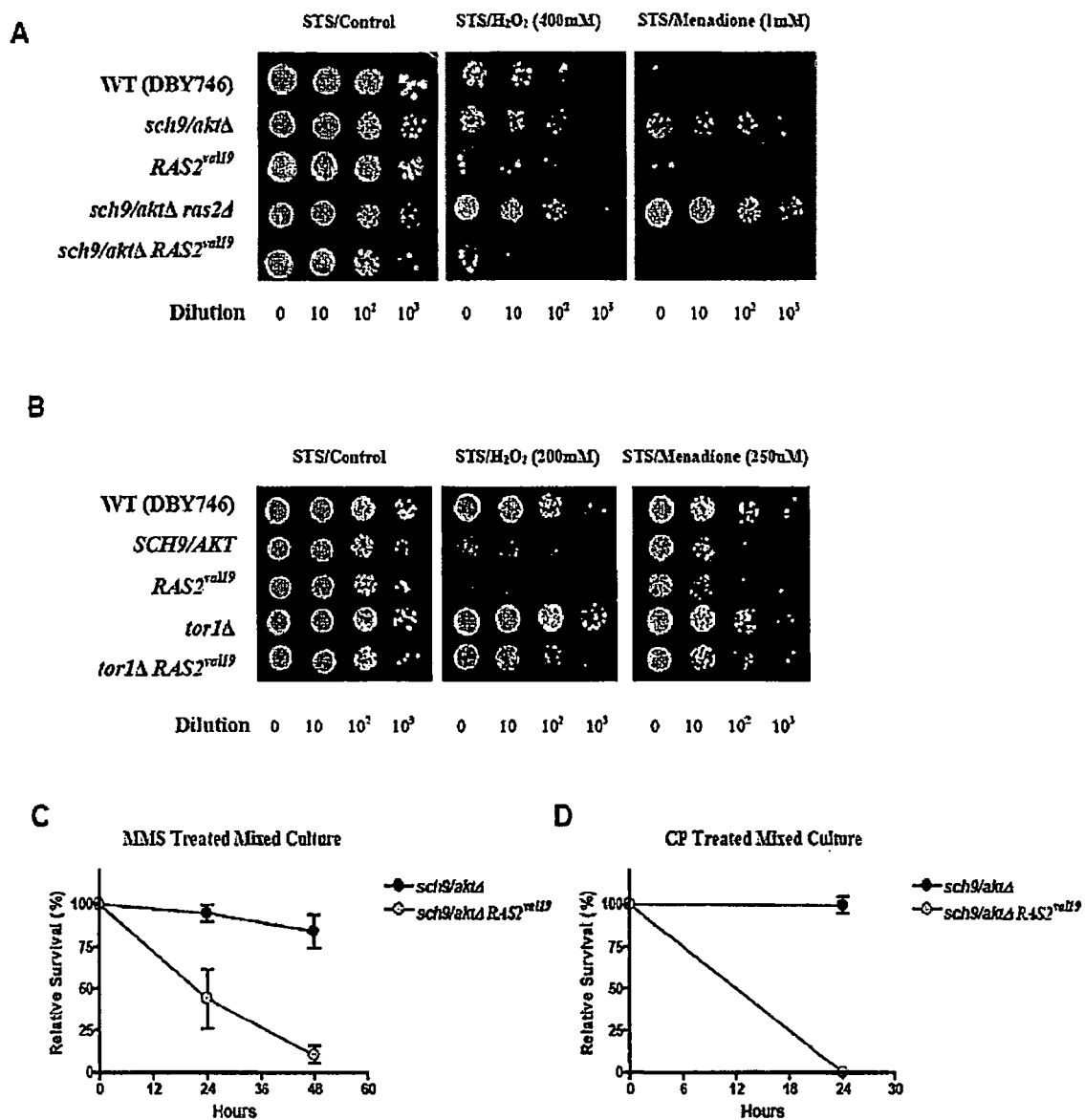

FIG. 17. A, B) Survival of STS-treated yeast cells deficient in Sch9/Akt and/or Ras2 (sch9/aktΔ, and sch9/aktΔ ras2Δ), and cells overexpressing Sch9/Akt or expressing constitutive active RAS2$^{val19}$ (Sch9/Akt, RAS2$^{val19}$, sch9/aktΔ RAS2$^{val19}$, and tor1Δ RAS2$^{val19}$) after treatment with $H_2O_2$ or menadione. 24 hours after the initial inoculation (OD=0.1) in SDC medium, cultures were washed, resuspended and incubated in water for 48 hours with shaking. At day 3, cells were treated with either $H_2O_2$ for 30 min, or menadione for 60 mm. Serial dilution (up to 1,000-fold) of the treated cultures were spotted onto YPD plates and incubated for 2-3 days at 30° C. This experiment was repeated at least 3 times with similar results. A representative experiment is shown. C) Differential stress resistance (DSR) against chronic cyclophosphamide and methyl methanesulfonate (MMS) treatments in mixed yeast cultures. sch9/aktΔ and sch9/aktΔ RAS2$^{val19}$ cells were inoculated in SDC medium at OD=0.1 and incubated at 30° C. with shaking. 24 hours later (OD~10), sch9/aktΔ and sch9/aktΔ RAS2$^{val19}$ were mixed and incubated for 2 hours at 30° C. with shaking. The initial sch9/aktΔ:sch9/aktΔ RAS2$^{val19}$ ratio, measured by growth on selective media, was 25:1. Mixed cultures were then treated with either CP (0.1 M) or MMS (0.01%). Viability was measured every 24 hours by plating onto appropriate selective media that allows the distinction of the 2 strains. Data from 3 independent experiments are shown as mean ±SD. D) DSR against chronic CP treatment. Wild type (DBY746), RAS2$^{val19}$, sch9/aktΔ and sch9/aktΔRAS2$^{val19}$ strains were inoculated at OD=0.1, grown separately in glucose media, and treated with CP (0.1 M) 24 hours after initial inoculation. Viability was measured as colony forming units (CFU) at 24 and 48 hours.

Figure 18:
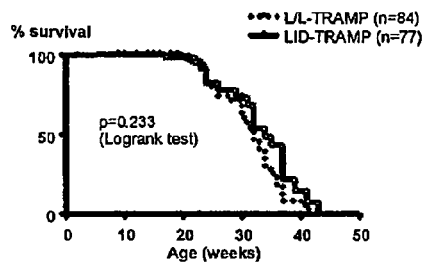

FIG. 18. Rates of survival and metastases in the LID-TRAMP model. Mice were analyzed at the time of death. Survival curves for the two strains are shown. There was no significant difference in the survival rate between male LID-TRAMP and L/L-TRAMP mice. The hazard ratio of male LID-TRAMP mice to male L/L-TRAMP mice was 0.736. There was no difference in rate of metastasis; however, IGF-I levels were 10% of TRAMP in the LID-TRAMP model.

Figure 19:
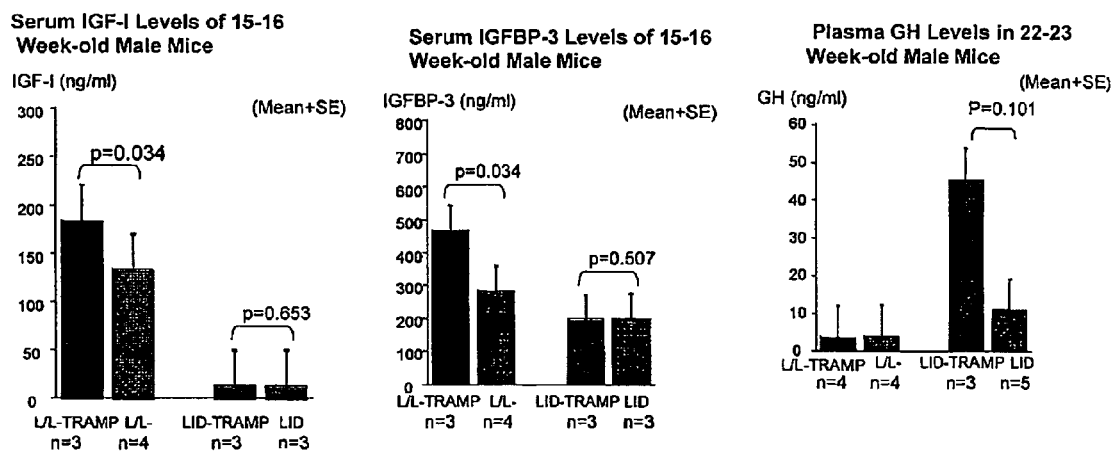

FIG. 19. Levels of GH-IGF axis analytes in the LID TRAMP cohort. Shown are the endogenous elevations of IGF-I and IGFBP-3 in the TRAMP model and the dramatic reductions in IGF-I in the LID model.

Figure 20:
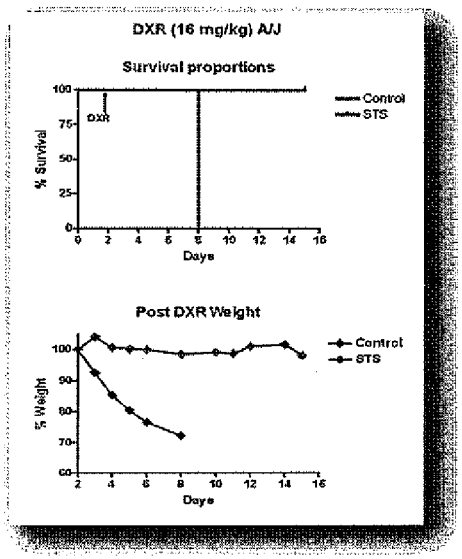

FIG. 20. A/J mice, weighing 18-20 g, were starved for 48 hours (STS), and followed by a single intravenous injection of high dose doxorubicin (16 mg/kg). The toxicity, evaluated by (A) percent survival and (B) daily weight measurements, are shown.

Figure 21:
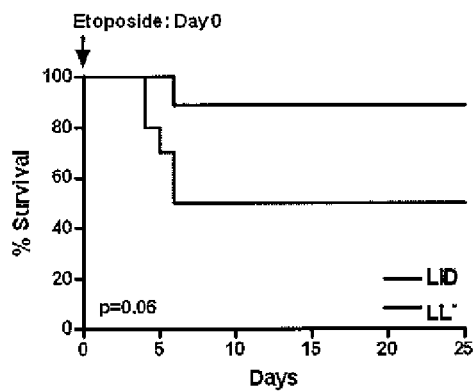
Figure 21:
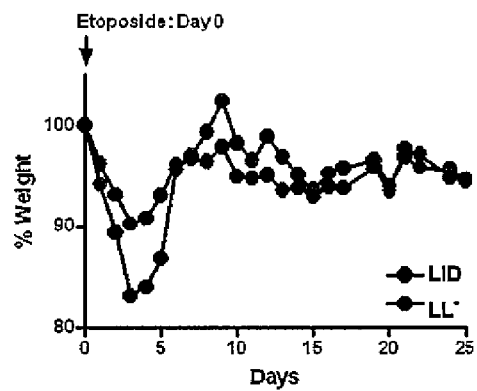

FIG. 21. Resistance to high-dose chemotherapy in LID mice. All mice received an i.v. injection of 100 mg/kg etoposide and were single caged throughout the experiment. The toxicity, evaluated by (A) percent survival and (B) daily weight measurements, are shown. p-value was calculated by log rank test (p=0.06, n=10).

Figure 22:
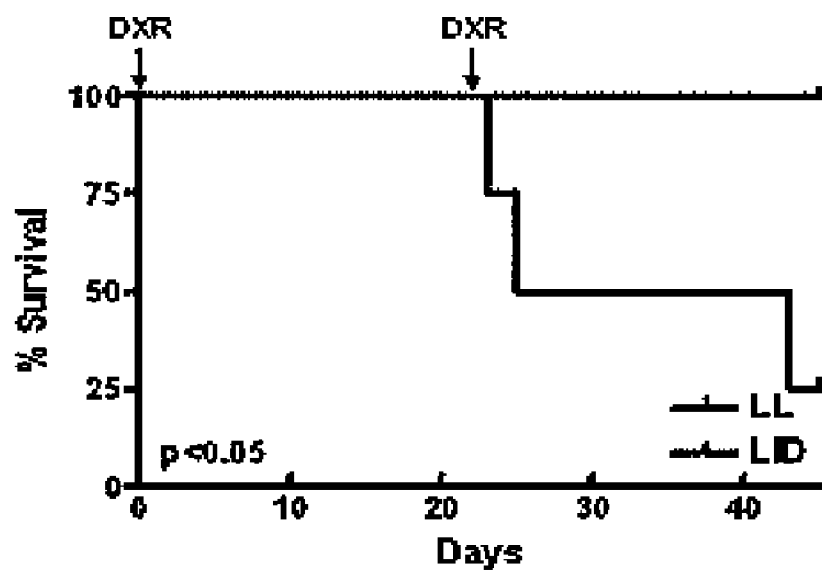
Figure 22:
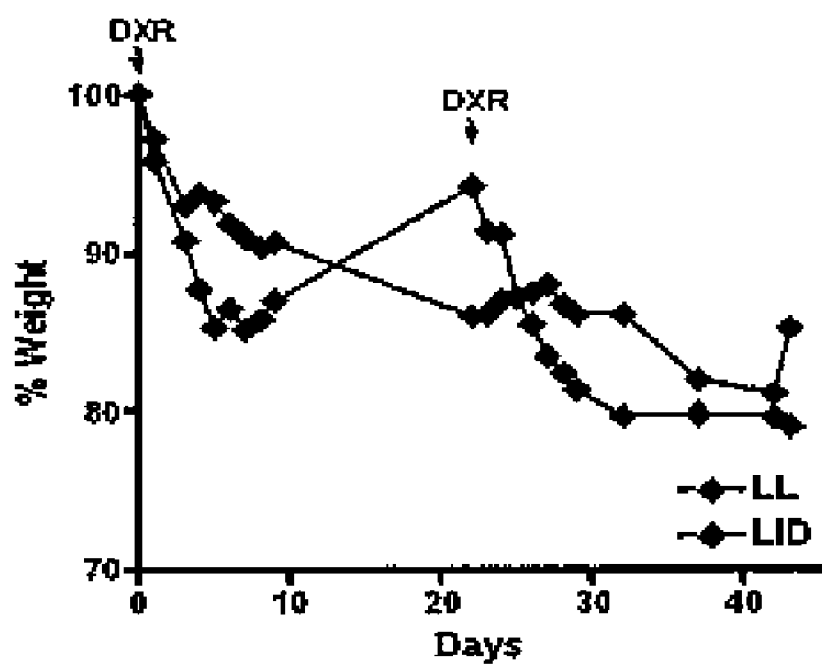

FIG. 22. Resistance to multiple treatments with doxorubicin. Doxorubicin was intravenously administered at 20 mg/kg on Day 0 and 28 mg/kg on Day 22 (n=5). The toxicity, evaluated by (A) percent survival and (B) daily weight measurements, are shown. p-value was calculated by log rank test (p<0.05).

Figure 23:
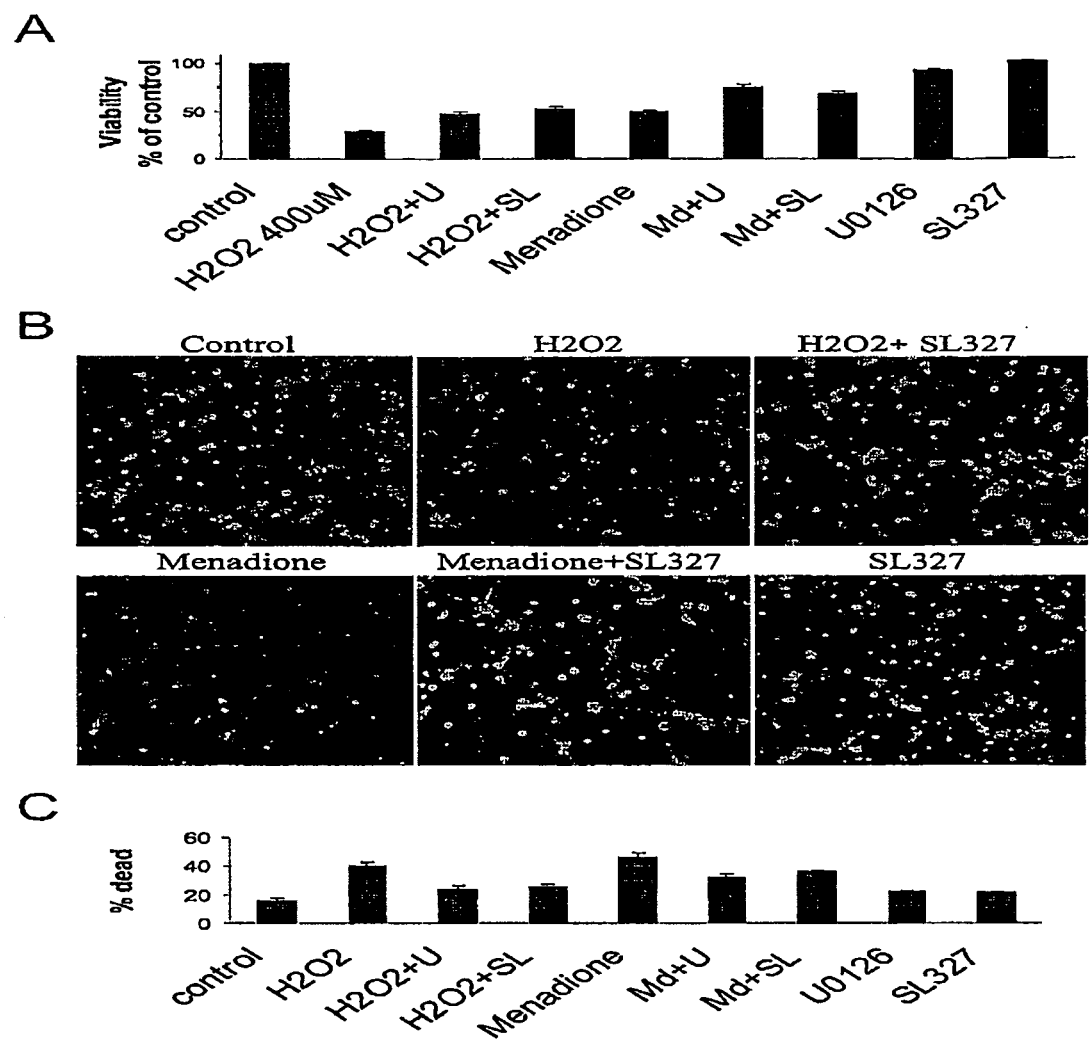

FIG. 23. Inhibiting ERK1/2 protects neurons against oxidative stress. Cortical neurons from E18 rat embryos were cultured onto 96-well plates (A) or glass coverslips in 6-well plates (B). On 10-14 DIV, the neurons were pre-treated with MEK1/ERK1/2 inhibitors U0126 or SL327. Oxidative stress was induced by hydrogen peroxide or menadione. Cell viability was measured with MTT survival assay (A) or live/dead assay (B). C) % death was calculated from the number of dead (red) and live (green) cells.

DETAILED DESCRIPTION OF THE INVENTION

In the present invention, it has been unexpectedly discovered that the deletion of SCH9/AKT genes from cells and/or short-term starvation (STS) treatment has a differential cyto-protective effect on normal cells as compared with cancer or cancer-like cells expressing constitutively actively $Ras2^{val19}$ (the cyto-protective effect may be up to 10,000 times more effective). Further, reduction of IGF-I/IGF-IR signaling or STS protected primary glial cells but not 6 different rat and human glioma and neuroblastoma cancer cell lines against chemotherapy. Liver IGF-I deficient (LID) mice were also protected against high dose chemotherapy confirming the in vitro results and providing a candidate drug target to replace starvation. STS in combination with the somatostatin analogue octreotide provided complete protection to mice but did not protect injected cancer cells against high dose chemotherapy. The present invention thus provides evidence for the efficacy of short-term starvation and/or lowering IGF-IR signaling in the protection of normal but not cancer cells against chemotherapy, radiotherapy or any other toxic treatment or environment.

One method of the invention involves starving a subject with cancer for 24-60 (e.g., 30-55, 35-50, 40-45, and 48) hours and administering to the subject a chemotherapy agent, thereby inducing differential stress resistance in the subject.

By "starving" is meant subjecting a cell or subject to reduced or no nutrients.

As used herein, a "subject" refers to a human or animal, including all mammals such as primates (particularly higher primates), sheep, dog, rodents (e.g., mouse or rat), guinea pig, goat, pig, cat, rabbit, and cow. In a preferred embodiment, the subject is a human. In another embodiment, the subject is an experimental animal or animal suitable as a disease model.

As used herein, "cancer" refers to a disease or disorder characterized by uncontrolled division of cells and the ability of these cells to spread, either by direct growth into adjacent tissue through invasion, or by implantation into distant sites by metastasis. Exemplary cancers include, but are not limited to, primary cancer, metastatic cancer, carcinoma, lymphoma, leukemia, sarcoma, mesothelioma, glioma, germinoma, choriocarcinoma, prostate cancer, lung cancer, breast cancer, colorectal cancer, gastrointestinal cancer, bladder cancer, pancreatic cancer, endometrial cancer, ovarian cancer, melanoma, brain cancer, testicular cancer, kidney cancer, skin cancer, thyroid cancer, head and neck cancer, liver cancer, esophageal cancer, gastric cancer, intestinal cancer, colon cancer, rectal cancer, myeloma, neuroblastoma, pheochromocytoma, and retinoblastoma. Preferably, the cancer is glioma, neuroblastoma, pheochromocytoma, or prostate cancer.

Chemotherapy agents are antineoplastic drugs used to treat cancer, including alkylating agents, anti-metabolites, plant alkaloids and terpenoids, topoisomerase inhibitors, anti-tumour antibiotics, monoclonal antibodies, oxidants, hormones, and the like. Preferable chemotherapy agents are methyl methanesulfonate, cyclophosphamide, etoposide, doxorubicin, and menadione. Other chemotherapy agents are known in the art, some of which are described below.

By short-term starvation, differential stress resistance (DSR) is induced in a subject with cancer, i.e., while the resistance of cancer cells to a chemotherapy agent is reduced or unchanged, the resistance of non-cancer cells (e.g., normal cells) to the chemotherapy agent is concomitantly increased.

DSR may also be induced by administering a cell growth inhibitor to a subject with cancer. A "cell growth inhibitor" inhibits the growth of a cell. For example, such inhibitors (e.g., IGFBPs, IGF-R blocking antibodies, and small molecule inhibitors such as octreotide) may inhibit IGF-I, IGF-IR, GH, Akt, Ras, Tor, or Erk by inhibiting gene expression or protein activity. In some embodiments, the serum concentration of IGF-I in the subject may be reduced by 75-90% (e.g., 80-85%), as compared to normal conditions. Other cell growth inhibitors are known in the art, some of which are described below.

Another method of inducing DSR in a subject with cancer is via reducing the caloric or glucose intake by the subject. In some embodiments, DSR may be achieved by reducing the caloric intake by 10-100% (e.g., 20-90%, 30-80%, 40-70%, 50-60%) or by reducing the blood glucose concentration in the subject by 20-50% (e.g., 25-45%, 30-40%, and 45%), as compared to normal conditions.

The methods of the invention may be combined to maximize DSR. For example, DSR may be induced in a subject with cancer by a combination of short-term starvation and administration of a cell growth inhibitor.

The methods described above can be used to improve the effectiveness of cancer treatment. A subject to be treated may be identified in the judgment of the subject or a health care professional, and can be subjective (e.g., opinion) or objective (e.g., measurable by a test or diagnostic method). To treat a subject with cancer, DSR is induced in the subject prior to the administration of an effective amount of a chemotherapy agent by short-term starvation, administration of an effective amount of a cell growth inhibitor, glucose, etc.

The term "treatment" is defined as administration of a substance to a subject with the purpose to cure, alleviate, relieve, remedy, prevent, or ameliorate a disorder, symptoms of the disorder, a disease state secondary to the disorder, or predisposition toward the disorder.

An "effective amount" is an amount of a compound that is capable of producing a medically desirable result in a treated subject. The medically desirable result may be objective (i.e., measurable by some test or marker) or subjective (i.e., subject gives an indication of or feels an effect).

A compound to be administered can be incorporated into pharmaceutical compositions. Such compositions typically include the compounds and pharmaceutically acceptable carriers. "Pharmaceutically acceptable carriers" include solvents, dispersion media, coatings, antibacterial and antifungal agents, isotonic and absorption delaying agents, and the like, compatible with pharmaceutical administration.

A pharmaceutical composition is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

It is advantageous to formulate oral or parenteral compositions in dosage unit form for ease of administration and uniformity of dosage. "Dosage unit form," as used herein, refers to physically discrete units suited as unitary dosages for the subject to be treated, each unit containing a predetermined quantity of an active compound calculated to produce the desired therapeutic effect in association with the required pharmaceutical carrier.

The dosage required for treating a subject depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Methods similar to those described above may be used to contact a cancer cell with a chemotherapy agent (e.g., to reduce resistance of the cancer cell to the chemotherapy agent) and to increase resistance of a non-cancer cell to the chemotherapy agent. Such method may involve, for example, starving the cell for 24-60 (e.g., 30-55, 35-50, 40-45, and 48) hours, and optionally, contacting the cell with a cell growth inhibitor; contacting the cell with a cell growth inhibitor; or cultivating the cell in a medium with reduced concentration of serum (e.g., by 10-90%, 20-80%, 30-70%, 40-60%, and 50%), IGF-I (e.g., by 10-100%, 20-90%, 30-80%, 40-70%, and 50-60%), or glucose (e.g., by 20-50%, 25-45%, 30-40%, and 45%), as compared to normal conditions.

These methods can be used to identify candidate protocols, cell growth inhibitors, and chemotherapy agents for in vivo applications. For example, a protocol, cell growth inhibitor, or chemotherapy agent may be tested using the methods described above. If the protocol, cell growth inhibitor, or chemotherapy agent leads to reduced or unchanged resistance of a cancer cell to a chemotherapy agent and increased resistance of a non-cancer cell to a chemotherapy agent under the same conditions, the protocol, cell growth inhibitor, or chemotherapy agent is identified to be a candidate for in vivo application of DSR induction.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE I

A Starvation Response-Based Differential Stress resistance method to enhance cancer Treatment Material and Methods
Cell Lines Primary mixed glial cells were obtained from the cerebral cortex of 1 to 3 day old Sprague Dawley rat pups (Charles River) as described before. Cells cultured for 10-14 days in DMEM/F12 medium with 10% fetal bovine serum (FBS) were used in assays. C6, A10-85, 9L and RG2 rat glioma cell lines and LN229 human glioma cell line and SH-SY5Y human neuroblastoma cell line were maintained in DMEM/F12 medium with 10% FBS at 37° C. under 5% $CO_2$.

STS Treatments

Cells were seeded into 96-well microtiter plates at 20,000-30,000 cells/well and incubated for 2 days. Cells were washed with phosphate buffered saline (PBS) prior to treatments as indicated in the text. All treatments were performed at 37° C. under 5% $CO_2$.

Glucose restriction was done by incubating cells in glucose free DMEM (Invitrogen) supplemented with either low glucose (0.5 gL) or normal glucose (1.0 gL) for 24 hours. Serum restriction was done by incubating cells in DMEMIF12 with either 10% or 1% FBS for 24 hours. IGF-I treatment was carried out by incubating cells for 48 hours in DMEM/F12 with 1% FBS and rhIGF-I (100 n g/ml, ProSpec-Tany TechnoGene, Rehovot, Israel), which is shown to be within the IGF-I level range for middle age humans. To antagonize IGF-I receptor activity, cells were incubated with neutralizing monoclonal anti-IGF-IR antibody (aIR3, 1 pg/ml; Calbiochem) in DMEM/F12 1% FBS for 24 hours.

In vitro Chemotherapeutic Treatment

A widely used chemotherapeutic drug (cyclophosphamide, CP, Sigma) was used for in vitro studies. CP was prepared in DMEM/F12 with 1% FBS at 40 mg/ml and was filter sterilized. The stock solution was stored at 4° C. for no longer than 2 weeks.

Following STS treatments, cells were incubated with varying concentrations of cyclophosphamide (6-15 mg/ml) for 10 hours in DMEM/F12 with 1% FBS. Cytotoxicity was measured by either LDH release using the CytoTox 96 Non-Radioactive Cytotoxicity Assay kit (Promega) or the ability to reduce methylthiazolyldiphenyltetrazolium bromide (MTT).

% LDH release was determined with reference to the maximum and background LDH release of control cells. MTT assay results were presented as percentage of MTT reduction level of control cells.

Yeast Strains and Growth Conditions

Experiments were carried out in wild type DBY746 MTα, leu2-3,112, his3D1, trp1-289, ura3-52, GAL+, and isogenic strains lacking either Sch9 (Fabrizio et al., 2001) or both Sch9 and Ras2 (Fabrizio et al., 2001). Wild type (DBY746) and sch9A strains expressing hyperactive Ras2$^{val19}$ constructed by transformation with a centromericplasmid containing Ras2$^{val19}$ (pRS406-Ras2$^{val19}$, CEN URA3). Yeast cultures were grown in liquid synthetic dextrose complete medium (SDC) with 2% glucose, supplemented with amino acids, adenine, as well as a four-fold excess of tryptophan, leucine, histidine, uracil. Strains harboring the centromeric plasmid containing Ras2$^{val19}$ were always grown in the absence of uracil to maintain selection.

Yeast Viability

Overnight cultures were diluted to OD$_{600}$ 0.1 into SDC medium. After 24 hours (day I), the appropriate strains were mixed 1:1 based on OD$_{600}$ and incubated for 2 hours. The mixed cultures were then treated with either cyclophosphamide (CP, 0.1 M) or methylmethionine sulphonium chloride (MMS, 0.01%, Sigma) in medium or water (STS). For treatment SDC, MMS was introduced directly into the mixed culture to a final concentration of 0.01%. However, due to the high concentration of CP (0.1 M) used, CP was dissolved directly into the medium. To do so, mixed cultures were centrifuged for 5 minutes at 2,500 rpm and the media was collected, in which CP was dissolved to a concentration of 0.1 M. The mixed culture was then resuspended in the CP-containing medium. For treatments in water (STS), mixed cultures were centrifuged for 5 minutes at 2,500 rpm and the media was replaced with either distilled/sterile water or drug-dissolved water. Viability was measured by quantifying colony-forming units (CFUs) every 24 hours by plating onto appropriate selective media. Viability of individual strains was measured using the same method as for the mixed cultures.

DSR Assays in Yeast

Stress resistance against MMS, menadione (Sigma), and H$_2$O$_2$ (Sigma) was measured by spotting serial dilutions of control and treated cells. Briefly, overnight cultures were diluted in 1 ml of liquid SDC medium with 2% glucose to an initial OD$_{600}$ 0.1 and incubated overnight shaking at 30° C. 24 hours later, aliquots of cells were washed and resuspended in water for 48 hours (STS). Following STS, cultures were diluted to OD$_{600}$ 1 in K-phosphate buffer and treated with menadione (1 mM; pH7.4) or H$_2$O$_2$ (400 mM, pH6.0) for 60 and 30 minutes, respectively. Then, serial dilutions were spotted onto YPD plates and incubated at 30° C. for 2-3 days.

In vivo Therapeutic Studies in Mice

The murine NX3IT28 cell line was generated by hybridization of the GD2-negative C1300 murine neuroblastoma cell line (A/J background) with murine dorsal root ganglional cells from C57BL16J mice, as previously described. The NXS2 subline was then created by the selection of NX3IT28 cells with high GD2 expression.

Six-to-seven-week-old female NJ mice, weighing 15-18 g were purchased from Harlan Laboratories (Harlan Italy, S. Pietro al Natisone, Italy) and housed in sterile enclosures under specific virus and antigen-free conditions. All procedures involving mice and their care were reviewed and approved by licensing and ethical committee of the National Cancer Research Institute, Genoa, Italy, and by the Italian Ministry of Health.

NJ mice were pretreated with 1 mg/kg/day doses of human octreotide (OCT, ProSpec-Tany TechnoGene, Rehovot, Israel) for 4 days given slowly through the tail vein in a volume of 100 μl and then injected intravenously with murine neuroblastoma NXS2 cell line (200,000/mouse), as previously described. After tumor cell inoculum, some groups of animals were starved for 48 hours and then i.v. treated with 80 mg/kg of Etoposide Teva (Teva Pharma B.V., Mijdrecht, Holland), administered as a single dose. Additional daily doses of OCT were administered for 4 days after chemotherapy. Control groups of mice without diet starvation and OCT treatment were also investigated.

Octreotide pre-treatment: 4 days, 1 mg/kg/day
NXS2: 200,000/mouse on day 4
STS: from day 4 to day 6 (after tumor cell inoculum)
Etoposide: 80 mg/kg on day 7
Octreotide post-treatment: days 8-11

To determine toxicity and efficacy, mice were monitored routinely for weight loss and general behavior. The animals were killed by cervical dislocation after being anesthetized with xilezine (Xilor 2%, Bio98 Srl, Milan, Italy) when they showed signs of poor health, such as adbominal dilatation, dehydration, or paraplegia. Survival time was used as the main criterion for determining the efficacy of each treatment.

The statistical significance of differential survival between experimental groups of animals was determined by Kaplan-Meier curves and log-rank eeto test by the use of StatDirect statistical software (Camcode, Ashwell, UK).

In some experiments, four-week-old female CD1 mice (Harlan), weighing 18-20 g were used to evaluate stress resistance after 60 hours of starvation. These animals, i.v. injected with 110 mg/kg etoposide, were monitored routinely for weight loss and general behavior. Survival time was used as the main criterion for determining the differential stress resistance after short-term starvation.

Experimental

The inventor's diligent studies in S. cerevisiae and those of others in worms, flies, and mice have uncovered a strong association between life span extension and resistance to multiple stresses. This resistance is observed in long-lived yeast cells lacking the orthologs of the human Ras (RAS2) and Akt (SCH9/AKT) proto-oncogenes and in long-lived worms and mice with reduced activity of homologs of the IGF-I receptor (IGF-IR), which functions upstream of Ras and Akt in mammalian cells, also implicated in many human cancers. This resistance is also observed in model systems in which the calorie intake is reduced by 30 to 100%. Based on the unexpected discovery of the role of Ras2 and Sch9/Akt in the negative regulation of stress resistance together with the association between mutations that activate IGF-IR, Ras or Akt and many human cancers, it was believed that normal but not cancer cells would respond to starvation or down-regulation of growth hormone GH/IGF-I signaling by entering a chemotherapy resistance mode. It was also noted that one of the major phenotypic characteristics of malignant cells is the hyperactivation of pathways including the IGF-IR, Ras and Akt pathways and the ability to grow or remain in a growth mode even in the absence of growth factors.

To test whether constitutively active oncogenes or oncogene homologs would prevent the switch to a protective maintenance mode in response to starvation, it was first determined whether acute starvation would be as effective in increasing stress resistance as long-term calorie restriction (CR).

DSR studies in S. cerevisiae were performed. A short-term starvation paradigm was selected as well as the deletion of the SCH9/AKT and/or RAS2 genes, each of which mimics in part calorie restriction. It was believed that the combination of these genetic manipulations with starvation would maximize DSR. The combination of STS (switch from glucose medium to water for 24-48 hours) with the deletion of SCH9/AKT or both SCH9/AKT and RAS2 homolog causes a 1,000- to 10,000-fold DSR in response to a 30- to 60-minute treatment with hydrogen peroxide or menadione compared to cells expressing the constitutively active RAS2$^{val19}$ or cells lacking SCH9/AKT (sch9/akfA) but expressing RAS2$^{val19}$ (sch9/aktΔ RAS2$^{val19}$) (FIG. 1A). STS of wild type cells also caused DSR relative to RAS2$^{val19}$ expressing cells but the differential effect for wild type cells was lower in response to $H_2O_2$ treatment and was not observed after treatment with the hydrogen peroxide and superoxide generating agent menadione (FIG. 1A). The typical increase of resistance to hydrogen peroxide after STS compared to incubation in medium was between 10- and 100-fold for wild type cells. The objective for this experiment was to model in a simple system the effect of the combination of short-term starvation and a genetic approach on differential stress resistance between normal and cancer cells. The results showed that the expression of the oncogene-like RAS2$^{val19}$ prevented the 1,000- to 10,000-fold protection caused by the combination of STS and inhibition of Sch9/Akt activity.

To test whether DSR would also occur after treatment of yeast with chemotherapy drugs, the effect of STS and SCH9/AKT mutations on the toxicity caused by alkylating agents methyl methanesulfonate (MMS) and cyclophosphamide (CP, a widely used chemotherapy drug) was studied. As a model for the effect of STS and/or IGF-I inhibition on advanced stage cancer in which cancer cells were mixed with normal cells, mutants lacking SCH9/AKT with mutants lacking SCH9/AKT but also expressing RAS2$^{val19}$ were mixed in the same flask at a 25:1 ratio. They were then exposed to chronic treatment with CP or MMS. The viability of the two populations could be assessed by the ability of each population to grow on plates containing different selective media. Of the approximately 10 million sch9/aktΔRAS2$^{val19}$ cells mixed with 250 million sch9/aktΔ, none of the sch9/aktΔRAS2$^{val19}$ cells survived a 48-hour treatment with 0.01% MMS (FIG. 1B). By contrast, the great majority of sch9/aktΔ survived this treatment (FIG. 1B). Similar results were obtained with mixed sch9/aktΔRAS2$^{val19}$/sch9/aktΔ cultures treated with cyclophosphamide (CP) (FIG. 1C). A similar experiment in which each cell type was treated with CP separately was also performed, and a similar differential stress resistance between cells expressing RAS2$^{val19}$ and cells lacking SCH9/AKT was observed (FIG. 1D). Notably, a 48-hour treatment with CP was toxic to both RAS2$^{val19}$ and wild type cells (FIG. 1D) suggesting that the lack of SCH9/AKT causes a major increase in protection relative to RAS2$^{val19}$ expressing cells but also wild type cells. These results confirm that DSR obtained by altering gene expression is effective in protecting normal cells but not cancer-like cells against chemotherapy.

To test the efficacy of the starvation-based DSR method on mammalian cells, primary rat mixed glial cells (astrocytes+ 5-10% microglia) or three different rat glioma tumor cell lines in medium containing either normal (1 g/L) or low (0.5 g/L) glucose (1 g/L. glucose is within the normal human blood glucose range. A 0.5 g/L glucose concentration can be reached during starvation) were incubated and then treated with the chemotherapy drug CP. Whereas 80% of glial cells were resistant to 12 mg/ml CP in the presence of 0.5 g/L glucose, only 20% of the cells survived this treatment in 1 g/L glucose (FIG. 2A). The differential stress resistance between the two concentrations of glucose (0.5 and 1 g/L) was observed starting at 6 mg/ml CP but became much more pronounced at 12 mg/ml CP (FIG. 2A). By contrast, the lower glucose concentration did not affect the resistance of either C6, A10-85, or RG2 glioma cells to the same doses of CP (FIG. 2A). The lower glucose concentration actually increased the toxicity of CP to RG2 glioma cells at 6 and 8 mg/ml doses (FIG. 2A).

A similar DSR effect was obtained with a different form of starvation achieved by reducing the serum concentration. Treatment with 15 mg/ml CP was toxic to primary glial cells in 10% serum but the switch to 1% serum caused a major reduction in toxicity (FIG. 2B). Instead, the same concentration of CP was as toxic to C6 glioma cells in 10% serum as it was in 1% serum (FIG. 2B).

In S. cerevisiae experiments it was shown that the deletion of SCH9/AKTprotects whereas the constitutive activation of Ras2 (RAS2$^{val19}$) sensitizes the yeast cells to chemotherapy drugs. Since mammalian Ras and Akt function downstream of the IGF-I receptor, and considering the role of the IGF-I pathway in regulating stress resistance, the effect of IGF-I and of an antibody against IGF-IR on DSR was also tested. Treatment with 100 ng/ml IGF-I (in the low IGF-I level range for normal human adults) caused a 4-fold increase in the toxicity of cyclophosphamide to primary mixed glia but only caused a minor increase in the toxicity of CP to C6 glioma cells (FIG. 2C). Furthermore, pre-incubation with an IGF-IR antagonist antibody protected primary glia but only provided a small protection of two of the three glioma lines tested against CP toxicity (FIG. 2D). These results in normal glia and in glioma cell lines are consistent with those in yeast cells and showed that short-term starvation and/or drugs that down-regulate GH/IGF-I/Ras/Akt signaling can protect normal cells much more effectively than cancer cells against chemotherapy.

In an in vivo test, mice were treated with high doses of chemotherapy in combination with STS and/or a GH/IGF-I lowering therapy. For this purpose etoposide, a widely used chemotherapy drug which damages DNA by multiple mechanisms and displays a generalized toxicity profile ranging from myelosuppression to liver and neurologic damage, was selected. Unusually high doses of etoposide (80-110 mg/Kg) were administered after a GH/IGF-I lowering treatment, period of starvation or both. In humans, a third of this concentration of etoposide (30-45 mg/Kg) is considered to be a high dose and therefore in the upper allowable range.

To reduce GH/IGF-I A/J mice were pre-treated for four days with the growth hormone release inhibitor somatostatin analogue octreotide. This pre-treatment was followed by etoposide administration. A sub-group of mice were also starved for 48 hours before treatment with etoposide. The mice pre-treated with octreotide received this treatment for 4 additional days after chemotherapy. Whereas 80 mg/Kg etoposide killed 43% of control (Eto, n=23, 2 experiments) and 29% of octreotide pre-treated mice (OCT/Eto, n=17), in two separate experiments none of the mice treated with octreotide and also pre-starved for 48 hours died after 80 mg/kg etoposide treatment (OCT/STS/Eto/OCT, n=35) and only one of the mice that were only starved (STS/Eto, n=16) died after etoposide treatment (FIG. 3A). Remarkably, STS/octreotide pre-treated mice, which lost 25% of the weight during the 48 hours of starvation, regained all the weight in the four days after etoposide treatment (FIG. 3B) whereas in the same period the control mice lost approximately 20% of the weight (FIG. 3B). Non-STS pre-treated mice also showed reduced mobility and ruffled hair.

The effect of STS alone on the protection of mice of another genetic background (CD1) was also tested. To determine whether an extended STS strategy can be effective against a higher concentration of chemotherapy drugs 110 mg/Kg etoposide was administered and also the starvation period was increased to 60 hours. Based on the experiments with oxidative stress, it was determined that this period is the maximum STS that provides protection. Longer starvation periods can weaken the animals and have the opposite effect. This concentration of etoposide killed all the control mice (Eto 110) but none of the STS pre-treated mice (STS/Eto 110, n=5) (FIG. 3C). As for the A/J mice, CD1 STS pre-treated mice, which lost 40% of the weight during the 60 hours of starvation, regained all the weight in the week after the etoposide treatment and showed no sign of toxicity (FIG. 3D). In summary, out of 56 mice from two genetic backgrounds that were starved before etoposide treatment, only one mouse from the STS only group and none of the mice from the STS/octreotide pre-treated group died. By contrast, out of the 45 mice treated with etoposide alone or etoposide and octreotide, 20 died of toxicity.

These results are consistent with the yeast and glia/glioma data showing increased resistance to chemotherapy toxicity in response to starvation. In mice, octreotide alone was not sufficient to protect against etoposide toxicity and virtually all the protection was due instead to STS. Notably, octreotide treatment was sufficient to protect mice against the superoxide generator paraquat.

To determine whether the differential stress resistance observed in yeast and mammalian cells would also occur in mice, the survival of mice injected with cancer cells was followed. A particularly aggressive tumor line (NXS2) was selected, which models a common childhood cancer: neuroblastoma. The NXS2 neuroblastoma line induces consistent and reproducible metastases in a pattern which resembles the situation observed in neuroblastoma patients at advanced stages of disease. Experimental metastases in the liver, kidneys, adrenal gland, and ovaries were observed after 25-30 days of the inoculation with 200,000 NXS2 cells (Table 1) as previously described. Although the tumor development and survival of STS/etoposide treated mice was not significantly different from that of controls (Gr. 6 vs Gr: 1 p=0.14), half of the pre-starved mice were alive at a point when the non-etoposide treated mice were all dead (FIG. 4A, Table 1) suggesting that STS only partially protects cancer cells against etoposide. Thus, several or many chemotherapy cycles in combination with STS may be required for the effective killing of all the metastasized cancer cells.

Remarkably, none of the octreotide/STS/etoposide injected with NXS2 cells died until day 46, and at day 90, 25% of these mice were still alive (FIG. 4, Table 1) (Gr. 4 vs Gr. 1 p=0.0001). Mice in the NXS2/etoposide and octreotide/NXS2/etoposide groups also did not develop tumors until day 80 (Table 1) but, as described above, 50-65% of them were killed by the initial dose of etoposide (FIGS. 3A and 4B). The 25% cancer-free rate at 90 days of the octreotide/STS/NXS2/etoposide-treated mice (FIG. 4A) together with the major postponement of metastasis and death in the remaining 75% of these mice (Table 1) suggest that this treatment is a highly effective strategy to kill cancer cells while protecting the organism. Considering that the STS/etoposide/NXS2-treated group did not survive as long as the group that also included octreotide (survival of Gr. 6 vs. Gr. 4 p=0.01), these results indicate that octreotide contributes to killing NXS2 cells, possibly by inducing apoptosis as shown by others. In fact, somatostatin receptors are expressed in neuroblastoma cells but also in breast and colon cancer cells. Thus, octreotide may play a dual role in enhancing protection of normal cells while enhancing the death of cancer cells. However, in the absence of short-term starvation) octreotide alone did not protect mice against NXS2-dependent death (FIG. 4), suggesting that it is the synergism between etoposide and octreotide that is effective in killing cancer cells. The 90-day cancer free survival of the 3 octreotideletoposide-treated mice (Table 1) that were not killed by the initial dose of etoposide (FIG. 4B) is consistent with such an effective role of the combination of high doses of chemotherapy and octreotide in curing metastatic cancer.

The conserved DSR response between normal cells (yeast and mammalian cells) and cancer-like or cancer cells demonstrates that it is possible to protect the organism much more effectively than under normal feeding conditions while maintaining the toxicity of chemotherapy to tumor cells. The basis for this is the existence of a "maintenance mode" entered in response to starvation for the purpose of investing the remaining energy resources in protecting every cell and tissue. In yeast, worms and mice starvation or the genetic manipulation of starvation response pathways causes a major increase in protection against multiple stresses including heat shock and oxidative damage. In mammals, starvation causes a reduction in IGF-I levels which is associated with increased stress resistance. IGF-I is only one of the factors involved in the starvation response, but are among the major negative regulators of the entry into a stress resistant mode. Although the role of calorie restriction or reduced activity of the GH/IGF-I/RAS/AKT axis in the stress resistance of primates is unknown, studies in monkeys and humans suggest that calorie restriction can have effects similar to those observed in simple eukaryotes and mice.

One of the most surprising discovery of this invention is the ability of mice that have been starved for 48 hours to gain back the 25-40% weight lost during starvation even in the presence of doses of etoposide that cause a 20-30% weight loss and kill over 40% of the control mice. This high resistance to a drug that damages the DNA of dividing cells and is particularly toxic to blood cells would be consistent with the entry of most or all of the normally dividing cells into a highly protective cell cycle arrested mode in response to the 48 hour starvation. Since etoposide is known to be rapidly excreted

TABLE 1

| Groups | Liver | Kidneys | Ovaries | Adrenal gland | Hemorrhagic ascites | Median survival (days) | Survival Range (days) |
| --- | --- | --- | --- | --- | --- | --- | --- |
| Gr. 1 Control | 16/16 | 14/16 | 13/16 | 3/16 | 16/16 | 32 | 32-38 |
| Gr. 2 OCT | 8/8 | 8/8 | 8/8 | 2/8 | 8/8 | 33 | 31-37 |
| Gr. 3 OCT/STS/OCT | 8/8 | 5/8 | 6/8 | 1/8 | 8/8 | 31 | 27-33 |
| Gr. 4 OCT/STS/Eto/OCT | 5/8* | 5/8* | 5/8* | 0/8* | 6/8* | 56* | 46-90 |
| Gr. 5 STS | 8/8 | 5/8 | 7/8 | 1/8 | 8/8 | 30 | 26-35 |
| Gr. 6 STS/Eto | 14/14 | 7/14 | 5/14 | 0/14 | 14/14 | 44 | 35-60 |
| Gr. 7 Eto | 1/3* | 1/3* | 1/3* | 0/3* | 1/3* | 90* | 87-90 |
| Gr. 8 OCT/Eto/OCT | 0/3** | 0/3** | 0/3** | 0/3** | 0/3** | 90** | 90-90 |

(up to 90% within 48 hours in humans), such "protective mode" may only need to last for a few days.

Chemotherapy treatment has relied mainly on one or a combination of several DNA damaging agents such as etoposide, cyclophosphamide, and doxorubicin. Although these agents are supposedly much more toxic to cancer cells than to normal cells, the in vitro studies show that cyclophoshamide, for example, can be as or more toxic to primary glial cells as it is to glioma cells. This implies that the combination of multiple chemotherapy drugs causes massive damage to normal cells, especially at high doses. Thus, it is particularly important to apply strategies such as the one presented here and aimed at reducing or eliminating the side effects of normal doses of chemotherapy or limiting the toxicity of very high doses of chemotherapy that are effective against metastatic cancers.

Figure 1:
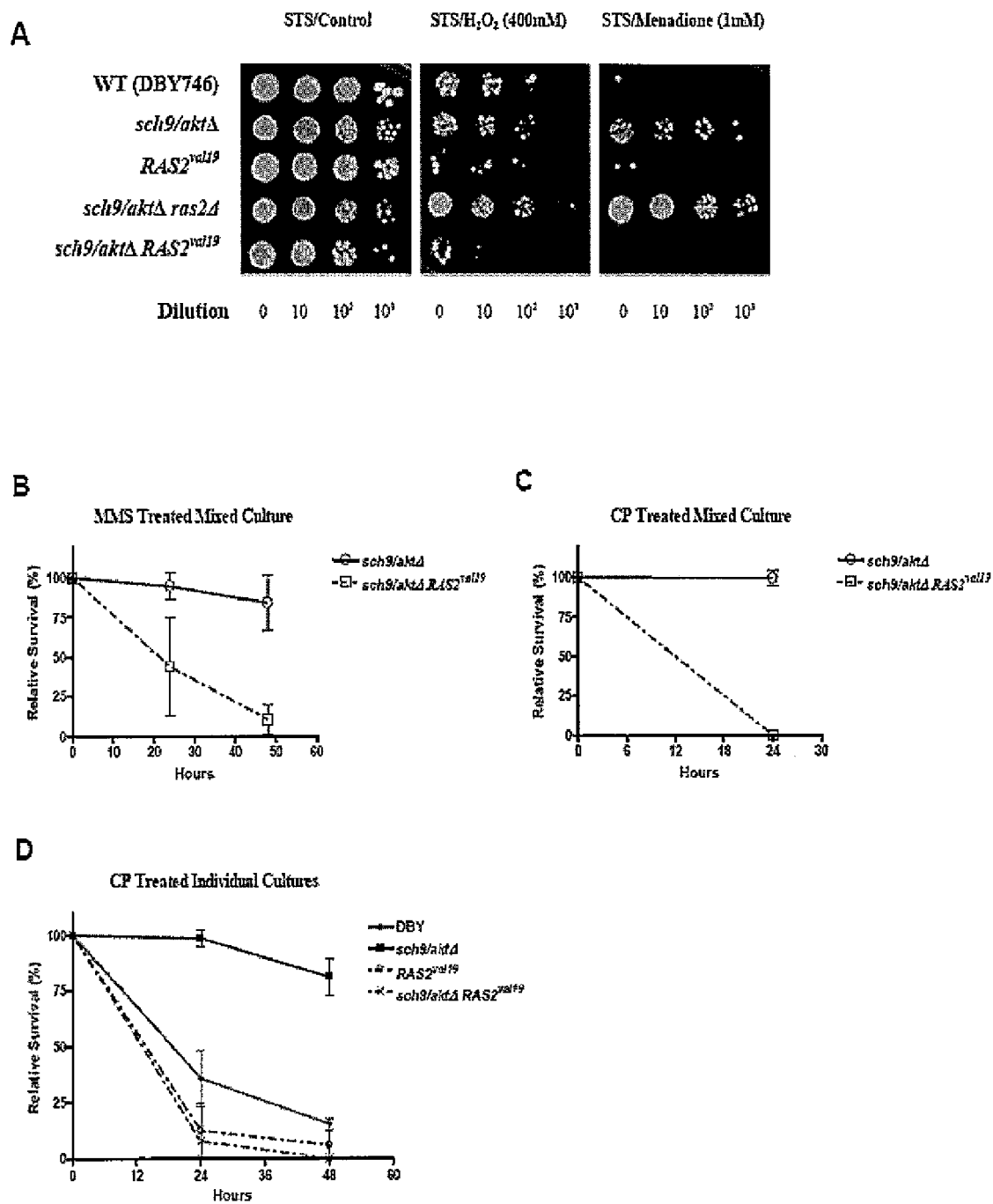
FIG. 1. A) DSR of short-term starvation (STS) against acute $H_2O_2$ or menadione treatments. Survival of wild type (DBY746), sch9/akt$\Delta$, RAS2$^{val19}$, sch9/akt$\Delta$ras2$\Delta$ and sch9/akt$\Delta$RAS$^{val19}$ after a 48-hour starvation and exposure to $H_2O_2$ (400 mM, 60 min) and to menadione (1 mM, 30 min). The cultures were diluted in K-phosphate buffer to an initial $OD_{600}$ 1 for both treatments. Serial dilutions were spotted onto YPD plates and incubated at 30° C. for 2-3 days. This experiment was repeated at least 3 times with similar results. A representative experiment is shown. B, C) DSR against chronic CP and MMS treatments in mixed cultures. sch9/akt$\Delta$ and sch9/akt$\Delta$RAS2$^{val19}$ were mixed and incubated for 2 hours shaking at 30° C. The initial sch9/aktΔ:sch9/aktΔ RAS2$^{val19}$ ratio as measured by growth on selective media was 25:1. Mixed cultures were treated with either CP (0.1 M) or MMS (0.01%). Viability was measured by quantifying colony-forming units (CFUs) every 24 hours by plating onto appropriate selective media. This experiment was repeated at least 2 times with similar results. A representative experiment is shown. D) DSR against chronic CP treatment. Wild type (DBY746), sch9/aktΔ, RAS2$^{val19}$, sch9/aktΔ and sch9/aktΔRAS2$^{val19}$ stains were individually grown and treated with CP (0.1 M). Viability was measured by the same method as in the mixed culture experiment.

Notably, the differential stress resistance of mammalian cells to the alkylating agents cyclophosphamide by the starvation-response methods was less than 10-fold whereas starved yeast lacking SCH9/AKT reached a 1,000-10,000-fold higher resistance to menadione, hydrogen peroxide, MMS, and cyclophosphamide compared to cancer-like $RAS2^{val19}$ expressing yeast cells (FIGS. 1 and 2). Furthermore, the 10,000-fold differential toxicity in yeast was obtained after only 30 minutes with hydrogen peroxide compared to the several days required for the differential toxicity of MMS or cyclophosphamide. Although toxic molecules such as hydrogen peroxide or menadione are probably not suitable for human treatments, these results suggest that the selection of novel chemotherapy drugs in combination with DSR can result in a greatly more effective cancer treatment and may lead to treatments that can be carried out in minutes to hours. The ability to reach a 10,000-fold differential toxicity between cancer cells and normal human cells would most likely lead to the cure of many cancers including those at advanced metastatic stages. Considering the remarkable results obtained with the aggressive NXS2 neuroblastoma line that was injected in mice it is reasonable to expect novel drugs and conditions that can yield results close to the 10,000-fold DSR.

References

1. Holzenberger, M. et al. IGF-I receptor regulates lifespan and resistance to oxidative stress in mice. Nature 421, 182-7 (2003).

2. Lithgow, G. J., White, T. M., Melov, S. & Johnson, T. E. Thermotolerance and extended life-span conferred by single-gene mutations and induced by thermal stress. Proc. Natl. Acad. Sci. USA 92, 7540-4 (1995).

3. Longo, V. & Finch, C. E. Evolutionary medicine: from dwarf model systems to healthy centenarians? Science 299, 1342-1346 (2003).

4. Migliaccio, E. et al. The p66shc adaptor protein controls oxidative stress response and life span in mammals. Nature 402, 309-13 (1999).

5. Fabrizio, P., Pozza, F., Pletcher, S. D., Gendron, C. M. & Longo, V. D. Regulation of longevity and stress resistance by Sch9 in yeast. Science 292, 288-90. (2001).

6. Longo, V. D. & Finch, C. E. Evolutionary Medicine: from Dwarf Model Systems to Healthy Centenarians? Science 299, 1342-1346 (2003).

7. Fabrizio, P. et al. SOD2 Functions Downstream of Sch9 to Extend Longevity in Yeast. Genetics 163, 35-46 (2003).

8. Pollak M. N., Schernhammer, E. S. & Hankinson, S. E. Insulin-like growth factors and neoplasia. Nat Rev Cancer 4, 505-18 (2004).

9. Lass, A, Sohal, B. H., Weindruch, R., Forster, M. J. & Sohal, R. S. Caloric restriction prevents age-associated accrual of oxidative damage to mouse skeletal muscle mitochondria. Free Radic Biol Med 25, 1089-97 (1998).

10. Harper, J. M. et al. Stress resistance and aging: influence of genes and nutrition. Mech Ageing Dev 127, 687-94 (2006).

11. Bruce-Keller, A. J., Umberger, G., McFall, R. & Mattson, M. P. Food restriction reduces brain damage and improves behavioral outcome following excitotoxic and metabolic insults. Ann Neuro 145, 8-15 (1999).

12. Fabrizio, P. et al. Sir2 blocks extreme life-span extension [see comment]. Cell 123, 655-67 (2005).

13. Kaeberlein, M. et al. Regulation of yeast replicative life span by TOR and Sch9 in response to nutrients [see comment]. Science 310, 1193-6 (2005).

14. Lin, S. J., Defossez, P. A. & Guarente, L. Requirement of NAD and SIR2 for lifespan extension by calorie restriction in *Saccharomyces cerevisiae*. Science 289, 2126-8. (2000).

15. Poole, C. J. et al. Epirubicin and cyclophosphamide, methotrexate, and fluorouracil as adjuvant therapy for early breast cancer. N Engl J Med 355, 185 1-62 (2006).

16. Brown-Borg, H. M., Rakoczy, S. G., Romanick M. A. & Kennedy, M. A. Effects of growth hormone and insulin-like growth factor I on hepatocyte antioxidative enzymes. Exp Biol Med 227, 94-104 (2002).

17. Marietta, J. et al. Effect of training on the GHIIGF-I axis during exercise in middle-aged men: relationship to glucose homeostasis. Am J Physiol Endocrinol Metab 283, E929-36 (2002).

18. Grunberg, S. M. Cyclophosphamide and etoposide for non-small cell and small cell lung cancer. Drugs 58 Suppl3, 11-5 (1999).

19. Mistry, A. R. et al. DNA topoisomerase II in therapy-related acute promyelocytic leukemia. N Engl J Med 352, 1529-38 (2005).

20. Vinolas, N., Graus, F., Mellado, B., Caralt, L. & Estape, J. Phase I1 trial of cisplatinum and etoposide in brain metastases of solid tumors. J Neurooncol 35, 145-8 (1997).

21. Kroger, N. et al. Busulfan, cyclophosphamide and etoposide as high-dose conditioning therapy in patients with malignant lymphoma and prior dose-limiting radiation therapy. Bone Marrow Transplant 21, 1171-5 (1998).

22. Gronbaek, H. et al. Inhibitory effects of octreotide on renal and glomerular growth in early experimental diabetes in mice. J Endocrinol 172, 637-43 (2002).

23. Tang, C., Liu, C., Zhou, X. & Wang, C. Enhanced inhibitive effects of combination of rofecoxib and octreotide on the growth of human gastric cancer. Int J Cancer 112, 470-4 (2004).

24. Lode, H. N. et al. Targeted interleukin-2 therapy for spontaneous neuroblastoma metastases to bone marrow. J Natl Cancer Inst 89, 1586-94 (1997).

25. Briganti, V. et al. Imaging of somatostatin receptors by indium-11 1-pentetreotide correlates with quantitative determination of somatostatin receptor type 2 gene expression in neuroblastoma tumors. Clin Cancer Res 3, 2385-91 (1997).

26. Smitha, M. C., Maggi, M. & Orlando, C. Somatostatin receptors in non-endocrine tumours. Dig Liver Dis 36 Suppl 1, S78-85 (2004).

27. Longo, V. D. & Kennedy, B. K. Sirtuins in aging and age-related disease. Cell 126, 257-68 (2006).

28. Norrelund, H., Nair, K. S., Jorgensen, J. O., Christiansen, J. S. & Moller, N. The protein-retaining effects of growth hormone during fasting involve inhibition of muscle-protein breakdown. Diabetes 50, 96-104 (2001).

29. Leiser, S. F., Salmon, A. B. & Miller, R. A. Correlated resistance to glucose deprivation and cytotoxic agents in fibroblast cell lines from long-lived pituitary dwarf mice. Mech Ageing Dev 127, 821-9 (2006).

30. Walford, R. L., Mock, D., Verdery, R. & MacCallum, T. Calorie restriction in biosphere 2: alterations in physiologic, hematologic, hormonal, and biochemical parameters in humans restricted for a 2-year period. J Gerontol A Biol Sci Med Sci 57, B211-24 (2002).

31. Roth, G. S., Ingram, D. K. & Lane, M. A. Caloric restriction in primates and relevance to humans. Ann N Y Acad Sci 928, 305-15 (2001).

32. McCarthy, K. D. & de Vellis, J. Preparation of separate astroglial and oligodendroglial cell cultures from rat cerebral tissue. J Cell Biol 85, 890-902 (1980).

33. Greene, L. A. et al. Neuronal properties of hybrid neuroblastoma X sympathetic ganglion cells. Proc Natl Acad Sci USA 72, 4923-7 (1975).

EXAMPLE II

Starvation and IGF-I Reduction Protect Normal But not Cancer Cells Against High Dose Chemotherapy The inventor's studies in *S. cerevisiae* and those of others in worms, flies, and mice have uncovered a strong association between life span extension and resistance to multiple stresses. This resistance is observed in long-lived yeast cells lacking the orthologs of the human Ras (RAS2) and Akt (SCH9/AKT) proto-oncogenes and in long-lived worms and mice with reduced activity of homologs of the IGF-I receptor (IGFIR), which functions upstream of Ras and Akt in mammalian cells, and is also implicated in many human cancers. This resistance is also observed in model systems in which the calorie intake is reduced by at least 30%.

To test whether constitutively active oncogenes or oncogene homologs can prevent the switch to a protective maintenance mode in response to starvation, it was first determined whether acute starvation would be as effective in increasing stress resistance as it has been shown for long-term calorie restriction (CR). Such long-term CR strategy would not be appropriate for human chemotherapy treatments since it requires several months to be effective.

DSR studies were first performed in *S. cerevisiae*. A short-term starvation paradigm as well as the deletion of the SCH9/AKT and/or RAS2 genes were selected, each of which mimics in part calorie restriction and was shown in previous studies to cause high resistance to oxidative stress. It was believed that the combination of these genetic manipulations with starvation would maximize DSR. The combination of STS (switch from glucose medium to water at day 1 [OD=9-10] and incubation in water for 24-48 hours) with the deletion of SCH9/AKT or both SCH9/AKT and RAS2 increased resistance to a 30- to 60-minute treatment with hydrogen peroxide or menadione a 1,000- to 10,000-fold compared to cells expressing the constitutively active oncogene homolog $RAS2^{val19}$ or cells lacking SCH9/AKT (sch9/aktΔ) but expressing $RAS2^{val19}$ (sch9/aktΔ$RAS2^{val19}$) (FIG. 10A). The rationale for this experiment was to model in a simple system the effect of the combination of short-term starvation and a genetic approach on the differential protection of normal and cancer cells. The results show that the expression of the oncogene-like $RAS2^{val19}$ prevents the 1,000-10,000-fold protection caused by the combination of STS and inhibition of Sch9/Akt activity.

The effect of another oncogene homolog (SCH9/AKT) on resistance to oxidants was tested. As with $RAS2^{val19}$, overexpression of SCH9/AKT sensitized yeast cells to both $H_2O_2$ and menadione was also tested (FIG. 10B). Similarly to the effect of the deletion of RAS2 and SCH9/AKT, the deletion of the homolog of TOR, another gene implicated in cancer, slightly increased the resistance to oxidants. Whereas the expression of $RAS2^{val1}$ completely reversed the protective effect of the deletion of sch9/akt, it only had a minor effect on the reversal of the protective effect of the tor1Δ (FIG. 10B). This is an important difference because it suggests that it may be risky to achieve DSR by inhibiting intracellular targets since inhibition of certain targets may also protect cancer cells.

To test whether DSR would also occur after treatment of yeast with chemotherapy drugs, the effect of SCH9/AKT mutations on the toxicity caused by alkylating agents methyl methanesulfonate and cyclophosphamide (CP, a widely used chemotherapy drug) was studied. As a model for the effect of STS and/or IGF-I inhibition on metastatic cancer, mutants lacking SCH9/AKT were mixed in the same flask with mutants lacking SCH9/AKT but also expressing $RAS2^{val19}$ at a 25:1 ratio and the mixture was exposed to chronic treatment with CP or MMS. The monitoring of the viability of the two mixed populations was possible since each population can be distinguished by growth on plates containing different selective media. Of the approximately 10 million sch9/aktΔ$RAS2^{val19}$ cells mixed with 250 million sch9/aktΔ, less than 5% of the sch9/aktΔ$RAS2^{val19}$ cells survived a 48-hour treatment with 0.01% MMS (FIG. 6A). By contrast, the great majority of sch9/aktΔ survived this treatment (FIG. 6A). The combination of these mutations with STS was also effective against a yeast model for cancer cells and killed all the $RAS2^{val19}$-expressing cells by 24 hours. Similar results were obtained with mixed sch9/aktΔ$RAS2^{a l19}$/sch9/aktΔ cultures and cyclophosphamide treatment (FIG. 6B). An experiment in which each cell type was treated with CP separately was also performed, and a similar differential stress resistance between cells expressing $RAS2^{val19}$ and cells lacking SCH9/AKT was observed (FIG. 10C). These results confirm that mutations in the Ras and Sch9/Akt and starvation are effective in protecting normal cells but not yeast cells that model cancer cells ($RAS2^{val19}$) against chemotherapy.

To test the efficacy of the starvation-based DSR method on mammalian cells, primary rat mixed glial cells (astrocytes+ 5-10% microglia) or three different rat and one human glioma and one human neuroblastoma cell lines were incubated in medium containing 1% serum and either normal (1 g/L) or low (0.5 g/L) glucose and then treated with the chemotherapy drug CP (1 g/L glucose is within the normal human blood glucose range whereas a 0.5 g/L glucose concentration can be reached in humans during starvation). The 1% serum concentration minimizes the contribution of glucose from serum, which is approximately 1 g/L to avoid major differences in proliferation. Glia and glioma cells were allowed to reach a 100% confluency. Whereas 80% of glial cells were resistant to 12 mg/ml CP in the presence of 0.5 g/L glucose, only 20% of the cells survived this treatment in 1 g/L glucose (FIG. 2A). The differential stress resistance between the two concentrations of glucose (0.5 and 1 g/L) was observed starting at 6 mg/ml CP but became much more pronounced at 12 mg/ml CP (FIG. 2A). By contrast, the lower glucose concentration did not affect the resistance of cancer cell lines including C6, A10-85, RG2 rat glioma, LN229 human glioma or human SH-SY5Y neuroblastoma cells to 12-14 mg/ml CP (FIG. 2A). The lower glucose concentration actually increased the toxicity of CP to RG2 glioma cells at 6 and 8 mg/ml doses (FIG. 2A). To determine whether the DSR is affected by the high cell density, this experiment was repeated with cells that were only 70% confluent and similar results were obtained (FIG. 11).

To determine whether the Ras/Erk pathway may be implicated in the unresponsiveness of the glioma and neuroblastoma cells above to starvation the phosphorylation of Erk, which functions downstream of Ras, was measured in 10% serum or serum starved cells. The phosphorylation data indicate that 2 of the 5 lines maintain a high level of Erk activity even after a 16-hour starvation (FIG. 11B), in agreement with the 30% frequency of Ras mutations in human cancers. The reduction of Erk phosphorylation but inability to increase protection to cyclophosphamide in the other 3 lines (FIG. 2A) is consistent with an anti-resistance role of other common mutations in pro-growth pathways such as the PTEN/PI3K/AKT pathway. Thus, it is believed that the constitutive activation of any pro-growth pathway by a mutation would make cancer cells unresponsive or much less responsive to the starvation- or IGF-I reduction-dependent protection.

The experiments discussed above were performed in medium containing 1% glucose and different concentrations of glucose. The effect of reducing the level of serum from the standard 10% to 1% on the toxicity of high-dose cyclophosphamide was also tested. Treatment with 15 mg/ml CP was toxic to primary glial cells in 10% serum but the switch to 1% serum caused a reduction in toxicity (FIG. 2B). By contrast, the same concentration of CP was as toxic to C6 glioma cells in 10% serum as it was in 1% serum (FIG. 2B).

In the *S. cerevisiae* experiments, it was showed that the deletion of SCH9/AKT protects whereas the constitutive activation of Ras2 ($RAS2^{val19}$) sensitizes the yeast cells to chemotherapy drugs. Since mammalian Ras and Akt are major signal transduction proteins downstream of the IGF-I receptor, and considering the role of the IGF-I pathway in regulating stress resistance, the effect of IGF-I and of an antibody against IGF-IR on DSR was also tested. It was reasoned that primary cells would respond to the IGF-1-inhibiting treatment by increasing stress resistance whereas cancer cells, which often express oncogenes that cause constitutive Ras and Akt activation, would not. Treatment with 100 ng/ml IGF-I (in the low IGF-I range for human adults) caused a 3-fold increase in the toxicity of cyclophosphamide to primary mixed glia but did not increase the toxicity of CP to C6 glioma cells (FIG. 2C). Furthermore, pre-incubation with an anti-IGF-IR antibody (aIR3) protected primary glia but not three glioma cell lines tested against CP toxicity (FIG. 2D). A similar sensitizing role of IGF-I was observed with primary rat cortical neurons but not the rat pheochromocytoma tumor PC12 cell line treated with oxidants (FIG. 12). These results in normal glia and in rat and human glioma and neuroblastoma cell lines are consistent with those in yeast cells and support the belief that short-term starvation and/or drugs that down-regulate IGF-IR/Ras/Akt signaling can protect normal cells much more effectively than cancer cells against chemotherapy. Notably, this differential stress resistance should apply to the great majority of pro-growth oncogenic mutations and not only to cancer cells with mutations in the Ras, Akt or Tor pathways. In fact, it worked with all the six cancer cell lines tested (FIG. 2), independently of the type of oncogenic mutations.

In an in vivo test, mice were treated with high dose chemotherapy in combination with STS and/or GH/IGF-I lowering strategies. For this purpose, etoposide, a widely used chemotherapy drug which damages DNA by multiple mechanisms and displays a generalized toxicity profile ranging from myelosuppression to liver and neurologic damage, was selected. Unusually high doses of etoposide (80-110 mg/kg) after a period of starvation, GH/IGF-I lowering treatment or both were administered. In humans, a third of this concentration of etoposide (30-45 mg/kg) is considered to be a high dose and therefore in the maximum allowable range.

To reduce GH/IGF-I mice were pre-treated for four days with the somatostatin analogue octreotide. This pre-treatment was followed by etoposide administration. A sub-group of mice were also starved for 48 hours (STS) before treatment with etoposide. The mice pre-treated with octreotide received this treatment for 4 additional days after chemotherapy. Whereas 80 mg/kg etoposide killed 43% of control (Eto, n=23, 2 experiments) and 29% of octreotide pre-treated mice (OCT/Eto, n=17), none of the mice treated with octreotide and also pre-starved for 48 hours died after 80 mg/kg etoposide treatment (Oct/STS/Eto/Oct, n=35) and only one of the mice that were only starved (STS/Eto, n=16) died after etoposide treatment (FIG. 7A). Remarkably, STS-octreotide pre-treated mice, which lost 20% of the weight during the 48 hours of starvation, regained all the weight in the four days after chemotherapy (FIG. 7B) whereas in the same period the control mice lost approximately 20% of the weight (FIG. 7B). Control mice treated with etoposide showed signs of toxicity including reduced mobility, ruffled hair and hunched back posture (FIG. 9B) whereas Oct/STS/Oct pre-treated mice showed no visible signs of stress or pain following etoposide treatment (FIG. 9A).

The effect of STS alone on the protection of mice of another genetic background (CD1) was also tested. To determine whether an extended STS strategy can be effective against a higher concentration of chemotherapy drugs 110 mg/kg etoposide was administered and the starvation period was also increased to 60 hours. Based on the experiments with oxidative stress, it was determined that this period is the maximum STS that provides protection. Longer starvation periods can weaken the animals and have the opposite effect. This concentration of etoposide killed all the control mice (Eto 110) but none of the STS pre-treated mice (STS/Eto 110, n=5) (FIG. 7C). As with the A/J mice, pre-starved CD1 mice lost 40% of the weight during the 60 hours of starvation but regained all the weight in the week after the etoposide treatment and showed no visible sign of toxicity (FIG. 7D).

The effect of the STS-based method was similar in athymic (Nude-nu) mice, which are widely used in cancer research because they allow the study of human tumors in the mouse model. Whereas 100 mg/kg etoposide killed 56% of the nude mice and all the mice co-treated with octreotide, none of the STS/Eto/Oct or STS/Eto treated mice (48-hour starvation) died (FIG. 7E). As observed with the other two genetic backgrounds, the pre-starved mice gained weight during the period in which the Eto-treated mice lost weight (FIG. 7F).

In summary, out of 70 mice from three genetic backgrounds that were starved before etoposide treatment, only one mouse in the STS only group and none of the mice in the STS/Oct group died (FIG. 7I). By contrast, out of the 63 mice treated with etoposide alone or etoposide and octreotide, 34 died of toxicity. These results are consistent with the yeast and glia/glioma data showing increased resistance to chemotherapy toxicity in response to starvation or low IGF-I. In mice, octreotide alone was not sufficient to protect against etoposide toxicity and virtually all the protection was due instead to STS. The discrepancy between the effect of IGF-I in vitro and octreotide in vivo may be due to the relatively modest effect of octreotide on the reduction of circulating IGF-I level.

To determine whether a much more severe reduction in IGF-I level than that achieved with octreotide can increase resistance to chemotherapy in vivo as was shown in vitro, the resistance against a high dose of cyclophosphamide of male and female LID mice, in which the liver IGF-I gene was conditionally deleted, resulting in a 75-90% reduced serum IGF-I concentration was studied. The LID mice treated with 500 mg/kg cyclophosphamide showed a remarkable improvement in resistance, with 30% mortality vs the 70% mortality for control mice (FIG. 7G, P<0.002). Furthermore, the LID mice lost an average of 10% of weight vs the 20% weight loss in control mice (FIG. 7H). The 70% surviving LID mice also did not show any signs of toxicity (FIG. 13B). Together with the in vitro results with IGF-I and anti-IGF-IR antibodies and the established role of starvation on the reduction of IGF-I levels, these data suggest that the inhibition of IGF-IR signaling mediates part of the effects of STS on resistance to chemotherapy in vivo. Notably, IGF-IR antibodies have been used successfully in a number of studies to reduce the growth or increase the death of cancer cells and are currently being evaluated in clinical trials.

To determine whether the differential stress resistance observed in yeast and mammalian cells would also occur in mice, the survival of mice injected with cancer cells was followed. A particularly aggressive tumor line (NXS2) that models neuroblastoma (NB), the most common extra cranial solid tumor, and the first cause of lethality in pre-school age children, was selected. Advanced NB patients, who represent approximately 50% of the cases, show metastatic dissemination at diagnosis, and have a long-term survival rate of only 20% in spite of aggressive chemotherapy with autologous hematopoietic stem cell support.

The NXS2 neuroblastoma line in mice induces consistent and reproducible metastases in a pattern which resembles the clinical scenario observed in neuroblastoma patients at advanced stages of disease. Experimental metastases in the liver, kidneys, adrenal gland, and ovaries were observed after 25-30 days of the inoculation with 200,000 NXS2 cells (Table 2) as previously described.

tially protection of cancer cells against etoposide. Based on these results, the use of STS alone would require several or many chemotherapy cycles to obtain toxicity to cancer cells comparable to that caused by high dose chemotherapy alone.

By contrast, none of the Oct/STS/Eto/Oct injected with NXS2 cells died until day 46, at a point when all the controls had died of cancer (FIG. 8, Table 2) (Gr. 4 vs. Gr. 1 p<0.0001). One mouse from this group survived until day 130. The survival of Oct/NXS2/STS/Eto/Oct mice was not statistically significantly different from that of NXS2/Eto and Oct/NXS2/Eto/Oct groups (Table 2) but, as described above, 50% of mice not protected with STS died of etoposide toxicity (FIGS. 7A and 8). Even if the initial etoposide-dependent death is not considered, the long-term survival of the octreotide/STS/NXS2/etoposide group was not significantly different from that of the NXS2/etoposide and significantly different but close to that of the Oct/NXS2/Eto/Oct group (FIG. 13). These results suggest that in combination with octreotide, STS protects the animal but not the cancer cells against chemotherapy.

Somatostatin analogues have been reported to promote anti-tumor activity through two distinct effects: direct actions, mediated by somatostatin receptors, and indirect actions, independent of the receptors. The somatostatin/octreotide receptor-mediated effect includes inhibition of cell cycle and growth factors effects, and induction of apoptosis. In contrast, the indirect effects comprise inhibition of the release of growth factors such as growth hormone and IGF-I.

To determine whether octreotide was acting directly on cancer cells, the toxicity of etoposide to NXS2 cells cultured in vitro in the presence or absence of octreotide was tested. Either 10 or 50 micromolar octreotide did not sensitize NXS2 cells to etoposide treatment suggesting that it is not increasing the survival of the NXS2 injected mice by directly sensitizing the cells to etoposide (FIG. 8B). Because of the many studies

TABLE 2

Frequency of metastases and survival in NXS2 injected mice (STS, Oct, Etoposide treatments) (Groups 1-8 represent the mice shown in FIG. 8A).

| Groups | N° mice | N° toxicity deaths | Liver | Kidneys | Ovaries | Adrenal gland | Hemorrhagic ascites | Median survival (days) | Survival Range (days) |
|---|---|---|---|---|---|---|---|---|---|
| Gr. 1 Control | 16 | 0/16 | 16/16 | 14/16 | 13/8 | 3/16 | 16/16 | 32 | 32-38 |
| Gr. 2 OCT | 8 | 0/8 | 8/8 | 8/8 | 8/8 | 2/8 | 8/8 | 33 | 31-37 |
| Gr. 3 OCT/STS/OCT | 8 | 0/8 | 8/8 | 5/8 | 6/8 | 1/8 | 8/8 | 31 | 27-33 |
| Gr. 4 OCT/STS/Eto/OCT | 8 | 0/8 | 8/8 | 8/8 | 6/8 | 0/8 | 6/8 | 56 | 46-130 |
| Gr. 5 OCT/Eto/OCT | 8 | 5/8 | 2/3* | 2/3* | 0/3* | 0/3* | 2/3* | 130* | 120-180 |
| Gr. 6 STS | 8 | 0/8 | 8/8 | 5/8 | 7/8 | 1/8 | 8/8 | 30 | 26-35 |
| Gr. 7 STS/Eto | 16 | 1/16 | 15/15 | 9/15 | 9/15 | 0/15 | 14/15 | 44 | 35-60 |
| Gr. 8 Eto | 6 | 3/6 | 3/3 | 3/3 | 0/3 | 0/3 | 3/3 | 130 | 87-140 |

A/J mice were i.v. inoculated with 200,000 NXS2 cells/mouse and treated as described in Experimental Procedures. All mice were followed until death and necropsies were performed. Only 3 mice from group 7 and 8 survived the initial etoposide treatment. The deaths caused by etoposide toxicity in the early days that occurred in groups 6, 7, 8 were not considered in the calculation of median survival. *1 mouse alive at 180 days.

The tumor development and survival of STS/Eto treated mice was significantly different from that of controls (Gr. 7 vs. Gr. 1 p<0.0001) (FIG. 8, Table 2) suggesting that STS alone provides strong protection to the mouse but only parshowing an anti-tumor growth and survival effect of lower GH and IGF-I or inhibition of the IGF-I and GH receptors, these results suggest that octreotide is improving long-term survival of STS treated mice by its well established role in decreasing GH and IGF-I levels, although other effects cannot be ruled out. Notably octreotide and other somatostatin analogues have been shown to have therapeutic effects in a number of cancer. In the absence of short-term starvation, octreotide alone did not protect mice against NXS2-dependent death (FIG. 8), suggesting that it is the synergism between etoposide and octreotide that is effective in killing tumor cells. These results also suggest that octreotide pretreatment before the injection of NXS2 cells does not affect the tumor growth.

The data above indicate that short-term starvation and/or reduction of IGF-I/IGF-IR signalling protects normal cells and mice but not a variety of cancer cells treated with chemotherapy drugs. While not wanting to be bound by the theory, it is believed that the basis for this is the existence of a "maintenance mode" which cells enter in response to starvation for the purpose of investing the remaining energy resources in protection of cells and tissues. In yeast, worms, and mice starvation or the genetic manipulation of starvation response pathways causes a major increase in protection against multiple stresses including heat shock and oxidative damage. In mammals, starvation causes a reduction in IGF-I levels which is associated with increased stress resistance. IGF-I is only one of the factors involved in the starvation response, but is among the major negative regulators of the entry into a stress resistant mode. In this study, it was showed that LID mice which have a dramatic reduction in circulating IGF-I are protected against chemotherapy toxicity, although the protection is not as effective as that provided by short-term starvation. Notably, in preclinical studies IGF-I lowering and IGF-IR targeting strategies have been shown to be effective in the treatment of multiple myelomas, prostate, breast and colon cancer in addition to other cancers. Thus, the combination of IGF-IR targeting and high dose chemotherapy should be an effective strategy to kill cancer cells, while preserving the health of the host.

Perhaps one of the most surprising findings of the present invention is the ability of mice of 3 different genetic backgrounds that have been starved for 48 hours to gain back the 20-40% weight that were lost during starvation even in the presence of doses of etoposide that cause a 20-30% weight loss and kill over 40% of the control mice. These mice also showed no visible sign of toxicity in response to doses of chemotherapy highly toxic to control animals. This high resistance to a drug that damages the DNA of dividing cells, particularly blood cells, would be consistent with the entry of most or all of the normally dividing cells into a high protection/cell cycle arrested mode in response to the 48-hour starvation. Since etoposide is rapidly excreted (up to 90% within 48 hours in humans), such "protective mode" may only need to last for a few days.

Chemotherapy treatment often relies mainly on one or a combination of several DNA damaging agents such as etoposide, cyclophosphamide, and doxorubicin. Although these agents are supposedly much more toxic to cancer cells than to normal cells, the in vitro studies show that cyclophosphamide, for example, can be as or more toxic to primary glial cells as it is to glioma cancer cells. This implies that the combination of multiple chemotherapy drugs causes massive damage to normal cells, especially at high doses. Notably, the differential stress resistance of mammalian cells to the alkylating agent cyclophosphamide by the starvation-response methods was less than 10-fold whereas starved yeast lacking SCH9/AKT reached a 1,000-10,000-fold higher resistance to menadione, hydrogen peroxide, MMS, and cyclophosphamide compared to RAS2$^{val19}$ expressing yeast cells (FIGS. 6 and 2). Furthermore, the 10,000-fold differential toxicity in yeast was obtained after only 30 minutes with hydrogen peroxide compared to the several days required for the differential toxicity of MMS or cyclophosphamide. Although toxic molecules such as hydrogen peroxide or menadione are not suitable for human cancer treatments, these results suggest that the selection of novel chemotherapy drugs in combination with DSR can result in a more rapid and effective toxicity to cancer cells. The ability to reach a 10,000-fold differential toxicity between cancer cells and normal human cells should lead to improved therapies for many cancers. Based on the results obtained with the aggressive NXS2 neuroblastoma line that was injected in mice it is reasonable to attempt to identify novel drugs and conditions that can yield a much greater differential toxicity to normal and cancer cells.

The method discussed above covers the use of any drug, protein, peptide, or molecule that inhibits any component of the growth hormone releasing hormone, growth hormone, growth hormone receptor, IGF-I, IGF-I receptor, Ras, Akt axis or inhibits other growth factors or growth factor receptors for the purpose of protecting normal human cells and human subjects but not (or less) cancer and other cells against chemotherapy, radiotherapy, cancer treatment, or any other toxic treatment or environment.

References

1. Holzenberger, M. et al. IGF-I receptor regulates lifespan and resistance to oxidative stress in mice. Nature 421, 182-7 (2003).

2. Lithgow, G. J., White, T. M., Melov, S. & Johnson, T. E. Thermotolerance and extended life-span conferred by single-gene mutations and induced by thermal stress. Proc. Natl. Acad. Sci. USA 92, 7540-4 (1995).

3. Longo, V. & Finch, C. E. Evolutionary medicine: from dwarf model systems to healthy centenarians? Science 299, 1342-6 (2003).

4. Migliaccio, E. et al. The p66shc adaptor protein controls oxidative stress response and life span in mammals. Nature 402, 309-13 (1999).

5. Fabrizio, P. et al. SOD2 Functions Downstream of Sch9 to Extend Longevity in Yeast. Genetics 163, 35-46 (2003).

6. Fabrizio, P., Pozza, F., Pletcher, S. D., Gendron, C. M. & Longo, V. D. Regulation of longevity and stress resistance by Sch9 in yeast. Science 292, 288-90 (2001).

7. Pollak, M. N., Schernhammer, E. S. & Hankinson, S. E. Insulin-like growth factors and neoplasia. Nat Rev Cancer 4, 505-18 (2004).

8. Harper, J. M. et al. Stress resistance and aging: influence of genes and nutrition. Mech Ageing Dev 127, 687-94 (2006).

9. Hanahan, D. & Weinberg, R. A. The hallmarks of cancer. Cell 100, 57-70 (2000).

10. Bruce-Keller, A. J., Umberger, G., McFall, R. & Mattson, M. P. Food restriction reduces brain damage and improves behavioral outcome following excitotoxic and metabolic insults. Ann Neurol 45, 8-15 (1999).

11. Fabrizio, P. et al. Sir2 blocks extreme life-span extension [see comment]. Cell 123, 655-67 (2005).

12. Kaeberlein, M. et al. Regulation of yeast replicative life span by TOR and Sch9 in response to nutrients [see comment]. Science 310, 1193-6 (2005).

13. Lin, S. J., Defossez, P. A. & Guarente, L. Requirement of NAD and SIR2 for life-span extension by calorie restriction in *Saccharomyces cerevisiae*. Science 289, 2126-8. (2000).

14. Timms, A. R., Muriel, W. & Bridges, B. A. A UmuD, C-dependent pathway for spontaneous G:C to C:G transversions in stationary phase *Escherichia coli* mutY. Mutat Res 435, 77-80 (1999).

15. Poole, C. J. et al. Epirubicin and cyclophosphamide, methotrexate, and fluorouracil as adjuvant therapy for early breast cancer. N Engl J Med 355, 1851-62 (2006).

16. Brown-Borg, H. M., Rakoczy, S. G., Romanick, M. A. & Kennedy, M. A. Effects of growth hormone and insulin-like growth factor-I on hepatocyte antioxidative enzymes. Exp Biol Med 227, 94-104. (2002).

17. Manetta, J. et al. Effect of training on the GH/IGF-I axis during exercise in middle-aged men: relationship to glucose homeostasis. Am J Physiol Endocrinol Metab 283, E929-36 (2002).

18. Grunberg, S. M. Cyclophosphamide and etoposide for non-small cell and small cell lung cancer. Drugs 58 Suppl 3, 11-5 (1999).

19. Mistry, A. R. et al. DNA topoisomerase II in therapy-related acute promyelocytic leukemia. N Engl J Med 352, 1529-38 (2005).

20. Vinolas, N., Graus, F., Mellado, B., Caralt, L. & Estape, J. Phase II trial of cisplatinum and etoposide in brain metastases of solid tumors. J Neurooncol 35, 145-8 (1997).

21. Kroger, N. et al. Busulfan, cyclophosphamide and etoposide as high-dose conditioning therapy in patients with malignant lymphoma and prior dose-limiting radiation therapy. Bone Marrow Transplant 21, 1171-5 (1998).

22. Gronbaek, H. et al. Inhibitory effects of octreotide on renal and glomerular growth in early experimental diabetes in mice. J Endocrinol 172, 637-43 (2002).

23. Hunter, S. J. et al. Comparison of monthly intramuscular injections of Sandostatin LAR with multiple subcutaneous injections of octreotide in the treatment of acromegaly; effects on growth hormone and other markers of growth hormone secretion. Clin Endocrinol (Oxf) 50, 245-51 (1999).

24. Yakar, S. et al. Normal growth and development in the absence of hepatic insulin-like growth factor I. Proc Natl Acad Sci USA 96, 7324-9 (1999).

25. Ngo, T. H., Barnard, R. J., Tymchuk, C. N., Cohen, P. & Aronson, W. J. Effect of diet and exercise on serum insulin, IGF-I, and IGFBP-1 levels and growth of LNCaP cells in vitro (United States). Cancer Causes Control 13, 929-35 (2002).

26. Maccario, M. et al. Effects of 36-hour fasting on GH/IGF-I axis and metabolic parameters in patients with simple obesity. Comparison with normal subjects and hypopituitary patients with severe GH deficiency. Int J Obes Relat Metab Disord 25, 1233-9 (2001).

27. De Bernardi, B. et al. Disseminated neuroblastoma in children older than one year at diagnosis: comparable results with three consecutive high-dose protocols adopted by the Italian Co-Operative Group for Neuroblastoma. J Clin Oncol 21, 1592-601 (2003).

28. Matthay, K. K. et al. Treatment of high-risk neuroblastoma with intensive chemotherapy, radiotherapy, autologous bone marrow transplantation, and 13-cis-retinoic acid. Children's Cancer Group. N Engl J Med 341, 1165-73 (1999).

29. Lode, H. N. et al. Targeted interleukin-2 therapy for spontaneous neuroblastoma metastases to bone marrow. J Natl Cancer Inst 89, 1586-94 (1997).

30. Zalatnai, A. & Schally, A. V. Treatment of N-nitrosobis(2-oxopropyl)amine-induced pancreatic cancer in Syrian golden hamsters with D-Trp-6-LH-RH and somatostatin analogue RC-160 microcapsules. Cancer Res 49, 1810-5 (1989).

31. Susini, C. & Buscail, L. Rationale for the use of somatostatin analogs as antitumor agents. Ann Oncol 17, 1733-42 (2006).

32. Hejna, M., Schmidinger, M. & Raderer, M. The clinical role of somatostatin analogues as antineoplastic agents: much ado about nothing? Ann Oncol 13, 653-68 (2002).

33. McPherson, A., Jr. The growth and preliminary investigation of protein nucleic acid crystals for x-ray diffraction analysis. Met. Biochem. Anal. 23, 249-345 (1976).

EXAMPLE III

Materials and Methods

Yeast strains and Growth Conditions. All the experiments were performed using yeast of DBY746 background. Knockout strains were prepared with standard PCR-mediated gene disruption protocol. Strains used in this study:

| Strain | Genotype |
|---|---|
| DBY746 | MATa, leu2-3, 112, his3Δ1, trp1-289, ura3-52, GAL+ |
| sch9/aktΔ | DBY746 sch9::URA3 |
| ras2Δ | DBY746 ras2::LEU2 |
| tor1Δ | DBY746 tor1::HIS3 |
| RAS2$^{val19}$ | DBY746 RAS2$^{val19}$ (CEN, URA3)* |
| tor1ΔRAS2$^{val19}$ | DBY746 ras2::LEU2 RAS2$^{val19}$ (CEN, URA3)* |
| sch9/aktΔRAS2$^{val19}$ | DBY746 sch9::URA3 RAS2$^{val19}$ (CEN, URA3)* |
| SCH9/AKT | DBY746 SCH9 (CEN, URA3)* |

*pRS416-RAS2$^{val19}$ was constructed by inserting 1.9 kb ClaI-HindIII fragment from pMF100 into pRS416.

Yeast cells were grown in minimal medium (SC) containing 2% glucose and supplemented with amino acids as described previously. For short term starvation (STS) treatment, day 1 cultures (24 hours after initial OD=0.1 inoculation) were washed 3 times with sterile distilled water, resuspended in water, and incubated at 30° C. with shaking for 48 hours (day 3).

Yeast Oxidative stress assay. For oxidative stress resistance assays, day 3 cells were diluted to an $OD_{600}$ of 1 in K-phosphate buffer, pH 7.4, and treated with 0.2-1 mM menadione for 1 hour. Alternatively, cells were diluted to an $OD_{600}$ of 1 in K-phosphate buffer, pH 6 and treated with 200-400 mM of hydrogen peroxide for 30 minutes. Serial dilutions of untreated and treated cells were spotted onto YPD plates and incubated at 30° C. for 2-3 days.

Yeast viability assay. Overnight SDC cultures were diluted to $OD_{600}$ 0.1 into fresh SDC medium. After 24 hours (day 1), the appropriate strains were mixed 1:1 based on $OD_{600}$ ($OD_{600}$ of 10 each) and incubated for 2 hours at 30° C. with shaking. The mixed cultures were then treated with either cyclophosphamide (CP, 0.1 M) or methyl methanesulfonate (MMS, 0.01%, Sigma). MMS was prepared in ddH$_2$0 from stock solution and was diluted directly into the mixed culture to a final concentration of (v/v) 0.01%. However, due to the high concentration of CP (0.1 M) required, CP crystals were dissolved directly into the medium. To do so, mixed cultures were centrifuged for 5 minutes at 2,500 rpm and the media was collected, in which CP crystals were dissolved to a concentration of 0.1 M. The mixed culture was then resuspended in the CP-containing medium. Viability was measured as colony-forming units (CFUs) every 24 hours by plating onto appropriate selective media. Viability of individual strains was measured using the same method as for the mixed cultures. Relative survival shown was determined by the percentage of the ratio between the treated and untreated (control) cells.

Cell culture experiments. Primary mixed glial cells were obtained from the cerebral cortices of 1 to 3 day old Sprague Dawley rat pups (Charles River) as described before. Cells cultured for 10-14 days in DMEM/F12 medium (Invitrogen) with 10% fetal bovine serum (FBS) were used in assays. Primary neurons from embryonic day 18 Sprague-Dawley rat cerebral cortices were dissociated in neurobasal medium (Invitrogen) supplemented with 0.5 mM L-glutamine, 25 μM L-glutamic acid and 2% B-27 and plated at 640 cells/mm$^2$ in 96-well plates which were pre-coated with 10 microg/ml poly-D-lysine dissolved in Borax buffer (0.15 M, pH 8.4). Neurons were maintained at 37° C. in 5% $CO_2$ in neurobasal medium supplemented with B-27 and 0.5 mM L-glutamine for 4 days.

C6, A10-85, 9L and RG2 rat glioma cell lines and LN229 human glioma cell line, and SH-SY5Y human neuroblastoma cell line were maintained in DMEM/F12 medium with 10% PBS and the PC12 rat pheochromocytoma cell line (ATCC) was maintained in F12K medium supplemented with 15% horse serum and 2.5% fetal bovine serum at 37° C. under 5% $CO_2$.

STS Treatments of mammalian cells. Primary glia, glioma or neuroblastoma cells were seeded into 96-well microtiter plates at 20,000-30,000 cells/well and incubated for 2 days. Cells were washed with phosphate buffered saline (PBS) prior to treatments as indicated in the text. All treatments were performed at 37° C. under 5% $CO_2$.

Glucose restriction was done by incubating cells in glucose free DMEM (Invitrogen) supplemented with either low glucose (0.5 g/L) or normal glucose (1.0 g/L) for 24 hours. Serum restriction was done by incubating cells in DMEM/F12 with either 10% or 1% FBS for 24 hours. IGF-I treatment was carried out by incubating cells for 48 hours in DMEM/F12 with 1% FBS and rhIGF-I (100 ng/ml, ProSpec-Tany TechnoGene, Rehovot, Israel), which is shown to be within the IGF-I level range for middle age humans. To antagonize IGF-I receptor activity, cells were incubated with neutralizing monoclonal anti-IGF-1R antibody (αIR3, 1 microg/ml; Calbiochem) in DMEM/F12 1% FBS for 24 hours.

In vitro drug treatments. Cyclophosphamide (CP, Sigma) was used for in vitro chemotherapy studies. CP was prepared in DMEM/F12 with 1% FBS at 40 mg/ml and was filter sterilized. The stock solution was stored at 4° C. for no longer than 2 weeks. Following STS treatments, cells were incubated with varying concentrations of cyclophosphamide (6-15 mg/ml) for 10 hours in DMEM/F12 with 1% FBS. Glial cells have been reported to express cytochrome P450 and thus capable of metabolizing the prodrug cyclophosphamide. Cytotoxicity was measured by either lactate dehydrogenase released using the CytoTox 96 Non-Radioactive Cytotoxicity Assay kit (Promega) or the ability to reduce methylthiazolyl-diphenyl-tetrazolium bromide (MTT). LDH released into the medium by lysed cells were measured with a 10-minute enzymatic assay that converts a tetrazolium salt (INT) into a red formazan product. A 96-well based calorimetric assay measured the amount of the red formazan formed, which is proportional to the number of dead cells. % LDH release was determined with reference to the maximum and background LDH release of control cells.

MTT is reduced in the mitochondria (metabolically active cells) by mitochondrial reductase enzymes to form insoluble purple formazan crystals, which are solubilized by the addition of a detergent. Briefly, MTT was prepared at 5 mg/ml in PBS and was diluted in DMEM/F12 1% FBS media to a final concentration of 0.5 mg/ml for assays. Following experimental treatments, media was replaced with 100 μl of MTT and was incubated for 3-4 hours at 37° C. Formazan crystals were dissolved overnight (16 hours) at 37° C. with 100 μl lysis buffer ((w/v) 15% SDS, (v/v) 50% dimethylformamide). MTT assay results were presented as percentage of MTT reduction level of treated cells to control cells. Absorbance was read at 490 nm and 570 nm for LDH and MTT assays respectively using a microplate reader SpectraMax 250 (Molecular Devices) and SoftMax Pro 3.0 software (Molecular Devices).

NXS2 neuroblastoma cells treated with different concentrations of etoposide (1-3 μM) in presence or absence of octreotide (10 and 50 μM) for 72 hours were harvested by scraping, washed with complete medium, and incubated with trypan blue (0.04%; Sigma; St. Louis, Mo.) for 1 minute at 37° C. The cells were then placed in a Burker chamber (Tecnovetro, Monza Milan, Italy) and counted by viewing with a contrast phase microscope (Olympus Optical Co LTD, Tokyo, Japan). Trypan blue-positive cells (i.e., dead cells), trypan blue-negative cells (i.e., living cells), and total cells were counted per microscope field at ×100 magnification (four fields were counted for each treatment). The proportion of dead (or living) cells was calculated by dividing the number of dead (or living) cells by the total number of cells per field.

Primary rat neurons and PC12 cells were treated with IGF-1 and paraquat to determine the effect of IGF-1 on oxidative stress. Cortical neurons were treated for 24 hours in Eagle's minimal essential medium (Invitrogen) supplemented with 21 mM glucose and 1% horse serum. PC12 cells were plated at $5 \times 10^4$ cells/well onto poly-D-lysine coated 96-well plates and were grown for 24 hours in F12K 1% HS. Both types of cells were then treated with either 100 μM of paraquat, IGF-1 (100 ng/ml) followed 30 minutes later by paraquat (100 μM) or IGF-1 (100 ng/ml) alone in appropriate media. Survival was determined by the MTT assay and presented as percent ratio of treated to control.

Statistical analyses were performed using GraphPad Prism 4 software (GraphPad Software).

Western blots. Cells were seeded at $2 \times 10^6$ cells/well in a 6-well culture plate and cultured in DMEM/F12 10% FBS for 1 day. Cells were washed with PBS twice and glucose and serum starved by incubating in glucose-free DMEM for 16 hours, followed by 1 hour of 10% FBS treatment or 1 additional hour of starvation. Western blots were performed as previously described with some modifications. Briefly, cells were lysed with 100 μl of RIPA lysis buffer with phosphatase and protease inhibitors (50 mM Tris HCl pH8, a 50 mM NaCl, 1% NP-40, 0.5% sodium deoxycholate, 0.1% SDS, 1 mM orthovanadate, 10 mM NaF, protease inhibitors (Sigma)). Protein concentration was measured to normalize protein loading using the BCA protein assay. Adjusted amounts of protein was loaded and separated by SDS-PAGE (12%) and transferred onto PVDF membrane (Millipore, Mass.). Membranes were dried overnight and blocked for 1 hour with TBS-T+BSA followed by a 1-hour incubation with anti-phospho-ERK (Sigma) and signal was detected using enhanced chemiluminescence (Amersham).

In vivo therapeutic studies in mice. The murine NX3IT28 cell line was generated by hybridization of the GD2-negative C1300 murine neuroblastoma cell line (A/J background) with murine dorsal root ganglional cells from C57BL/6J mice, as previously described. The NXS2 subline was then created by the selection of NX3IT28 cells with high GD2 expression.

Six-to-seven-week-old female A/J mice, weighing 15-18 g were purchased from Harlan Laboratories (Harlan Italy, S. Pietro al Natisone, Italy) and housed in sterile enclosures under specific virus and antigen-free conditions. All procedures involving mice and their care were reviewed and approved by licensing and ethical committee of the National Cancer Research Institute, Genoa, Italy, and by the Italian Ministry of Health. A/J mice were pretreated with 1 mg/kg/day doses of human octreotide (OCT, ProSpec-Tany Techno-Gene, Rehovot, Israel) for 4 days given slowly through the tail vein in a volume of 100 μl and then injected intravenously with murine neuroblastoma NXS2 cell line (200,000/mouse), as previously described. After tumor cell injection, some groups of animals were starved for 48 hours and then i.v. treated with 80 mg/kg of Etoposide Teva (Teva Pharma B.V., Mijdrecht, Holland), administered as a single dose. Additional daily doses of OCT were administered for 4 days after chemotherapy. Control groups of mice without diet starvation and OCT treatment were also investigated.

Octreotide pre-treatment: 4 days 1 mg/kg/day
NXS2: 200,000/mouse on day 4
STS: from day 4 to day 6 (after tumor cell injection)
Etoposide: 80 mg/kg on day 7
Octreotide post-treatment: days 8-11

To determine toxicity and efficacy, mice were monitored routinely for weight loss and general behavior. The animals were killed by cervical dislocation after being anesthetized with xilezine (Xilor 2%, Bio98 Srl, Milan, Italy) when they showed signs of poor health, such as adbominal dilatation, dehydration, or paraplegia. Survival time was used as the main criterion for determining the efficacy of each treatment.

The statistical significance of differential survival between experimental groups of animals was determined by Kaplan-Meier curves and log-rank (Peto) test by the use of StatDirect statistical software (CamCode, Ashwell, UK).

In some experiments, four-week-old female CD1 mice (Harlan), weighing 18-20 g were used to evaluate stress resistance after 60-hour diet starvation. These animals, i.v. injected with 110 mg/kg etoposide, were monitored routinely for weight loss and general behavior. Survival time was used as the main criterion for determining the differential stress resistance after short-term starvation.

In other experiments, four-week old female athymic (Nude-nu) mice (Harlan), weighing 20-22 gr were used to evaluate stress resistance after a 48-hour starvation. These animals were i.v.—injected with 100 mg/Kg etoposide and then monitored routinely for weight loss and general behavior. Survival time was used as the main criterion for determining the resistance to high-dose chemotherapy after short-term starvation.

Thirty-four to forty-two-week old LID and their control L/L⁻ mice were used to evaluate the role of circulating liver-derived IGF-I in stress resistance. LID and L/L⁻ mice were generated using the Cre/loxP system as described before. Briefly, albumin-cre transgenic mice were crossed with mice homozygous for exon4 of the igf-1 gene flanked with two loxP sites (L/L), therefore generating mice deficient in producing hepatic IGF-I. L/L⁻ mice have exon4 of the igf-1 gene flanked by loxP sites and produce normal hepatic IGF-I levels while LID mice show 75% lower circulating IGF-I levels. All mice were individually caged throughout the experiment and had access to food and water ad libitum. Both LID and L/L⁻ mice were each injected 500 mg/kg of cyclophosphamide i.p. using 29G insulin syringes. Cyclophosphamide was prepared in saline at 40 mg/ml and warmed prior to injection. Mice were routinely monitored for weight loss and signs of pain and stress. Survival time was the main criterion for determining the effect of low circulating IGF-I on the resistance to high-dose cyclophosphamide. The statistical significance of differential survival between experimental groups was determined by Kaplan-Meier curves and log-rank test using GraphPad Prism 4 software (San Diego, Calif.).

References

1. Brachmann, C. B. et al. Designer deletion strains derived from *Saccharomyces cerevisiae* S288C: a useful set of strains and plasmids for PCR-mediated gene disruption and other applications. Yeast 14, 115-32 (1998).

2. Morano, K. A. & Thiele, D. J. The Sch9 protein kinase regulates Hsp90 chaperone complex signal transduction activity in vivo. Embo J 18, 5953-62 (1999).

3. Fabrizio, P. et al. Sir2 blocks extreme life-span extension. Cell 123, 655-67 (2005).

4. McCarthy, K. D. & de Vellis, J. Preparation of separate astroglial and oligodendroglial cell cultures from rat cerebral tissue. J Cell Biol 85, 890-902 (1980).

5. Hansen, M. B., Nielsen, S. E. & Berg, K. Re-examination and further development of a precise and rapid dye method for measuring cell growth/cell kill. Journal of Immunological Methods 119, 203-10 (1989).

6. Yung, H. W. & Tolkovsky, A. M. Erasure of kinase phosphorylation in astrocytes during oxygen-glucose deprivation is controlled by ATP levels and activation of phosphatases. J Neurochem 86, 1281-8 (2003).

7. Greene, L. A. et al. Neuronal properties of hybrid neuroblastoma X sympathetic ganglion cells. Proc Natl Acad Sci USA 72, 4923-7 (1975).

8. Lode, H. N. et al. Targeted interleukin-2 therapy for spontaneous neuroblastoma metastases to bone marrow. J Natl Cancer Inst 89, 1586-94 (1997).

9. Yakar, S. et al. Normal growth and development in the absence of hepatic insulin-like growth factor I. Proc Natl Acad Sci USA 96, 7324-9. (1999).

10. Kempermann, G., Knoth, R., Gebicke-Haerter, P. J., Stolz, B. J., Volk, B. Cytochrome P450 in rat astrocytes in vivo and in vitro: Intracellular localization and induction by phenyloin. J Neurosci Res 39, 576-88 (1994).

11. Geng, J., Strobel, H. W. Expression, induction and regulation of the cytochrome P450 monooxygenase system in the rat glioma C6 cell line. Brain Res 784, 276-83 (1998).

EXAMPLE IV

Oncogene Homologs and the Regulation of Stress Resistance and Aging in Lower Eukaryotes The studies in *S. cerevisiae* and those in worms, flies, and mice have uncovered a strong association between life span extension and resistance to multiple stresses. A remarkable resistance to multiple stresses including chemotherapy drugs and oxidants in long-lived yeast cells lacking pro-growth proteins including the orthologs of the human Ras (RAS2) and Akt (SCH9/AKT) proto-oncogenes was observed (FIG. 15). Both Ras and Akt are among the signal transduction proteins most frequently found in a constitutively activated form in human cancers. Stress resistance is also associated with long-lived worms and mice with reduced activity of homologs of the IGF-I receptor (IGF-IR), which functions upstream of Ras and Akt in mammalian cells. This resistance is also observed in calorie restricted model systems in which the calorie intake is reduced by 30 to 100%.

The discovery of the role of Ras2 and Sch9/Akt in the negative regulation of stress resistance together with the association between mutations that activate IGF-IR, Ras or Akt and many human cancers prompted the hypothesis that normal but not cancer cells would respond to starvation or downregulation of growth hormone (GH)/IGF-I signaling by entering a chemotherapy resistance mode. In fact, one of the major phenotypic characteristics of malignant cells is the ability to grow or remain in a growth mode even in the absence of growth factors, in part provided by the hyper- or constitutive activation of pathways including those regulated by IGF-IR, Ras and Akt.

There are many similarities between long-lived mutants in *S. cerevisiae, C. elegans, Drosophila*, and mice and many of the genes implicated in life span regulation are also frequently found in mutated oncogenic forms in cancer cells. *C. elegans* age-1 and daf-2 mutations extend the life-span in adult organisms by 65 to 100% by decreasing AKT-1/AKT2 signaling and by activating transcription factor DAF-16. These changes are associated with the induction of superoxide dismutase (MnSOD), catalase, and HSP70. In previous work it was showed that the inactivation of the Ras/cAMP/PKA pathway in *S. cerevisiae* increases longevity as well as resistance to oxidative and thermal stress in part by activating transcription factors Msn2 and Msn4, which induce the expression of genes encoding for several heat shock proteins, catalase (CTT1), and the DNA damage inducible gene DDR2. MnSOD also appears to be regulated in a similar manner. Previous results also suggest that the effects of sch9/akt deletion on stress resistance and life span require the serine threonine kinase Rim15 and transcription factor Gis1. In worms, SMK-1 functions downstream of DAF-16, to regulate UV and oxidative stress but not thermal stress. Thus, the yeast Ras/Cyr1/PKA/Msn2/4 and Sch9/Rim15/Gis1 and the *C. elegans* DAF-2/AGE-1/AKT/DAF16 pathways play similar roles in regulating longevity and multiple stress-resistance systems. Similarly, in *Drosophila*, mutations in the insulin receptor/Akt/PKB pathway extend longevity and a mutation in the G-protein coupled receptor homolog MTH causes a 35% life span extension and increases resistance to starvation and paraquat toxicity. Life span is also extended by potential downstream mediators of starvation-responses such as the Indy gene.

Whereas the inactivation of these partially conserved pro-aging pathways increases resistance to oxidative stress in lower eukaryotes, the constitutive activation of analogous pathways is known to promote cancer. One object is to test whether the inactivation of the Ras and Sch9/Akt pathways in *S. cerevisiae* by either deletion mutations or starvation increases resistance to a range of chemotherapy drugs, including alkylating agents, topoisomerase inhibitors, and oxidants. Furthermore, another object is to test whether the overexpression of the oncogene-like RAS2 or SCH9/AKT genes can reverse the resistance of mutated or starved yeast to chemotherapy drugs. In addition to testing the range and mechanisms of DSR in *S. cerevisiae*, another object is to characterize the DNA damage caused by different categories of chemotherapy drugs and study the mechanisms responsible for the effect of Ras and Sch9/Akt on the resistance to chemotherapy. The understanding of the mechanisms of DSR in yeast is important because it provides the foundation for the development of an analogous method that can be applied to killing cancer but not normal mammalian cells.

Oncogene Homologs and the Regulation of Stress Resistance in Mammals

The inactivation of signal transduction pathways implicated in cancer has also been shown to increase resistance to stress and survival in mammals. The deletion of the p66$^{SHC}$ gene, associated with Ras, increases resistance to paraquat and hydrogen peroxide and extends survival by 30% in mice. Mutations that cause either a deficiency in the level of plasma growth hormone (GH) and IGF-I or a reduction of IGF-I signaling cause an up to 50% increase in life span. As observed in long-lived lower eukaryotes, the activities of antioxidant enzymes superoxide dismutases and catalase are decreased in murine hepatocytes exposed to GH or IGF-I and in transgenic mice overexpressing GH. In rats, IGF-I attenuates cellular stress response and the expression of stress response proteins HSP72 and hemeoxygenase. IGF-I is a polypeptide involved in many aspects of growth and development. IGF-I is generated mainly in the liver and is found in the blood in a stable complex with IGF-I binding proteins. Homozygous Ames dwarf mutations in the Prop-1 gene (df/df) prevent the generation of the anterior pituitary cells that produce growth hormone (GH), thyroid stimulating hormone, and prolactin. df/df young adult mice are approximately one third of the size of control mice but survive >50% longer than controls. This effect of dwarf mutations on life span appears to be caused by the absence of plasma GH, which stimulates the secretion of IGF-I from liver cells by activating the hepatic GH receptors. In fact, IGF-I is reduced dramatically in the plasma of df/df mice. The plasma GH deficiency appears to mediate the effects of Prop-1 and Pit-1 mutations on longevity, since the mice that cannot release GH in response to growth hormone releasing hormone also live longer. Furthermore, dwarf mice with high plasma GE, but a 90% lower IGF-I (GHR/BP null mice) live longer than the wild type mice. Taken together these studies suggest that the reduction in plasma IGF-I is responsible for a major portion of the life span increase in dwarf, GH deficient, and GHR/BP null mice.

A recent study shows that deletion of the IGF-I gene exclusively in the liver (IGF-I/loxP) causes a dramatic reduction of plasma IGF-I, but does not result in growth and development defects suggesting that GH can affect cellular function and the autocrine/paracrine release of IGF-I in various tissues independently of plasma IGF-I. In fact, IGF-I mRNA expression is normal in fat cells, muscle, kidney, heart and spleen of IGF-I/loxP mice. Mutations that decrease the activity of the adenylyl cyclase/cAMP/PKA pathway and increase life span and stress resistance were identified. Recently, a reduction in adenylyl cyclase activity by deletion of the 5 adenylyl cyclase (AC5) gene was shown to extend life span and also increase resistance to oxidative stress in mice, suggesting that the role of both the Akt and cAMP/PKA pathways in the regulation of aging and stress resistance may be conserved from yeast to mice (FIG. 15). The mammalian IGF-1 receptor activates both Akt/PKB and Ras and analogously to yeast Sch9/Akt and Ras, regulates glucose metabolism and cellular proliferation. Many studies, implicate increased IGF-I or IGF-I signaling as a risk factor in a variety of cancers, suggesting that this pro-mitotic pathway can promote both aging but also the conditions necessary for cancer. Another object is to test whether reduced glucose, serum, and/or IGF-I can protect primary mammalian cells but not, or less, rodent and human cancer cells against different chemotherapy drugs.

Caloric Restriction, Dwarf Mice, and IGF-I

The chronic reduction of calories by 10-40% below ad lib intake slows aging and extends life span in lab rodents. CR decreases age-related pathologies including tumors and kidney degeneration, lowers blood glucose, IGF-I, and insulin, and elevates corticosterone (Table 3). CR also causes a reduction in oxidative modifications of long-lived macromolecules such as collagen and affects age-related changes in the brain: it slows the loss of dopamine receptors and attenuates the degeneration of spinal motoneurons in rats. Although the mechanism responsible for the effects of CR is unknown, it may involve a decrease in the levels of circulating Insulin-like Growth Factor 1 (IGF-I). The results in yeast indicate that the reduction of Ras-cAMP-PKA and Sch9/Akt signaling plays an important role in the effect of calorie restriction/starvation on stress resistance and aging (FIG. 17). In fact, CR mice and dwarf mice, with IGF-I signaling deficiency, share several characteristics (compared to ad lib controls):

TABLE 3

Similarities between caloric restricted and dwarf mice

| CR | | Ames dwarf |
|---|---|---|
| Body weight (young) | reduced | reduced |
| Plasma glucose | reduced | reduced |
| Plasma Insulin | reduced | reduced |
| Body temperature | reduced | reduced |
| Plasma IGF-I | reduced | absent |
| Corticosterone | elevated | elevated |
| Life span | extended | extended |

Starvation Response in Mammals

The DSR method is based on the ability of starvation to protect normal but not, or less, cancer cells against high dose chemotherapy. However, the use of starvation to protect cancer patients that often have already lost much weight would have limited applications. Therefore, it is important to identify factors that can mimic the effect of starvation on protection. In the results the effect of the somatostatin analog octreotide in DSR were tested but found to be ineffective in the protection against the chemotherapy drug etoposide but effective in the enhancement of the toxicity to cancer cells but not normal cells after starvation. In other words, octreotide did not protect mice against etoposide, but reverse the effect of starvation in the protection of cancer cells but not normal cells. The explanation for these results is complex. In fact, the level of somatostatin, which inhibits the release of growth hormone from the pituitary, was found to be reduced by 70% after a 3-day fasting period (rats) but a 24-72-hour starvation inhibits GH secretion, although this effect may not depend on somatostatin. In humans, a 48-hour starvation raises GH levels and does not increase IGF-I level. This effect may be the result of a major increase in the IGF-I inhibitory protein IGFPB-1, which may decrease IGF-I bioavailability and consequently prevent the feedback inhibition of GE secretion by IGF-I. However, a longer starvation (5 days) does decrease the level of IGF-I in humans. Thus, the decrease in the pro-growth IGF-I by long-term starvation may contribute to the effect of starvation in the protection against high dose chemotherapy but somatostatin administration alone is not sufficient for protection. Another object is to study further the effect of different periods of starvation on the level of IGF-I and IGF-I binding proteins in mice. These studies are important for identifying the factors and mechanisms that mediate the effect of starvation on resistance to chemotherapy.

Self-sufficiency in Growth Signals and Insensitivity to Anti-growth Signals in Cancer Cells Two of the major "alterations in cell physiology that dictate malignant growth" are: 1) self-sufficiency in growth signal, 2) insensitivity to anti-growth signals. In fact, the great majority of normal cells are unable to grow in the absence of growth factors, whereas cancer cells express oncogenes that mimic the effect of growth factors. Such "independence" can be caused by changes in extracellular factors that promote growth, the activation of membrane receptors, or mutations that lead to the activation of intracellular signal transduction proteins. Some of the extracellular factors overproduced by cancer cells include TGF, PDGF and IGF-I. Among the receptors overexpressed in a number of carcinomas are the EGF and HER-2 receptors. Extracellular matrix receptors that can promote growth, known as integrins, are also found to be activated in cancer cells. Perhaps the most important contribution to the "growth factors independence of cancer cells" comes from intracellular pathways, particularly the Ras/Raf/MAPK and the PTEN/PI3K/AKT pathways. Altered forms of Ras that can render the cell growth independent from extracellular growth signals are found in approximately a quarter of all cancers and half of colon cancers (FIG. 16). The link between Ras and PI3K may further stimulate growth and also activate anti-apoptotic pathways.

Another highly relevant feature of cancer cells is the ability to "disobey" anti-growth orders. These orders are often focused on the block of the progression through the G1 phase of the cell cycle. The retinoblastoma protein (Rb) is one of the central negative regulators of proliferation in normal cells. When bound to transcription factor E2F, Rb prevents the induction of many pro-growth genes. One of the major regulators of Rb and the anti-proliferation mode is the signaling protein TGF-beta, which can block the phosphorylation that causes the inactivation of Rb. Cancer cells can become insensitive to anti-growth signals in many ways including the down-regulation of the TGF-beta receptor or through mutations that cause the inactivation of Rb.

The "self-sufficiency in growth signals and insensitivity to anti-growth signals" features of cancer cells and the central roles of Ras and Akt in oncogenesis (FIG. 16) are central to the belief that normal but not cancer cells will enter a protective mode in response to starvation or to the inhibition of growth factor signaling and in particular IGF-I. Based on the conserved entry into a "stress resistance" mode in response to starvation or anti-growth signals in model systems ranging from yeast to mice, it is believed that all normal cells can enter a state in which they are protected or partially protected against chemotherapy, although it is not yet known how effective this protection will be. By contrast, the "self-sufficient" cancer cells should disobey or partially disobey the "stress resistance orders" and continue on their pro-growth path. IGF and IGFBP alterations in animal models of cancer Transgenic mice that develop prostate tumors show an IGF axis disturbance very similar in their behavior to the human disease. It has been shown that TRAMP mice have IGF-I and IGF-IR alterations similar to those proposed in the human disease. Similar findings have been demonstrated in the Myc-over-expressing mouse model. Additionally, it has been demonstrated that various interventions that affect the development of cancer in mice act by modulating the IGF axis; including green tea extract, that increases IGFBP-3 and lowers IGF-I levels; and the flavanoids quercetin and apigenin. It was observed that IGFBP-3 directly induces apoptosis in cancer cells and that it mediates cell death induced by other agents, including p53, which mediates IGFBP-3 actions Several cytokines, including TGFβ and TNFα and anticancer drugs, such as retinoic acid can also induce IGFBP expression as well as apoptosis. The action of these agents appear to require the expression of IGFBP-3 for the induction of apoptosis, as their effects are blocked by reagents that specifically block IGFBP-3 (such as siRNA, antisense oligomers, and neutralizing antibodies). IGFBP-3-induced apoptosis has now been detected in multiple models, and IGFBP-3 has been identified as a target of the HPV oncoprotein E7, that targets it to degradation, thereby preventing its apoptotic effects. It was also demonstrated that IGFBP-3 is a downstream target of EWS/FLI-1 and is lost in sarcoma. IGFBP-3 was identified as a p53 target gene that was frequently inactivated by methylation in germ cell tumors and bladder carcinoma. IGFBP-3 inhibits IGF-I action on growth and survival of cancer and also directly induces apoptosis in cancer cells. Another object is to test the role of IGFBP3 in the resistance of mice to chemotherapy but also in the sensitization of cancer cells to various chemotherapy drugs.

Pharmacological Blockade of the IGF Axis in Cancer

As a result of the overwhelming data dealing with the role of the IGF system in the development and progression of various cancers, over a dozen pharmaceutical companies have initiated the development of IGF antagonists. Several classes of IGF blockers are now in clinical trials, including IGFBPs, IGF-receptor blocking antibodies, and various small molecule inhibitors. The most promising and in the most advanced stage of development are the IGF-I receptor antibodies which are in Phase II trials in several types of malignancies and have shown promising effects in early reports. Interestingly, in most published papers, IGF-IR blockade is synergistic with agents that block parallel pathways. As discussed below, there is a clear rationale for combining IGF-IR blockade and chemotherapy, including likely synergistic efficacy as well the expected avoidance of host toxicity. Another object is to test the role of IGF-receptor blocking antibodies in the resistance of mice to chemotherapy but also in the sensitization of cancer cells to various chemotherapy drugs.

Short-Term Starvation Induces Differential Stress Resistance Against Oxidative Stress in Yeast To test whether constitutively active oncogenes or oncogene homologs can prevent the switch to a protective maintenance mode in response to starvation, whether acute starvation would be as effective in increasing stress resistance as it has been shown for long-term calorie restriction (CR) was first determined. Such long-term CR strategy would not be appropriate for chemotherapy treatments since it requires several months to be effective. DSR studies were first performed in S. cerevisiae. A short-term starvation paradigm, as well as the deletion of the SCH9/AKT and/or RAS2 genes, each of which mimics in part calorie restriction and was shown to cause high resistance to oxidative stress, was selected. It was believed that the combination of these genetic manipulations with starvation would maximize DSR. The combination of STS (switch from glucose medium to water at day 1 [OD=9-10] and incubation in water for 24-48 hours) with the deletion of SCH9/AKT or both SCH9/AKT and RAS2 increased resistance to a 30-60 minute treatment with hydrogen peroxide or menadione a 1,000- to 10,000-fold compared to cells expressing the constitutively active oncogene homolog $RAS2^{val19}$ or cells lacking SCH9/AKT (sch9/aktΔ) but expressing $RAS2^{val19}$ (sch9/aktΔRAS2$^{val19}$) (FIG. 17A). The rationale for this experiment was to model in a simple system the effect of the combination of short-term starvation and a genetic approach on the differential protection of normal and cancer cells. The results show that the expression of the oncogene-like RAS2$^{va}$19 prevents the 1,000-10,000-fold protection caused by the combination of STS and inhibition of Sch9/Akt activity.

The effect of another oncogene homolog (SCH9/AKT) on resistance to oxidants was also tested. As with $RAS2^{val19}$, overexpression of SCH9/AKT sensitized yeast cells to both $H_2O_2$ and menadione (FIG. 17B). Similarly to the effect of the deletion of RAS2 and SCH9/AKT, the deletion of the homolog of TOR, another gene implicated in cancer, slightly increased the resistance to oxidants. Whereas the expression of $RAS2^{val19}$ completely reversed the protective effect of the deletion of SCH9/AKT, it only had a minor effect on the reversal of the protective effect of the tor1α (FIG. 17B). This is an important difference because it suggests that it may be problematic to attempt to achieve DSR by inhibiting intracellular targets instead of inhibiting receptors extracellularly since inhibition of certain cytosolic pathways may also protect cancer cells in which the target is downstream of the oncogenic mutation. For example the inhibition of Akt may also protect cancer cells with a PTEN mutations that causes the constitutive activation of PI3K.

Short-term Starvation Induces Differential Stress Resistance Against Alkylating Agents in Yeast To test whether DSR would also occur after treatment of yeast with a high concentration of chemotherapy drugs, the effect of SCH9/AKT mutations on the toxicity caused by alkylating agents methyl methanesulfonate (MMS) and cyclophosphamide (CP, a widely used chemotherapy drug) was studied. As a very simple model for the effect of STS and/or IGF-I inhibition on metastatic cancer mutants lacking SCH9/AKT were mixed in the same flask with mutants lacking SCH9/AKT but also expressing $RAS2^{val19}$ at a 25:1 ratio and the mixture was exposed to chronic treatment with CP or MMS. The monitoring of the viability of the two mixed populations was possible since each population can be distinguished by growth on plates containing different selective media. Of the approximately 10 million sch9/aktΔRAS2$^{val19}$ cells mixed with 250 million sch9/aktΔ, less than 5% of the sch9/aktΔRAS2$^{val19}$ cells survived a 48-hour treatment with 0.01% MMS whereas the great majority of sch9/aktΔ survived this treatment (FIG. 17C). Similar results were obtained with mixed sch9/aktΔRAS2$^{val19}$/sch9/aktΔ cultures treated with cyclophosphamide (FIG. 17D). An experiment in which each cell type was treated with CP separately was also performed and a similar differential stress resistance between cells expressing RAS2$^{val19}$ and cells lacking SCH9/AKT was observed. These results in a very simple model system suggest that DSR has the potential to work effectively against metastatic cancer by selectively killing cancer cells but not normal cells. Considering the very limited success of therapies aimed at treating metastasis, it is essential to explore further the potential of new strategies like DSR.

Short-term Starvation Induces Differential Stress Resistance Against Cyclophosphamide in Mammalian Cells To test the efficacy of the starvation-based DSR method on mammalian cells, primary rat mixed glial cells (astrocytes+ 5-10% microglia), three different rat, one human glioma and one human neuroblastoma cell lines were incubated in medium containing low serum and either normal (1 g/L) or low (0.5 g/L) glucose and then treated with the chemotherapy drug CP (1 g/L glucose is within the normal human blood glucose range whereas a 0.5 g/L glucose concentration is reached in mammals during prolonged starvation). The 1% serum concentration minimizes the contribution of glucose from serum, which is approximately 1 g/L. To avoid major differences in proliferation, glia and glioma cells were allowed to reach a 100% confluency. Whereas 80% of glial cells were resistant to 12 mg/ml CP in the presence of 0.5 g/L glucose, only 20% of the cells survived this treatment in 1 g/L glucose (FIG. 2A). The increased stress resistance at the lower concentration of glucose (0.5 g/L) was observed starting at 6 mg/ml CP but became much more pronounced at 12 mg/ml CP (FIG. 2A). By contrast, the lower glucose concentration did not increase the resistance of cancer cell lines including C6, A10-85, RG2 rat glioma, LN229 human glioma or human SH-SY5Y neuroblastoma cells to 12-14 mg/ml CP (FIG. 2A). The lower glucose concentration actually decreased the resistance of CP to RG2 glioma cells to 6 and 8 mg/ml doses (FIG. 2A). To determine whether the DSR is affected by the high cell density this experiment was also repeated with cells that were only 70% confluent and similar results were obtained.

To determine whether the constitutive activation of the Ras/Erk pathway may be implicated in the unresponsiveness of the glioma and neuroblastoma cells above to starvation the phosphorylation of Erk, which functions downstream of Ras, in 1% serum or serum-starved cells was measured. The phosphorylation data indicate that 2 of the 5 lines maintain a high level of Erk activity even after a 16-hour starvation (FIG. 11B), in agreement with the 30% frequency of Ras mutations in human cancers. The reduction of Erk phosphorylation but inability to increase protection to cyclophosphamide in the other 3 lines (FIG. 2A) is consistent with an anti-resistance role of other common mutations in pro-growth pathways such as the PTEN/PI3K/AKT pathway. Notably, it is believed that the constitutive activation of any pro-growth pathway (not only the Ras and Akt pathway) would make cancer cells unresponsive or less responsive to the starvation or IGF-I reduction-dependent protection.

The experiments above were performed in medium containing 1.0 g/L glucose and different concentrations of glucose. The effect of only reducing the level of serum from the standard 10% to 1% on the toxicity of high-dose cyclophosphamide was also tested. Treatment with 15 mg/ml CP was toxic to primary glial cells in 10% serum but the switch to 1% serum caused a reduction in toxicity (FIG. 2B). By contrast, the same concentration of CP was as toxic to CG glioma cells in 10% serum as it was in 1% serum (FIG. 2B).

In the *S. cerevisiae* experiments above it was showed that the deletion of SCH9/AKT protects whereas the constitutive activation of Ras2 ($RAS2^{val19}$) or SCH9/AKT overexpression sensitizes the yeast cells to oxidants and/or alkylating agents. Since mammalian Ras and Akt are major signal transduction proteins downstream of the IGF-I receptor, and considering the role of the IGF-I pathway in regulating stress resistance, the effect of IGF-I and of an antibody against IGF-IR on DSR was also tested. It was reasoned that primary cells would respond to the IGF-1-inhibiting treatment by increasing stress resistance whereas cancer cells, which often express oncogenes that cause constitutive Ras and Akt activation, would not. Treatment with 100 ng/ml IGF-I (in the low IGF-I range for human adults) caused a 3-fold increase in the toxicity of cyclophosphamide to primary mixed glia but did not increase the toxicity of CP to C6 glioma cells (FIG. 2C). Furthermore, pre-incubation with an anti-IGF-IR antibody (aIR3) protected primary glia but not three glioma cell lines tested against CP toxicity (FIG. 2D). A similar sensitizing role of IGF-I was observed with primary rat cortical neurons but not the rat pheochromocytoma tumor PC12 cell line treated with oxidants. These results in normal glia and in rat and human glioma and neuroblastoma cell lines are consistent with those in yeast cells and support the belief that short-term starvation and/or drugs that down-regulate IGF-IR/Ras/Akt signaling can protect normal cells much more effectively than cancer cells against chemotherapy. Notably, this differential stress resistance should apply to the great majority of pro-growth oncogenic mutations and not only to cancer cells with mutations in the Ras, Akt or mTor pathways. In fact, it worked with all the six cancer cell lines tested (FIG. 2), independently of cancer origin.

Short-term Starvation Induces Differential Stress Resistance Against Chemotherapy in Mice To test DSR in vivo mice were treated with high dose chemotherapy in combination with STS and/or GH/IGF-I lowering strategies. For this purpose etoposide, a widely used chemotherapy drug which damages DNA by multiple mechanisms and displays a generalized toxicity profile ranging from myelosuppression to liver and neurologic damage, was selected. A/J mice were administered with a high dose of etoposide (80-110 mg/kg) after a period of starvation, GH/IGF-I lowering treatment or both. In humans, a third of this concentration of etoposide (30-45 mg/kg) is considered to be a high dose and therefore in the maximum allowable range.

To reduce GH/IGF-I mice were pre-treated for four days with the somatostatin analogue octreotide. This pre-treatment was followed by etoposide administration. A sub-group of mice were also starved for 48 hours (STS) before treatment with etoposide. The mice pre-treated with octreotide received this treatment for 4 additional days after chemotherapy. Whereas 80 mg/kg etoposide killed 43% of control (Eto, n=23, 2 experiments) and 29% of octreotide pre-treated mice (Oct/Eto, n=17), none of the mice treated with octreotide and also pre-starved for 48 hours died after 80 mg/kg etoposide treatment (Oct/STS/Eto/Oct, n=35) and only one of the mice that were only starved (STS/Eto, n=16) died after etoposide treatment (FIG. 7A). Remarkably, STS-octreotide pre-treated mice, which lost 20% of the weight during the 48 hours of starvation, regained all the weight in the four days after chemotherapy (FIG. 7B) whereas in the same period the control mice lost approximately 20% of the weight (FIG. 7B). Control mice treated with etoposide showed signs of toxicity including reduced mobility, ruffled hair and hunched back posture whereas Oct/STS/Oct pre-treated mice showed no visible signs of stress or pain following etoposide treatment.

The effect of STS alone on the protection of mice of another genetic background (CD1) was also tested. To determine whether an extended STS strategy can be effective against a higher concentration of chemotherapy drugs 110 mg/kg etoposide was administered and the starvation period was also increased to 60 hours. Based on the experiments with oxidative stress, it was determined that this period is the maximum STS that provides protection. Longer starvation periods can weaken the animals and have the opposite effect. This concentration of etoposide killed all the control mice (Eto 110) but none of the STS pre-treated mice (STS/Eto 110, n=5) (FIG. 7C). As with the A/J mice, pre-starved CD1 mice lost 40% of the weight during the 60 hours of starvation but regained all the weight in the week after the etoposide treatment and showed no visible sign of toxicity (FIG. 7D).

The effect of the STS-based method was similar in athymic (Nude-nu) mice, widely used in cancer research to allow the study of human tumors. Whereas 100 mg/kg etoposide killed 56% of the nude mice and all the mice co-treated with octreotide, none of the STS/Eto/Oct or STS/Eto treated mice (48-hour starvation) died (FIG. 7E). As observed with the other two genetic backgrounds, the pre-starved mice gained weight during the period in which the Eto-treated mice lost weight (FIG. 7F).

In summary, out of 70 mice from three genetic backgrounds that were starved before etoposide treatment, only one mouse in the STS only group and none of the mice in the STS/Oct group died (FIG. 7I). By contrast, out of the 63 mice treated with etoposide alone or etoposide and octreotide, 34 died of toxicity. These results are consistent with the yeast and glia/glioma data showing increased resistance to chemotherapy toxicity in response to starvation. In mice, octreotide alone was not sufficient to protect against etoposide toxicity and virtually all the protection was due instead to STS. The discrepancy between the effect of IGF-I in vitro and octreotide in vivo may be due to the relatively modest effect of octreotide on the reduction of circulating IGF-I level.

Transgenic Mice with Low Circulating IGF-1 (LID) Show Increased Resistance Against Cyclophosphamide To determine whether a much more severe reduction in IGF-I level than that achieved with octreotide can increase resistance to chemotherapy in vivo as shown in vitro, the resistance against a high dose of cyclophosphamide of male and female LID mice, in which the liver IGF-I gene was conditionally deleted, resulting in a 75-90% reduced serum IGF-I concentration, was studied. The LID mice treated with 500 mg/kg cyclophosphamide showed a remarkable improvement in resistance, with 30% mortality vs the 70% mortality for control mice (FIG. 7G, P<0.002). Furthermore, the LID mice lost an average of 10% of weight vs 20% weight loss in control mice (FIG. 7H). The 70% surviving LID mice also did not show any signs of toxicity. Together with the in vitro results with IGF-I and anti-IGF-IR antibodies and the established role of starvation on the reduction of IGF-I levels, these data suggest that the inhibition of IGF-IR signaling may mediate part of the effects of STS on resistance to cyclophosphamide in vivo. Notably, IGF-IR antibodies have been used successfully in a number of studies to reduce the growth or increase the death of cancer cells and are currently being evaluated in clinical trials.

Short-term Starvation in Combination with Octreotide Protects Mice But not Cancer Cells Against High Dose Chemotherapy To determine whether the differential stress resistance observed in yeast and mammalian cells would also occur in mice, the survival of mice injected with cancer cells was followed. A particularly aggressive neuroblastoma (NB) tumor line (NXS2) (NB is the most common extra cranial solid tumor, and the first cause of lethality in pre-school age children) was selected. Advanced NB patients, who represent approximately 50% of the cases, show metastatic dissemination at diagnosis, and have a long-term survival rate of only 20% in spite of aggressive chemotherapy with autologous hematopoietic stem cell support.

The NXS2 neuroblastoma line in mice induces consistent and reproducible metastases in a pattern which resembles the clinical scenario observed in neuroblastoma patients at advanced stages of disease. Experimental metastases in the liver, kidneys, adrenal gland, and ovaries were observed after 25-30 days of the inoculation with 200,000 NXS2 cells (Table 2) as previously described. The tumor development and survival of STS/Eto treated mice was significantly different from that of controls (Gr. 7 vs. Gr. 1 p<0.0001) (FIG. 8A, Table 2) suggesting that STS alone provides strong protection to the mouse but only partial protection of cancer cells against etoposide. Based on these results, the use of STS alone would require several or many chemotherapy cycles to obtain toxicity to cancer cells comparable to that caused by high dose chemotherapy alone.

By contrast, none of the Oct/STS/Eto/Oct injected with NXS2 cells died until day 46, at a point when all the controls had died of cancer (FIG. 8A, Table 2) (Gr. 4 vs. Gr. 1 p<0.0001). One mouse from this group survived until day 130. The survival of Oct/NXS2/STS/Eto/Oct mice was not significantly different from that of NXS2/Eto and Oct/NXS2/Eto/Oct groups (Table 2) but, as described above, 50% of mice not protected with STS died of etoposide toxicity (FIG. 7A). Even if the initial etoposide-dependent deaths are not considered, the long-term survival of the octreotide/STS/NXS2/etoposide group was not significantly different from that of the NXS2/etoposide. These results suggest that in combination with octreotide, STS protects the animal but not or much less the cancer cells against chemotherapy. Although a single injection of high dose etoposide cannot be expected to cure the mice injected with NXS2 cancer cells, the high protection provided by STS/Oct against the initial chemotherapy toxicity to mice but not cancer cells provides a system that allows multiple or many cycles of etoposide treatment. Although the Eto alone group appears to perform slightly better than the STS/Oct/Eto group, the initial high toxicity would prevent the use of high dose Eto alone. Attempts to combine weekly injections of etoposide with STS/Oct were discontinued because of the damage to the tails caused by the many i.v. injections, which prevented additional injections. Thus, the present results show that the differential stress resistance also works in vivo.

Octreotide does not Sensitize NXS2 Neuroblastoma Cells to Etoposide

Somatostatin analogues have been reported to promote anti-tumor activity through two distinct effects: direct actions, mediated by somatostatin receptors, and indirect actions, independent of the receptors. The somatostatin/octreotide receptor-mediated effect includes inhibition of cell cycle and growth factor effects, and induction of apoptosis. In contrast, the indirect effects comprise inhibition of the release of growth factors such as growth hormone and IGF-I. To determine whether octreotide was acting directly on cancer cells the toxicity of etoposide to NXS2 cells cultured in vitro in the presence or absence of octreotide was tested. Either 10 or 50 micromolar octreotide did not sensitize NXS2 cells to etoposide treatment (FIG. 8B) suggesting that it is not increasing the survival of the NXS2 injected mice by directly sensitizing the cells to etoposide. Because of the many studies showing an anti-tumor growth and survival effect of lower GH and IGF-I or inhibition of the IGF-I and GH receptors, these results suggest that octreotide may be improving long-term survival of STS treated mice by its well established role in decreasing GH and IGF-I levels although other effects cannot be ruled out. Notably octreotide and other somatostatin analogues have been shown to have therapeutic effects in a number of cancers. In the absence of short-term starvation, octreotide alone did not protect mice against NXS2-dependent death (FIG. 8A), suggesting that it is the synergism between etoposide and octreotide that is effective in killing tumor cells. These results also suggest that octreotide pretreatment before the injection of NXS2 cells does not affect the tumor growth.

Targeted Deletion of Hepatic Igf1 in TRAMP Mice Leads to Dramatic Alterations in the Circulating IGF Axis But does not Reduce Tumor Progression The role of systemic and local IGF-I in the development of prostate cancer is still controversial. TRAMP mice express the SV40 T-antigen under the control of the probasin promoter, and spontaneously develop prostate cancer. TRAMP mice was crossed with liver IGF-I deficient (LID) mice to produce LID-TRAMP mice, a mouse model of prostate cancer with low serum IGF-I, to allow the study of the effect of circulatory IGF-I levels on the development of prostate cancer. LID mice have a targeted deletion of the hepatic Igf1 gene but retain normal expression of Igf1 in extra-hepatic tissues. Serum IGF-I and IGFBP-3 levels in LID and LID-TRAMP mice were measured using novel assays, which showed that they are approximately 10% and 60% of control L/L⁻ mice, respectively. Serum GH levels of LID-TRAMP mice were 3.5-fold elevated relative to L/L-TRAMP mice p<0.001). Rates of survival, metastasis, and, the ratio of genitourinary tissue weight to body weight were not significantly different between LID-TRAMP and L/L-TRAMP mice (FIG. 18). There was also no difference in the pathological stage of the prostate cancer between the two groups at 9-19 weeks of age. These results are in striking contrast to the published model of the GH-deficient lit/lit-TRAMP, which has smaller tumors and improved survival, and indicate that the reduction in systemic IGF-I is not sufficient to inhibit prostate cancer tumor progression in the TRAMP model, which may require reduction of GH levels as well. On the other hand, LID mice were less susceptible to chemotherapy toxicity as shown in FIG. 7G, indicating that in some and possibly many cancers, the main benefit of IGF blockade, may in fact be in the potential for protection of normal but not tumor cells against chemotherapy.

Development of Novel Mouse Specific IGF-related Assays (IGFBP-3, IGF-I, and Other Mouse IGF Axis Analytes)

One object is to study the effects of GH/IGF lowering treatments together with chemotherapeutic agents in mouse models. A key element in studying mice models involving IGF-related effects is the development of mouse-specific IGF and IGFBP assays. Novel assays for the IGF axis have been developed. Highly accurate mouse-specific assays for mIGF-I, mIGF-II, mGH, mALS, mIGFBP-1, mIGFBP-2 and mIGFBP-3 have been developed (FIG. 19). These mouse-specific ELISA assays have been recently developed using rat-anti-mouse monoclonal antibodies and recombinant mouse IGF-related proteins from R&D Systems. These assays have sensitivities of less than 0.2 ng/mL, have no cross-reactivity with human homologues (human serum reads <1 ng/ml) and no interference with other IGFs or IGFBPs. Inter- and intra-assay CVs are <6% and recoveries are 88-110% in the linear range of the assays. Importantly, a clear developmental pattern for IGF-I, IGFBP-3, and ALS has been demonstrated, and it was showed that levels are low in GH deficient mice and in LID (Liver IGF-deficient) mice as well as being zero in the serum specific KO mice.

Starvation-dependent Protection Against Chemotherapy

To understand whether STS is effective against a wide range of chemotherapy drugs, its effect against the widely used drug doxorubicin was also tested. A 48-hour STS effectively protected all mice (n=5) against 16 mg/Kg doxorubicin (FIG. 20). By contrast, the same dose of doxorubicin killed all the mice that were not pre-starved (FIG. 20).

Low IGF-I-dependent Protection Against Chemotherapy

The role of IGF-I deficiency in the resistance to etoposide and doxorubicin was tested. Surprisingly, the IGF-I deficient LID mice were less resistant to etoposide compared to controls, although the difference in survival was not significant (FIG. 21). By contrast, LID mice were remarkably more resistant than controls to treatments with doxorubicin. In this experiment multiple cycles of chemotherapy were modeled by injecting the mice first with 20 mg/kg and 22 days later with a higher dose (28 mg/kg) of doxorubicin. All LID mice survived the multiple treatments whereas 75% of control mice died (FIG. 22).

Mechanisms of Regulation of Oxidative Stress and Chemotherapy Resistance

In the experiments shown below primary rat neurons were studied to begin to identify effectors of resistance to oxidative stress and chemotherapy downstream of Ras. It was showed that 2 inhibitors of MEK1/ERK, signaling kinases downstream of Ras, increase resistance to both hydrogen peroxide and menadione (FIG. 23), providing evidence for a role of ERK in regulating resistance to chemotherapy.

Starvation, Oncogene Homologs and Differential Resistance to Chemotherapy Drugs in S. cerevisiae The belief that the DSR system can protect normal but not cancer cells against chemotherapy is based on the findings that starved yeast cells lacking oncogene homologs RAS2 or SCH9/AKT are resistant to oxidative stress as well as alkylating agents. In previous studies it was showed that this resistance is reversed by the overexpression or constitutive activation of RAS2 or SCH9/AKT, which models oncogenic mutations commonly found in human cancers. Thus, one object is to understand whether and how starvation and/or down-regulation of these pathways can protect normal cells but not cells expressing oncogene homologs against different classes of chemotherapy drugs. To dissect the mechanism of protection the role of various stress resistance transcription factors inhibited by the Ras and Sch9/Akt pathways and in the resistance to these chemotherapy drugs will be tested. Resistance to alkylating agents, a topoisomerase II inhibitor, a thymidylate synthetase inhibitor, and pro-oxidant drugs will be tested. Previous results point to the error-prone polymerase Rev1 and recombination proteins in the mediation of spontaneous age-dependent mutations. Here, the role of these error-prone enzymes and homologous recombination proteins in the sensitivity of cells expressing or overexpressing RAS and SCH9/AKT to chemotherapy agents will also be tested. Finally, a number of strains previously generated to characterize the range of DNA damage caused by the various chemotherapy drugs and the effect of Ras and Sch9/Akt activity on this damage will be used. Although results in S. cerevisiae do not always reflect the biology of mammalian cells, the studies suggest that oncogene homologs play conserved roles in the modulation of resistance to chemotherapy drugs.

The following studies will be performed:

a) Determine the resistance of starved (48 hours in water) or non-starved wild type, ras2Δ, sch9/aktΔ, ras2Δsch9Δ expressing either RAS2$^{val19}$, SCH9/AKT or an empty vector to cyclophosphamide, etoposide, 5 FU, and menadione (vitamin K3). Both acute and chronic treatments will be performed (see FIG. 17 legend and detailed methods). Mix culture experiments as described in the legend of FIGS. 17C and D will also be performed. These chemotherapy drugs were chosen because they are commonly used to treat cancer (with the exception of menadione) but also because they represent different categories of toxicity: DNA alkylation (CP), topoisomerase II inhibition (ETO), thymidylate synthetase inhibition (5FU), and oxidation-dependent single and double strand DNA breaks (menadione). RAS2$^{val19}$ or SCH9 overexpression model the very common oncogene mutations that cause the activation of Akt or Ras in cancer cells (see FIG. 17 legend and detailed methods).

b) Determine the role of the major stress resistance transcription factors Msn2/Msn4, Gis1 and forkhead transcription factors Fhl1, Fkh1, Fkh2, and Hcm1 on the protection of sch9/aktΔ and ras2Δ mutants against DNA alkylation, topoisomerase II inhibition, thymidylate synthetase inhibition, and oxidation-dependent single and double strand DNA breaks. These transcription factors have been identified as major mediators of resistance to multiple stresses in yeast, C. elegans, and mammalian cells. These studies will help identify the mediators of resistance to chemotherapy downstream of Sch9/akt and Ras and may point to human transcription factors that play similar roles.

c) Study the mechanisms of RAS2- and SCH9/AKT-dependent sensitization of cells against DNA damage in yeast cells treated with cyclophosphamide, etoposide, 5 FU, and menadione. Examine point mutations, small insertions/deletions, and gross chromosomal rearrangements using systems described below. Determine the role of Rev1 and Rad52 in the DNA damage caused by the various chemotherapy agents by studying reu1Δ, rad52Δ, ras2Δ, sch9/aktΔ and sch9/aktΔrev1Δ, ras2Δrad52Δ, sch9Δ rad52Δ, ras2Δreu1Δ. Resistance to the chemotherapy agents in sch9/aktΔ and ras2A mutants overexpressing REV1 or RAD52 will also be studied. These experiments will test the role of error-prone polymerases and homologous recombination in the toxicity caused by chemotherapy drugs.

One object is to confirm that the combination of starvation and the lack of both SCH9/AKT and RAS2 causes an up to 10,000-fold increase in the resistance to menadione and hydrogen peroxide but also caused a major increase in the resistance to alkylating agents cyclophosphamide and MMS. It is expected that resistance to these toxins will be reversed by the overexpression of SCH9/AKT or by the constitutive activation of RAS2 (RAS2$^{val19}$). However, the effect of either STS or ras2-sch9/akt mutations alone on DSR will be investigated further. In previous studies it was also determined that 5FU and etoposide are toxic to yeast, as show by others. It is believed that the DSR will also work with these chemotherapy drugs.

Based on previous studies it is expected that stress resistance zinc finger transcription factors Msn2/Msn4 and Gis1 and to a lesser extend forkhead transcription factors (TF) Fhl1, Fkh1, Fkh2, and Hcm1 will modulate protection against chemotherapy-dependent DNA damage. Although it has been shown that Msn2/Msn4 and Gis1 are effective against a variety of stresses, it cannot be excluded that different TF may provide protection against different chemotherapy drugs.

It is also believed that the error-prone polymerase Rev1 plays a major role in the DNA damage caused by alkylating agents, oxidants and topoisomerase II inhibitors as it did in the generation of spontaneous mutations which appear to be caused by a variety of insults including oxidative damage. It will be very important to determine how each drug affects DNA damage ranging from point mutations to gross chromosomal rearrangements (GCRs) both after acute and chronic treatments.

Another object is to investigate the role of error-prone polymerases such as Rev1 in the generation of chemotherapy-induced DNA damage in mammalian cells.

Starvation, IGF-I, Oncogenes and Differential Resistance to Chemotherapy Drugs in Primary Mammalian Cells and Cancer Cell Lines The results indicate that reduction in the level of glucose or serum protects primary glial cells more effectively than rodent or human neuroblastoma and glioma cancer cells against high dose cyclophosphamide. It was also showed that the presence of IGF-I sensitized primary glia but not cancer cell lines against cyclophosphamide. These results are consistent with the belief first tested in S. cerevisiae, that Ras and Akt, which function downstream of IGF-I in mammals, regulate stress resistance and that starvation or IGF-I receptor inhibition would differentially protect normal and cancer cells against chemotherapy. Activation of the Ras or Akt pathway and possibly of other pro-growth pathways by oncogenic mutations is expected to force the cells into a pro-growth and low stress resistance mode. One object is to perform experiments analogous to those for S. cerevisiae: the cyclophosphamide toxicity studies will be continued and extended to different toxic agents to begin to establish whether the STS/low IGF-1-dependent DSR has the potential to be applied to a wide range of chemotherapy treatments. Another object is to study the mechanism responsible for the effect of oncogenes and proto-oncogenes on resistance to chemotherapy. The putative role of Ras and Akt in sensitizing the cells to chemotherapy but also protecting against apoptosis, at least under certain conditions will also be addressed. Finally, the mechanisms of protection with focus on Erk, p38, and FOXO3, which have been implicated as either positive or negative regulators of stress resistance will be studied.

The following studies will be performed:

a) Investigate the role of low serum (1%) or low glucose (0.5 g/L) on the resistance of primary glia and 7 lines of glioma and neuroblastoma cells to different classes of chemotherapy drugs. Primary rat glial cells, rat glioma cell lines (C6, A10-85, RG2 and 9L), human glioma (LN229), mouse NXS2 neuroblastoma and human neuroblastoma (SH-SY5Y) cell lines against cyclophosphamide, etoposide, 5 FU, and menadione will be tested (see FIG. 2 legend and detailed methods). The focus on rat gliomas will enable one to determine the DSR between rat glia-derived cancer cells and primary rat glial cells. In previous studies it was showed that the reduction of either serum from 10% to 1% or of glucose from 1 g/L to 0.5 g/L protected primary glia but not cancer cell lines against cyclophosphamide (FIG. 2). One object is to continue the studies of the role of low serum or low glucose on the resistance to cyclophosphamide but also extend the studies to the different classes of chemotherapy drugs listed above (see studies described above and detailed methods). Both cell death (MTT, LDH assays) and apoptosis (Annexin V, TUNEL) will be measured.

b) Investigate the role of IGF-I in the resistance of primary glia and the 7 lines of glioma and neuroblastoma to cyclophosphamide, etoposide, 5 FU, and menadione. The effect of IGF-I and of IGF-I inhibitory proteins including IGFBP-3 and IGF-I antibodies on stress resistance of normal and cancer cells will be studied (see FIGS. 2C and D and detailed methods).

c) Investigate the effect of different concentrations of IGF-I, serum, and glucose on the activity of the Ras and Akt pathways in primary glial cells and cancer cell lines (FIG. 11B). The DSR method is based on the belief that normal but not cancer cells will up-regulate stress resistance systems normally inhibited by the Ras and Akt pathways in response to starvation or a reduction in growth factors such as IGF-I. Because Ras and Akt are among the signal transduction proteins most commonly found in a constitutively active or up-regulated state in cancers, whether either the Ras or Akt pathway or both remain active after the switch to low serum, low IGF-I, and low glucose as suggested in the studies described above (FIG. 11B) will be determined. The 7 different cancer lines listed above as well as primary rat glia will be tested (see studies described above and detailed methods). For primary glia the time course for the inactivation of the Ras and Akt pathways after the switch to low serum, IGF-I, or glucose will also be determined.

d) Investigate the role of Ras and Akt in the regulation of resistance against cyclophosphamide, etoposide, 5 FU, and menadione in primary glia and determine whether cells are protected against necrosis or apoptosis (see detailed method). The yeast studies indicate that Sch9/Akt and possibly Ras regulate oxidative stress-dependent DNA damage by controlling a pathway that includes serine/threonine kinases, and stress resistance transcription factors. One object is to test the role of inhibition of Ras and Akt signaling in the protection against the chemotherapy drugs listed above in both primary glia and glioma cells lines. Whether the cell death is apoptotic or necrotic (see detailed method) will be determined. Another object is to study the role of Erk, p38, and FOXO transcription factors in the regulation of stress resistance downstream of Akt and Ras. These kinases and transcription factors have been implicated in the regulation of stress resistance. The phosphorylation status of Erk, p38, Akt, and FOXO3 in primary cells treated with IGF-I (see detailed method) will be determined. Still another object is to test the effect of the inhibition of Erk, p38, PI3K/AKT activity and overexpression of FOXO3 transcription factors on the resistance to chemotherapy drugs in primary rat glial cells treated with IGF-IR antibodies. Inhibitory drugs and/or siRNA will be used to reduce the activity of the above enzymes/transcription factors in primary glia treated with IGF-I.

In the results described above (FIG. 2) starvation and/or reduction of IGF-I was effective in protecting normal cells but not cancer cells against the alkylating agents cyclophosphamide. Based on the results it is believed that the reduction in IGF-I signaling or starvation will also protect against menadione and etoposide treatment (FIGS. 7 and 8B). As suggested by the studies described above (FIG. 11B) it is expected that Ras or Akt and downstream effectors will be constitutively active in the cancer cell lines but not in the primary glia. Thus, the removal or reduction of IGF-I, serum, or glucose should attenuate the activity of these pathways in glia but not glioma or neuroblastoma cells. The "apoptosis" experiments should enable one to discern the pro-damage and anti-apoptotic role of Ras and Akt. One possibility suggested by the experiments described above is that the inhibition of Ras increases apoptosis in the first 24 hours after treatment with oxidants, but eventually decreases necrosis. Based on the results described above, it is believed that Erk and to a lesser extent P38 mediate the sensitization to stress. This result is consistent with the opposing effects of Erk and p38 in the regulation of apoptosis.

Another object is to understand how stress resistance affects other primary cells as well as cell lines representing additional types of cancers including major ones such as breast and colon carcinomas. Yet another object is to examine the role of additional signal transduction proteins and transcription factors in the resistance to chemotherapy drugs. For example, it would be useful to investigate additional transcription factors implicated in stress resistance such as FOXO1.

Starvation and Differential Resistance to Chemotherapy Drugs in Mice

The results in mice suggest that STS can be effective in the protection against a dose of etoposide (topoisomerase II inhibitor) that kills approximately 50% of the non-starved mice. It was also showed that STS alone only partially protects injected NXS2 neuroblastoma cells. This protection was abolished by pre-treatment with the somatostatin analog octreotide. One object is to test whether the combination of octreotide and STS is effective in the protection of mice against different chemotherapy drugs (etoposide, 5 FU, and cyclophosphamide, and menadione). Another object is to test the effect of STS/octreotide against several cancer cell lines using xenograft models (etoposide only). In previous results only a single round of chemotherapy was administered, which was not sufficient to cure the mice from NXS2 cancer. Because pre-starved mice did not show any visible sign of toxicity, one object is to focus on multiple rounds of STS/octreotide/chemotherapy to attempt to kill all the injected cancer cells or at least obtain a much greater delay of the cancer-dependent death in animals injected with cancer cells.

The following studies will be performed: In previous studies it was showed that STS protected against high dose etoposide. One object is to test whether STS is effective in the protection of mice against various chemotherapy drugs. The role of STS on the protection of 4 different mouse genetic backgrounds to high dose etoposide, 5 FU, and cyclophosphamide, and menadione will be studied. Different mouse strains will be studied to allow xenografts with different types of cancer cell lines and also to confirm that the STS strategy is effective in a variety of specific genetic backgrounds. The chemotherapy drugs above were chosen based on previous results and because they are among the most commonly used in the treatment of human cancers. The breast and ovarian carcinomas models were added to test the effect of STS on more common carcinomas.

a) Test the effect of STS in combination with octreotide pre-treatment on the resistance of C57BL6 mice against cyclophosphamide, etoposide, 5 FU, and menadione.

b) Perform multiple injections of etoposide in combination with STS and octreotide treatment in A/J mice pre-injected with NXS2 or Neuro2a neuroblastoma cells.

c) Perform multiple injections of etoposide in combination with STS and octreotide treatment in athymic Nude (nu/nu) mice pre-injected with HT1A-230 or SH-5Y-SY human neuroblastoma cells.

d) Perform multiple injections of etoposide in combination with STS and octreotide treatment in SCID mice pre-injected with MDA-MB1-231 human breast carcinoma.

e) Perform multiple injections of etoposide in combination with STS and octreotide treatment in athymic Nude (nu/nu) mice pre-injected with OVCAR-3 human ovarian carcinoma.

f) To begin to understand the role of the GH/IGF-I axis in the DSR effect of STS, the effect of starvation on the level of growth hormone, IGF-1, IGFBP1, and IGFBP3 after the 48-hour starvation will be tested (see previous studies described above and detailed methods).

The systems listed above are among the major model systems for the treatment of neuroblastoma. The ovarian carcinoma and breast carcinomas model systems were added to begin to understand whether the STS/octreotide system is also effective in protecting normal but not other cancer cell types against high dose chemotherapy.

Based on previous results it is believed that STS will be consistently effective against high dose etoposide and to a lesser extent against cyclophosphamide. Octreotide is not expected to protect against etoposide but may increase protection against other drugs and especially menadione. Because of the very low toxicity of etoposide in combination with STS and octreotide, the multiple injection experiments are likely to be more effective against the injected NXS2, Neuro2A, HTLA-230, SH-5Y-SY, MDA-MB1-231, and OVCAR-3 cells compared to single injections. Based on previous results, octreotide should increase the toxicity to NXS2 cells and may increase the toxicity of etoposide against the cancer cell lines listed above. In fact, it was showed that it had no direct protective effect on NXS2 cells (FIG. 8B) suggesting that it does not act through the activation of a specific receptor which may be specific to NXS2 cells. Naturally, octreotide may or may not reverse the small protective effect of STS on the other cancer lines as observed with NXS2 cells. One problem was the damage to the tail of the mice caused by the injections of cancer cell, chemotherapy drugs, and octreotide. To begin to address this problem mini-pumps for the slow delivery of octreotide (see detailed methods) has been already successfully used. Since 8 injections of octreotide and one of cancer cells plus one for chemotherapy are performed in each cycle, the minipump will reduce injections by 80%, which should allow many cycles of STS/octreotide/etoposide treatment.

Another object is to perform the multiple-injections experiment above with cyclophosphamide, menadione and 5-FU but eventually also with other widely used chemotherapy drugs such as doxorubicin. To begin to understand whether the STS method can be useful for human treatment similar experiments with rats or other model systems will also be performed.

Genetic and Pharmacologic Manipulations of the GH/IGF Axis in Mice and Their Effects on Differential Resistance to Chemotherapy A) One object is to utilize mouse models that have altered GH/IGF axis (including systemic IGF-deficient LID mice, local prostatic IGF-deficient PID mice, and the IGFBP-3 and IGFBP-1 KO mice) to decipher the effects of local versus systemic IGF-1 and of IGFBPs on the host and cancer cells sensitivity to chemotherapy.

B) Another object is to determine the therapeutic index of chemotherapy drugs in these mice models that have been mated into a cancer (myc or TRAMP) background.

C) The third object is to investigate the role of IGFBP-3 and/or inhibitory antibodies against IGF-I either alone or in combination with STS on the resistance of mice and of injected NXS2 neuroblastoma cells to chemotherapy.

It is believed that 1) modulation of systemic (but not local), total or bio-available, IGF-I determines the differential toxicity of various chemotherapeutic agents to mice and cancer cells; 2) higher doses of various chemotherapeutic agents will be tolerated and will prove more effective in mice models of cancer with reduced total or bio-available systemic IGF-I.

In previous studies it was demonstrated that manipulations that decrease the IGF-I signaling in a number of in vitro and in vivo models lead to increased stress resistance in the host (or non-malignant) cells, but did not affect and in some cases increased sensitivity to chemotherapy in the cancer or cancer-like cells. As discussed above, the circulating IGF system is complex and IGF-signaling is controlled by both (endocrine, liver-derived) IGF-I and by locally produced (autocrine/paracrine) IGFs. Furthermore, IGF activity is regulated by a number of IGFBPs, some of which (such as IGFBP-1) are themselves up-regulated by factors such as starvation (inversely to IGF-I which is reduced by starvation and caloric restriction), while others, such as IGFBP-3 are regulated primarily by growth hormone and are down regulated by somatostatin (in the same manner as IGF-I). A series of genetically altered mice with a variety of specific modulations in the GH/IGF system have therefore been derived and/or acquired. These mice include: a) GHRKO mice with reduced growth hormone activity that harbor a GH receptor deletion. These mice are small in size, have low systemic IGF-I and low IGFBP-3 levels, and high IGFBP-1 levels. These mice have previously been shown to have delayed tumor development when mated into the prostate cancer TRAMP model. b) LID (liver IGF-deficient) mice with a targeted deletion of the IGF-I gene in liver obtained. These mice are nearly normal in size, have very low systemic IGF-I levels, low IGFBP-3, and low IGFBP-1. As shown in previous studies, these mice display reduced susceptibility to chemotherapy but do not have a reduced growth of prostate tumors when mated into the TRAMP model. c) PID (prostate IGF-deficient) mice with a prostate epithelial-specific deletion of IGF-I, recently created by mating the prostate-specific probasin-cre transgenic mice with the Igf1-floxed mice. These mice are normal in size and have normal systemic IGF-I, IGFBP-3 and IGFBP-1. Their prostate IGF-I levels are currently being characterized. d) IGFBP3KO mice, which have been recently developed. These mice are 20% larger than controls, have undetectable IGFBP-3 levels, slightly reduced IGF-I, and normal IGFBP-1 levels in serum. e) IGFBP1KO mice. These mice are normal in size, have no IGFBP-1 and normal IGF-I and IGFBP-3. f) TRAMP mice, who develop early and aggressive prostate cancer as a result of prostate specific expression of the SV40 T-antigen. It was recently showed that these mice respond to low fat diets by reducing tumor progression and have elevated IGF-I levels. g) Myc mice, who develop slower growing and less aggressive prostate cancer as a result of prostate-specific over expression of myc. It has been recently observed that these mice have higher levels of IGF-I and also have a more aggressive tumor if fed a high fat diet. h) Myc mice have now been mated into the IGFBP-1 and IGFBP-3 knockout strains to create mice with cancer that lack each of the specific IGFBPs. It is believed that the IGFBP deletion will accelerate the progression of the cancer and therefore chose a slow developing tumor. The TRAMP model has been mated into the LID and PID models with the expectation of delaying the progression of the tumors.

To determine the role systemic versus local IGF-I plays in vivo in chemotherapy resistance, LID mice will be compared to L/L− control mice as shown in previous studies. The PID mice will also be used as an additional control. To determine the role of total versus bio-available IGF-I IGFBP3KO and IGFBP1KO mice will be compared to control mice and treated with chemotherapy inducing stress. To determine the role of IGFBPs as mediators of the DSR effects of starvation and GH-blockade IGFBP3KO and IGFBP1KO mice will be compared to control mice and treated with the 4 chemotherapy drugs as described above.

| In each set of experiments there will be four groups of 20 mice per group mice: |
|---|
| Group 1: WT mice treated with saline injections |
| Group 2: WT mice treated with chemotherapy injections |
| Group 3: Transgenic mice treated with saline injections |
| Group 4: Transgenic mice treated with chemotherapy injections |

As described above, one object is to use 4 groups of mice that will be treated with chemotherapy injections and to look at survival, serum IGF-related parameters and other markers of systemic stress and assess if any of the strains listed above are more or less resistant to chemotherapy. See above methods for details of treatments, which will be similar to those in the immunodeficient mice.

To determine the role combinations and chemotherapy and IGF reduction or blockade in enhancing tumor suppression while improving survival the treatments described above will be repeated on the genetic models described herein. Prostate cancer is the most commonly diagnosed cancer in American men and a major health problem. While localized disease has an excellent chance for cure, metastatic disease leads to androgen-independent progression and death within a few years. Chemotherapy has been used clinically in prostate cancer with limited success (partially due to dose-limiting toxicity). Docetaxel is approved in the US for hormone-refractory prostate cancer and represents an important therapeutic milestone and is the current standard of care for this disease. Cyclophosphamide as well as Etoposide have also been explored in human clinical trials, and while they are not universally recognized as beneficial in daily patient care, they do have effects at high doses. Several prostate cancer bearing mice will be used as models for testing the concept of differential stress resistance in response to chemotherapy. Docetaxel, etoposide, and cyclophoshamide will be tested.

There will be multiple sets of experiments conducted:

| In each set of experiments there will be four groups of 20 mice per group mice: |
|---|
| Group 1: Cancer Bearing WT mice treated with saline injections |
| Group 2: Cancer Bearing WT mice treated with chemotherapy injections |
| Group 3: Cancer Bearing Transgenic mice treated with saline injections |
| Group 4: Cancer Bearing Transgenic mice treated with chemotherapy injections |

In each of the models of prostate cancer bearing transgenic mice the response to chemotherapy (docetaxel, etoposide, and cyclophoshamide) will be compared with the assumption that the combination of genetic ablation of one of the components of the IGF system together with chemotherapy will enhance cancer treatment by protecting the host but not cancer cells. Treatments will be given for 4 weeks at age 12 weeks for TRAMP and 20 weeks for Myc.

Two primary outcome measures are: (1) prostate weight at sacrifice and (2) pathological grade of tumor. Secondary outcome measures will include: (a) TUNEL staining in prostate, (b) Ki67 staining, (c) serum IGF-I and IGFBP-3, (d) quantification of metastasis.

To investigate the role of inhibitory antibodies against IGF-I and/or IGFBP-3 either alone or in combination with STS on the resistance of mice and of injected Nxs2 neuroblastoma cells to etoposide, menadione, 5 FU, and cyclophosphamide (see detailed methods and FIG. 8). These experiments are aimed at testing proteins/drugs with the potential to increase protection against high dose chemotherapy. This is to establish whether IGF-I and IGFBP3 are potential STS mimics. Studies with IGF-I inhibitory antibodies and IGFBP3 have been carried out.

These experiments will be performed essentially as described above (FIGS. 7 and 8, and detailed methods). The IGF-I or IGFBP3 will essentially replace the octreotide/STS treatment.

As shown in previous data it is believed that LID mice and also the GHRKO mice will exhibit increased stress resistance. In addition, it is believed that both the IGFBP-1 and IGFBP-3 knock out mice will have reduced stress resistance. Furthermore, it is believed that IGFBP1KO mice will not show as much benefit from starvation, as the increase in IGFBP-1 expected is part of the IGF-limiting effects of the treatment. It is believed that PID mice will not have differential stress resistance, but they will have an increase in the response to chemo in terms of tumor suppression. An increase in tumor sensitivity to chemotherapy is expected in the LID-TRAMP mice. In the BPKO-Myc models it larger tumors and a poor response to chemo is expected. In general, the treatment with IGF-I antibodies or IGFBP-3 should be consistent with the results obtained with LID and GHRKO mice. Together the object is to establish the complex interface between the GH-IGF system and the resistance of normal and cancer cells to chemotherapy using a series of genetic cancer models with specific IGF-related deletions.

Detailed Methods

Yeast strains and growth conditions: Experiments are carried out in wild type (DBY746 MATa, leu2-3, 112, his3D1, trp1-289, ura3-52, GAL$^+$), and isogenic strains lacking either Sch9 or both Sch9 and Ras2. Wild type (DBY746) and sch9Δ strains expressing hyperactive RAS2$^{val19}$ were constructed by transformation with a centromeric plasmid containing RAS2$^{val19}$ (pRS406-RAS2$^{val19}$, CEN URA3), and over-expressing REV1 or RAD52 were constructed by transforming with multicopy 2μ plasmid carrying REV1 or RAD52 obtained from Open Biosystems. Yeast strains lacking stress response transcription factors (Msn2, Msn4, or Gis1), forkhead transcription factors (Fhl1, Fkh1, Fkh2, or Hcm1), REV1, and RAD52 were generated by one-step gene replacement. Yeast cultures are grown in liquid synthetic dextrose complete medium (SDC) with 2% glucose, supplemented with amino acids, adenine, as well as a four-fold excess of tryptophan, leucine, histidine, uracil. Strains harboring the centromeric plasmid containing RAS2$^{val19}$ were always grown in the absence of uracil to maintain selection.

Yeast viability: Overnight cultures are diluted to OD$_{600}$ 0.1 into SDC medium. After 24 hours (day 1), the appropriate strains will be mixed 1:1 based on OD$_{600}$ and incubated for 2 hours. The mixed cultures will be then treated with either etoposide (300 μM), menadione (200 μM), and 5-FU (150 μM) in medium or water (STS). Etoposide, menadione and 5-FU will be introduced directly into the mixed culture to a final concentration of 0.01%. For treatments in water (STS), mixed cultures will be centrifuged for 5 minutes at 2,500 rpm and the media replaced with either distilled/sterile water or drug-dissolved water. Viability will be measured by quantifying colony-forming units (CFUs) every 24 hours by plating onto appropriate selective media. Viability of individual strains will be measured using the same method as for the mixed cultures.

DSR assays in yeast: Stress resistance against etoposide, 5-FU, and menadione will be measured by spotting serial dilutions of control and treated cells as previously described. Briefly, 24 hours after the initial inoculation (OD=0.1) in SDC medium, cultures will be washed, resuspended and incubated in water for 48 hours with shaking. At day 3, cells will be treated with etoposide, 5-FU, or menadione for 60 min. Serial dilution (up to 1,000-fold) of the treated cultures were spotted onto YPD plates and incubated for 2-3 days at 30° C.

Mutation studies in yeast: Mutation studies in yeast will be performed as previously described. Point mutations, frame shifts and gross chromosomal rearrangements will be measured.

The Role of STS and IGF-1 lowering treatments in protection against chemotherapy in vitro: Cells described in previous studies will be used. Glucose and serum restriction will be done as described before. IGF-I treatment will be performed by incubating cells for 48 hours in DMEM/F12 with 1% FBS and rhIGF-I (100 ng/ml, ProSpec-Tany TechnoGene, Rehovot, Israel), which is shown to be within the IGF-I level range for middle age humans. To antagonize IGF-1 receptor activity, cells will be incubated with the neutralizing monoclonal anti-IGF-1R antibody (1 μg/ml, Calbiochem) in DMEM/F12 1% FBS for 24 hours. To inhibit IGF-1 activity, cells will be treated with IGFBP-3 (200 ng/ml, Abcam) in DMEM/F12, 1% FBS for 24 hours. Following STS/IGF-1 treatments, cells will be incubated with varying concentrations of cyclophosphamide (6-15 mg/ml) for 10 hours, etoposide and 5-fluorouracil (0-120 μM) for 48 hours, and menadione (0-150 μM) for 24 hours in DMEM/F12 with 1% FBS. Cytotoxicity will be measured by the ability to reduce (MTT) as described in previous studies. Apoptosis will be measured by Annexin V binding using the ApopNexin™ apoptosis kit (Upstate) and DNA fragmentation using the TUNEL apoptosis detection kit (Upstate) following manufacturer's instructions.

The effect of STS on IGF-1R signaling in vitro: Cells described in previous studies will be STS pre-treated as described above and Ras and Akt activity will be measured. Cells will be lysed at various time points of STS treatments and lysates will be tested for Ras and Akt activity using the Ras activity assay kit (Upstate) and the Akt western blot assay kit (Calbiochem) following manufacturer's instructions.

The role of IGF-1R signaling in DSR in vitro: Prior to chemotherapeutic drug treatments, cells will be pretreated to inhibit the activity of proteins downstream of IGF-1R including RAS, Akt, ERK, p38 and FOXO3a. To inhibit K, H and N-Ras isoforms, cells will be treated with the farnesyl transferase inhibitor FTI 277 (10 uM) and the geranyl transferase inhibitor GGTI-298 for 48 hours as previously described. To inhibit Akt signaling, cells will be treated with Wortmannin (100 nM) and LY294002 (20 uM) for 1 hour. Erk will be inhibited using 10 μM of ERK inhibitors U0126 or SL327 and also PD98059 and p38 kinases by SB203580 for 2 hours. siRNA will be used to specifically down-regulate the FOXO3a transcription factor. In order to determine the phosphorylation status of p38 and FOXO3a, cells will be lysed following treatment with IGF-I as described. The lysates will be subjected to a Western blot analysis. Anti-phospho-p38 specific (Thr180/Tyr182) antibody and anti-p38 antibody will be used to detect p38 phosphorylation and total p38 respectively (Cell signaling). Anti phospho FOXSO3a (Thr 32) and anti FOXO3a (Ser 253) will be used to detect FOXO phosphorylation. Anti-FOXO3a will be used to detect total FOXO3a (Abcam). Anti-phospho-Akt (Ser 253), anti-phospho-Akt (Thr 308) and anti-Akt will be used to detect phosphorylated and total Akt. FOXO3a over expression will be done using the pcDNA3 plasmid containing a 2,000 bp FOXO3a insert (Invitrogen). 0.2 ug of the plasmid will be used to transfect 80,000 cells using Fugene (Roche) according to manufacturer's protocol. siRNA will be used to specifically silence the FOXO3a transcription factor. Briefly, 80,000 cells will be transfected with 0.2 ug of the pSilencer (Ambion) plasmid that express siRNA oligos targeting FOXO3a using Fugene. All drugs will be from Sigma.

Chemotherapy-induced toxicity measurements in mice: For all the experiments, the animals will be housed in sterile enclosures under specific virus and antigen-free conditions. Procedures will be reviewed and approved by the Institutional Animal Care and Use Committee (IACUC) of University of Southern California and UCLA, and by the licensing or by the ethics committee of the National Research Center, and by the Italian Ministry of Health. Major toxic side effects of chemotherapy such as myelosuppression, gastrointestinal damage, DNA damage, cell death and weight loss will be examined as an indicator of toxicity/morbidity. Also mice will be monitored twice and weighed once daily for any signs of stress or pain and will be euthanized using inhalant isoflurane (1-4%) followed by cervical dislocation if found so. At 60 hours after chemodrug administration, mice will receive a single i.p. injection of BrdU (1 mg in 300 µl of PBS). At 72 hours post-chemotherapy, mice will be deeply anesthetized by a single intraperitoneal injection of 50 mg/kg Nembutal. Following anesthesia, a whole-body perfusion will be performed and blood will be collected via cardiac puncture through the left ventricle and stored in tubes with K3-EDTA for further analysis. Cervical dislocation will be performed to ensure euthanasia and organs will be collected and fixed immediately.

Myelosuppression will be measured by a complete blood cell count with 24 parameters using the HEMAVET® 950 FS hematology analyzer. 24 and 48 hours after chemodrug injection, 20 µl of blood from the tail vein will be collected and also from the heart at the time of sacrifice and stored in K3-EDTA containing tubes and immediately analyzed. Histological examination of bone marrow from pelvic bones and spleen (a site of extra-medullary hematopoiesis in mice) will also be examined for cellularity and content. Gastrointestinal and organ damage will be assessed by looking for areas of ulceration by macroscopic examination and by histological evaluation of the integrity of the mucosa, areas of inflammation, and by measuring the villus to glandular height ratio in the small intestine. Also in pilot experiments, liver, kidney, lung, spleen and heart will be examined for confirmation of organ toxicity by H&E staining focusing on maintenance of architecture, areas of fibrosis. Also organ weight will be recorded. Only one organ most damaged will be selected for each individual drug, and will be examined along with the small intestine in full scale experiments. Organs will be collected after whole-body perfusion with buffered formalin under deep anesthesia with Nembutal. Collected organs will be fixed with 10% formalin for 48 hours and stored in 70% ethanol to be sent to the Norris Cancer Center histology core facility for histological preparations. Specimens will be paraffin embedded and sectioned to 4 µm thickness. DNA damage will be measured by BrdU incorporation as previously described with some modifications. Briefly, 12 hours prior to sacrifice, mice will be i.p. injected with 1 mg BrdU dissolved in 300 µl PBS. 6 mice from each group will be randomly selected and BrdU incorporation will be measured from liver and small intestine tissue samples with antibodies against BrdU following manufacturer's instructions (Abeam). Histological sections of the small intestine and liver will be performed as described above by the Norris Cancer Center histology core facility. Cell death will be determined by measuring blood LDH levels using QuantiChrom™ Lactate Dehydrogenase kit (BioAssay Systems, CA). Procedures will follow manufacturer's protocol.

Short-term starvation-based chemotherapy resistance in mice: Mice from 4 different genetic backgrounds will be tested with 4 different chemodrugs. Mice will be starved (48 hr) as described in previous studies before prior to chemodrug administration. C57BL/6, A/J, athymic Nude, and SCID mice will be tested with cyclophosphamide, etoposide, 5-fluorouracil, and menadione. Pilot experiments will first be conducted to determine the optimum dosage of each drug in each mouse strain. 3 doses will be tested with 6 mice per dose. Once the optimum dosage is known, the procedures will follow as described in preliminary studies with 25 mice per group. The number of mice were determined from previous experience and statistical calculations expecting, with 95% confidence ($\alpha=0.05$, $\beta=0.2$), a 20% difference between the control and experimental groups aided by Statsoft and SigmaStat.

The role of the GH/IGF-1 axis in protection against chemotherapy in mice: Antibodies against the IGF-1 receptor and IGFBP-3 will be employed. This will be tested in at least two mouse strains with 4 drugs mentioned above. Based on previous experience, a single injection of antibodies will be given i.p. 2 days prior to chemodrug administration at 300 µg/kg. As for IGFBP-3, daily i.p. injections with 4 mg/kg/day will be given for 4 days prior to chemotherapy drug administration. 25 mice will be employed per group as calculated above. The groups will be tested with one chemotherapy drug at a time and the pre-treatments will be as follows: Group 1: Control; Group 2: STS; Group 3: IGF-IR antibody; Group 4: IGFBP-3; Group 5: IGF-IR antibody+IGFBP-3; Group 6: STS+IGF-IR antibody+IGFBP-3.

Liver IGF-1 deletion (LID) mice: Due to the limited number of LID mice, 2 drugs will be first tested: 5-fluorouracil and menadione. 1) cyclophosphamide: 18 LL⁻ and 19 LID mice will be given 300 mg/kg CP by a single i.v. injection. 2) Menadione: 11 LL⁻ and 10 LID mice will be given 100 mg/kg menadione by a single i.v. injection.

TRAMP and Myc and PID (prostate cancer models): 3 drugs will first be tested: docetaxal (10 mg/kd per day, single i.p. injection); Etoposide Teva (Teva Pharma B.V., Mijdrecht, Holland) will be injected 80-100 mg/kg; cyclophopshamide (Sigma) will be injected at 300 mg/kg. See below and FIG. 7G for experimental details.

Growth hormone receptor knock-out (GHRKO) mice: 4 heterozygous GHRKO breeding pairs will be received, as homozygous do not breed well. The average litter size is about 6 pups and the average offspring that is a homozygous GHRKO is 12%. Etoposide, cyclophosphamide, 5-fluorouracil and menadione will be tested, and in order to obtain statistically significant results at least 20 mice per group is required as calculated above. Therefore, 8 groups including corresponding control groups (wild type GHR) are required, which translates into 80 GHRKO and 80 control mice. The wild type control group is in the inbred C57BL/6 background.

The mating scheme will be as follows. By mating only heterozygotes, it is estimated to take 72 weeks to obtain the desired number of mice. Mice will be genotyped at the age of 6 weeks with DNA obtained by tail biopsies following Jackson Laboratory protocols. Since GHRKO mice are in the C57BL/6 background, optimum drug dosages would be derived from previous experiments mentioned above.

Starvation-based differential chemotherapy resistance in mice: The following cancer models will be performed: Murine experimental metastatic neuroblastoma model in syngeneic A/J mice: The murine NX3IT28 cell line was generated by hybridization of the GD2-negative C1300 murine neuroblastoma cell line (A/J background) with murine dorsal root ganglional cells from C57BL/6J mice, as previously described. The NXS2 subline was then created by the selection of NX3IT28 cells with high GD2 expression. Six-to-seven-week-old female A/J mice, weighing 15-18 g (Harlan Italy, S. Pietro al Natisone, Italy) will be intravenously inoculated with 200,000 NXS2 cells. Intravenous injection of NXS2 results in experimental metastases to distant organ sites, including liver, kidneys, ovaries, adrenal gland and bone marrow, as previously described (Lode N H et al, JNCI 1997). Murine thoracic neuroblastoma model in syngeneic A/J mice: Six-to-seven-week-old female A/J mice (Harlan Laboratories), weighing 15-18 g, will be injected in the mediastinum, through the skin of the precardial area, with $1\times10^6$ Neuro2a cells, which have the same genetic background than NXS2. Precisely, the needle will penetrate 3 mm and the syringe made an angle of about 120° with respect to the mediastinum. The pericardial area is located between the second and the third rib. Fifteen days after tumor inoculum, numerous subpleural metastases can be detected in the lung and in the draining lymphonodes, as previously described. Human experimental pseudometastatic neuroblastoma model in Nude mice: Six-to-seven-week-old female athymic Nude mice (nu/nu Harlan Laboratories), weighing 18-24 g will be intravenously injected with $3\times10^6$ human neuroblastoma HTLA-230 cell line. This experimental model is characterized by the presence of macrometastases in different organs such as liver, kidneys, ovaries and adrenal glands, and micrometastases in the bone marrow, as previously described. Human orthotopic neuroblastoma model in SCID mice: Six-to-seven-week-old female SCID mice (Harlan Laboratories) will be anesthetized with ketamine (Imalgene 1000, Merial Italia s.p.a, Milan, Italy), subjected to laparotomy and injected with $1.5\times10^6$ HTLA-230, in the capsule of the left adrenal gland, as previously described. Human metastatic breast carcinoma model in SCID mice: Five-to-six-week-old female SCID mice will be anesthetized with ketamine, and injected with $1\times10^6$ MDA-MB-321 human breast carcinoma cells in the mammary fad pad. The implantation of this tumor cell line induces the development of lung and lymph nodes metastases. Human intraperitoneal ovarian carcinoma model in Nude mice: Five-to-six-week-old female athimic Nude mice will be intraperitoneally injected with $1\times10^6$ OVCAR-3 human carcinoma cell line as previously described. In all the models above described, the therapeutic effect of different chemotherapeutic agents including etoposide, cyclophosphamide, 5-fluorouracil (5-FU), and menadione will be tested. All injections will be performed intravenously. Specifically, etoposide Teva (Teva Pharma B.V., Mijdrecht, Holland) will be injected 80-100 mg/kg; cyclophopshamide (Sigma) will be injected at 300 mg/kg; 5-FU will be injected at 150 mg/kg; Menadione will be injected at 50-100 mg/kg. These agents, administered as a single dose or as multiple doses, will be used in combination with short term starvation (STS) and octreotide (OCT). According to the protocol used for previous experiments, the animals will be inoculated with tumor cells, starved for 48 hours and then intravenously treated with the chemotherapeutic agents. Additional daily doses of OCT will be administered for 4 days after chemotherapy. In some experiments, the cycle of STS-chemotherapy-OCT will be repeated after 1 week. Control groups of mice without diet starvation and OCT treatment will be also investigated. For each cancer model, we will perform an experiment that includes 8 groups of animals (10 mice/group), as follows: 1) Control group: 10 mice inoculated with tumor cells on day 1. 2) OCT: 10 mice inoculated with tumor cells on day 1 followed by OCT (1 mg/Kg: daily dose) administration for 4 days from day 4 to day 7. 3) STS: 10 mice inoculated with tumor cells followed by 48 hours-STS from days 1 to day 3. 4) STS/OCT: 10 mice inoculated with tumor cells followed by 48 hours-STS+OCT administration for 4 days. 5) Chemotherapy: 10 mice inoculated with tumor cells, followed by chemotherapy treatment on day 3. 6) Chemotherapy/OCT: 10 mice inoculated with tumor cells followed by chemotherapy treatment/OCT administration for 4 days. 7) STS/Chemotherapy: 10 mice inoculated with tumor cells followed by STS/chemotherapy treatment. 8) STS/Chemotherapy/OCT: 10 mice inoculated with tumor cells followed by STS/chemotherapy treatment/OCT administration for 4 days. In additional experiments, the chemotherapy and OCT injections will be repeated every 2 weeks.

Octreotide delivery using osmotic pumps: Mini-osmotic pumps (Alzet, Model 2004) will be implanted subcutaneously to instill octreotide over a 3 month period. Octreotide will be delivered at 0.25 microl/hr at a concentration of 50 microg/kg/hour. Each mini-pump will deliver for 4 weeks and therefore will be replaced every 4 weeks. Procedures will be performed as described by the manufacturer.

In vivo bioluminescence labeling of cancer cells: In order to study differential resistance to chemotherapy in vivo, A/J mice will be intravenously injected with $2\times10^5$ mouse neuroblastoma NXS2 cell line stably expressing the firefly luciferase gene. Plasmids expressing the firefly luciferase gene were obtained as a SalI/BglII fragment form pGL3-control vector (Promega), and cloned into the XhoI/BamHI sites of the retroviral pLXIN bicistronic vector. Monitoring the growth and death of cancer cells in the animal will be possible by detecting bioluminescence. This is a non-invasive method to monitor the growth and death of cancer cells at multiple stages of the experiment. 25 mice will be employed in each group and 5 mice will be randomly selected for bioluminescence imaging. Toxicity will also be measured as previously described. Bioluminescence will be monitored as previously described. Briefly, mice will be given a single i.p. injection of ketamine (50 mg/kg) and xylazine (10 mg/kg) followed by an i.v. injection of luciferin (50 mg/kg). 4.5 minutes later, when the luciferin is well distributed, mice will be examined with an IVIS 200 optical imaging system (Xenogen Corp.). Signal intensity will be quantified as photon count rate per unit body area per unit solid angle subtended by the detector (units of $photon/s/cm^2/steridian$). 3-dimentional images of bioluminescence will be generated by the single-view diffuse tomography capability of the IVIS 200 and LIVING IMAGE 3D v 2.50. Once injected cancer cells have metastasized, mice will be starved for 48 hours in combination with IGF-1R antibodies or IGFBP-3 as described above prior to chemotherapy. Each drug (cyclophosphamide, etoposide, 5-fluorouracil and menadione) will be tested with 6 pretreatment schedules described above in the role of GH/IGF-1 axis in resistance to chemotherapy experiment.

Toxicity will be measured daily as described above for the first 3 days after chemotherapy, followed by monthly tests for 6 months.

IGF-related hormone levels in mouse serum: Novel mouse assays for the IGF axis have been developed or recently published. ELISA for mouse IGF-I, BP-1, 2, 3 and ALS and GH: Blood will be collected at the time of sacrifice from an intra-cardiac source or the retro-orbital sinus of the mice. Novel IGF-related mouse assays have been recently pioneered. mIGF-I, mIGFBP-3, IGFBP-1, IGFBP-2, and mGH and mALS levels will be run when appropriate. Prostate cancer mice mating: Colonies of Myc and TRAMP mice are currently in-house in UCLA breeding facility. At 4 wk of age, pups will be weaned and sexed and tail snips from all healthy offspring used for genotyping as required. PCR-based genotyping for mIGFBP3, mIGFBP1, mIGF1, Alb-cre and probasin-cre transgenics, and the T-antigen are routinely employed.

Clinical examination: Animals will be observed for mortality/moribundity twice daily during the week and once daily on weekends and holidays. Body weights and clinical observations all animals will be recorded weekly. Clinical observations will be made at 7 wk of age, 1 wk prior to treatment, prior to treatment on d 1, and weekly thereafter.

Preparation and Analysis of Prostate Tissues: At the time of sacrifice, the lower GU tract, including the bladder, testes, seminal vesicles, and prostate, will be removed en bloc. The GU wet weight will be recorded to the nearest 0.01 g. Tissues collected at necropsy will be fixed in 10% (Vol:Vol) phosphate-buffered formalin for 12 h and then transferred to 70% ethanol before standard tissue processing (except for a sample that will be used for RNA). Sections of the prostate (4 mm) will be cut from paraffin-embedded tissues and mounted on ProbeOn-Plus slides (Fisher Scientific). Distant site metastases will be examined at the time of necropsy and dissected if identified.

Assessment of prostate histology and immunohistochemistry: Prostate and metastatic tumor histopathology will be determined by H&E staining, and prostate immunohistochemical analysis of phospho-IGF-IR, phospho-Akt, COX-2, TUNEL will be quantified as described. The techniques for immunostaining and analyzing the stained tissue (percent of cells staining positive, intensity of staining, location of staining) will be used as described.

Image Analysis: Sections will be visualized on a Zeiss-Axiophot DM HT microscope. Images will be captured with an attached camera linked to a computer. Images and figures will be composed by using ADOBE PHOTOSHOP 5.5 (Adobe Systems, Mountain View, Calif.). The initial section will be hematoxylin-and-eosin (H&E)-stained; 10 unstained sections will follow. Subsequently, at 200 μm deeper into the block, another H&E will be followed by 10 unstained sections. Histopathological evaluation using light microscopy will be performed on all H&E-stained slides prepared from the prostate of each animal.

Immunofluorescence analysis and apoptosis detection: Four micrometer-thick sections will be cut from paraffin-embedded tissues. Immunofluorescence will be performed by using M30 CytoDEATH antibody (Boehringer Mannheim) with a fluorescence microscope (Axiophot, Zeiss). Scoring of apoptotic cells in these sections will be done by using the OPTIMAS 6 software program (Optimas, Bothell, Wash.). Apoptotic index (%) will be calculated by dividing the number of apoptotic cells (fluorescence positive) by the total number of cells counted per cross-section of a sample of the prostate. Prostate pathological slides will also be processed by using antibodies for PCNA, and β-actin obtained from Santa Cruz Biotechnology for immunohistochemistry assessment of tumor proliferation.

TUNEL assay: The ApopTag in situ apoptosis detection kit will be purchased from Intergen (New York). In brief, paraffin-embedded tissue sections of tumors will be made from prostates harvested at sacrifice. After de-paraffinization of tissue section, apoptotic DNA fragments will be labeled by terminal deoxynucleotidyl transferase, and detected by anti-digoxigenin antibody that is conjugated to a fluorescein. The samples will be analyzed using a fluorescent microscope, equipped by digital camera and the degree of apoptosis quantitated with Adobe Photoshop 5.5.

Statistical design: The study was designed in conjunction with the biostatistical core of the GCRC at UCLA and SPORE in prostate cancer. The following is an example for most complex studies will be carried out with 4 groups in a 2*2 design: (variable 1:) TRAMP vs LID TRAMP, (variable 2:) Saline vs. IGF-I antibodies infusion. Animals will be randomized: led into the four treatment groups by randomized permutated block design with variable block length. There are two primary endpoints: prostate weight at sacrifice (including tumor) and pathology grade of tumor. At sacrifice secondary endpoints will include serum IGF-1, K-167, TUNEL. Sample size calculation assumptions: (1) The factorial analysis of variance has these effects: genotype and treatment and the interaction between the two. (2) No adjustment for the assessment of effects for a given primary endpoint. (3) The responses of the tumors to the different treatments will be similar in magnitude. (4) The power analysis for each expected or plausible effect size will be 0.85 and the sample size n is estimated using this power for each effect size. (5) From previous data there is evidence of a 30% effect on tumor weight during treatment. (6) Two-way ANOVA, a=0.05, 0.05, 0.15 LID and IGF-I AB effects, and their interaction, respectively. Powers for detecting the treatment effects listed above.

This assumes that the tumor reduction for single treatment is 30%; two treatments is 40%; then the power for detecting each effect is >0.95 (a=0.05), for detecting the interaction of two treatments is 0.86 (a=0.05) if N/group=10. The calculation therefore indicates that N=10/group, 40 total will be the sufficient sample size for each study.

Statistical analysis of data: The primary analysis for each of the two primary endpoints will be analysis of variance for a 2*2-factorial design by estimation of each of the three effects in addition to F or T-tests. Also, correlated analyses between the primary endpoints will be studied in several ways including ANOVA. For longitudinal data, as secondary analysis, mixed-effects models, using the SAS procedure PROC MIXED, and a generalized estimating equations (GEE) approach, using the SAS procedure PROC GENMOD, will be explored to study changes after treatments. In cases where model assumptions such as normality or linearity are violated, non-parametric approaches such as Wilcoxon-Mann-Whitney test, classification and regression tree will be explored to assess the association between outcome variables and treatment exposure and other potential risk factors for the outcomes.

References

1. Holzenberger M, Dupont J, Ducos B, Leneuve P, Geloen A, Even P C, Cervera P, Le Bouc Y. IGF-I receptor regulates lifespan and resistance to oxidative stress in mice. *Nature*. 2003; 421:182-7.

2. Lithgow G J, White T M, Melov S, Johnson T E. Thermotolerance and extended life-span conferred by single-gene mutations and induced by thermal stress. *Proc. Natl. Acad. Sci. USA.* 1995; 92:7540-4.

3. Longo V D, Finch C E. Evolutionary Medicine: from Dwarf Model Systems to Healthy Centenarians. *Science.* 2003; 299:1342-6.

4. Migliaccio E, Giorgio M, Mele S, Pelicci G, Reboldi P, Pandolfi P P, Lanfrancone L, Pelicci P G. The p66shc adaptor protein controls oxidative stress response and life span in mammals. *Nature.* 1999; 402:309-13.

5. Fabrizio P, Pozza F, Pletcher S D, Gendron C M, Longo V T. Regulation of longevity and stress resistance by Sch9 in yeast. *Science.* 2001; 292:288-90.

6. Fabrizio P, Liou L L, Moy V N, Diaspro A, SelverstoneValentine J, Gralla E B, Longo V D. SOD2 Functions Downstream of Sch9 to Extend Longevity in Yeast. *Genetics.* 2003; 163:35-46.

7. Pollak M N, Schernhammer E S, Hankinson S E. Insulin-like growth factors and neoplasia. *Nat Rev Cancer.* 2004; 4:505-18.

8. Harper J M, Salmon A B, Chang Y, Bonkowski M, Bartke A, Miller R A. Stress resistance and aging: influence of genes and nutrition. *Mech Ageing Dev.* 2006; 127:687-94.

9. Longo V D. Mutations in signal transduction proteins increase stress resistance and longevity in yeast, nematodes, fruit flies, and mammalian neuronal cells. *Neurobiol. Aging.* 1999; 20:479-86.

10. Finkel T, Holbrook N J. Oxidants, oxidative stress and the biology of ageing. *Nature.* 2000; 408:239-47.

11. Paradis S, Ailion M, Toker A, Thomas J H, Ruvkun G. A PDK1 homolog is necessary and sufficient to transduce AGE-1 PI3 kinase signals that regulate diapause in *Caenorhabditis elegans. Genes Dev.* 1999; 13:1438-52.

12. Johnson T E. Increased life-span of age-1 mutants in *Caenorhabditis elegans* and lower Gompertz rate of aging. *Science.* 1990; 249:908-12.

13. Fabrizio P, Longo V D. The chronological life span of *Saccharomyces cerevisiae. Aging Cell.* 2003; 2:73-81.

14. Thevelein J M, de Winde J H. Novel sensing mechanisms and targets for the cAMP-protein kinase A pathway in the yeast *Saccharomyces cerevisiae. Mol. Microbiol.* 1999; 33:904-18.

15. Flattery-O'Brien J A, Grant C M, Dawes I W. Stationary-phase regulation of the *Saccharomyces cerevisiae* SOD2 gene is dependent on additive effects of HAP2/3/4/5- and STRE-binding elements. *Mol. Microbiol.* 1997; 23:303-12.

16. Wolff S, Ma H, Burch D, Maciel G A, Hunter T, Dillin A. SMK-1, an essential regulator of DAF-16-mediated longevity. *Cell.* 2006; 124:1039-53.

17. Clancy D J, Gems D, Harshman L G, Oldham S, Stocker H, Hafen E, Leevers S J, Partridge L. Extension of life-span by loss of CHICO, a *Drosophila* insulin receptor substrate protein. *Science.* 2001; 292:104-6.

18. Tatar M, Kopelman A, Epstein D, Tu M P, Yin C M, Garofalo R S. A mutant *Drosophila* insulin receptor homolog that extends life-span and impairs neuroendocrine function. *Science.* 2001; 292:107-10.

19. Lin Y J, Seroude L, Benzer S. Extended life-span and stress resistance in the *Drosophila* mutant Methuselah. *Science.* 1998; 282:943-6.

20. Rogina B, Reenan R A, Nilsen S P, Helfand S L. Extended life-span conferred by cotransporter gene mutations in *Drosophila. Science.* 2000; 290:2137-40.

21. Brown-Borg H M, Borg K E, Meliska C J, Bartke A. Dwarf mice and the ageing process. *Nature.* 1996; 384:33.

22. Coschigano K T, Clemmons D, Bellush L L, Kopchick J J. Assessment of growth parameters and life span of GHR/BP gene-disrupted mice. *Endocrinology.* 2000; 141:2608-13.

23. Brown-Borg H M, Rakoczy S G. Catalase expression in delayed and premature aging mouse models. *Exp Gerontol.* 2000; 35:199-212.

24. Brown-Borg H M, Rakoczy S G, Romanick M A, Kennedy M A. Effects of growth hormone and insulin-like growth factor-I on hepatocyte antioxidative enzymes. *Exp Biol Med.* 2002; 227:94-104.

25. Sharma H S, Nyberg F, Gordh T, Alm P, Westman J. Neurotrophic factors influence upregulation of constitutive isoform of heme oxygenase and cellular stress response in the spinal cord following trauma. An experimental study using immunohistochemistry in the rat. *Amino Acids.* 2000; 19:351-61.

26. Yakar S, Liu J L, Stannard B, Butler A, Accili D, Sauer B, LeRoith D. Normal growth and development in the absence of hepatic insulin-like growth factor I. *Proc Natl Acad Sci USA.* 1999; 96:7324-9.

27. Jones J I, Clemmons D R. Insulin-like growth factors and their binding proteins: biological actions. *Endocr Rev.* 1995; 16:3-34.

28. Flurkey K, Papaconstantinou J, Miller R A, Harrison D E. Lifespan extension and delayed immune and collagen aging in mutant mice with defects in growth hormone production. *Proc Natl Acad Sci USA.* 2001; 98:6736-41.

29. Longo V D. *The Pro-Senescence Role of Ras2 in the Chronological Life Span of Yeast.* Thesis, University of California Los Angeles; 1997:112-153.

30. Yan L, Vatner D E, O'Connor J P, Ivessa A, Ge H, Chen W, Hirotani S, Ishikawa Y, Sadoshima J, Vatner S F. Type 5 adenylyl cyclase disruption increases longevity and protects against stress. *Cell.* 2007; 130:247-58.

31. Kandel E S, Hay N. The regulation and activities of the multifunctional serine/threonine kinase Akt/PKB. *Exp Cell Res.* 1999; 253:210-29.

32. Sohal R S, Weindruch R. Oxidative stress, caloric restriction, and aging. *Science.* 1996; 273:59-63.

33. Sell D R, Lane M A, Johnson W A, Masoro E J, Mock O B, Reiser K M, Fogarty J F, Cutler R G, Ingram D K, Roth G S, Monnier V M. Longevity and the genetic determination of collagen glycoxidation kinetics in mammalian senescence. *Proc. Natl. Acad. Sci. U.S.A.* 1996; 93:485-90.

34. Roth G S, Ingram D K, Joseph J A. Delayed loss of striatal dopamine receptors during aging of dietarily restricted rats. *Brain Res.* 1984; 300:27-32.

35. Finch C E MT. Food restriction and brain aging. *Adv Cell Aging Gerontol.* 1997; 2:279-298.

36. Breese C R, D'Costa A, Rollins Y D, Adams C, Booze R M, Sonntag W E, Leonard S. Expression of insulin-like growth factor-I (IGF-I) and IGF-binding protein 2 (IGF-BP2) in the hippocampus following cytotoxic lesion of the dentate gyrus. *J Comp Neurol.* 1996; 369:388-404.

37. Boden G, Baile C A, McLaughlin C L, Matschinsky F M. Effects of starvation and obesity on somatostatin, insulin, and glucagon release from an isolated perfused organ system. *Am J Physiol.* 1981; 241:E215-20.

38. Tannenbaum G S, Rorstad O, Brazeau P. Effects of prolonged food deprivation on the ultradian growth hormone rhythm and immunoreactive somatostatin tissue levels in the rat. *Endocrinology.* 1979; 104:1733-8.

39. Hartman M L, Veldhuis J D, Johnson M L, Lee M M, Alberti K G, Samojlik E, Thorner M O. Augmented growth hormone (GH) secretory burst frequency and amplitude mediate enhanced GH secretion during a two-day fast in normal men. *J Clin Endocrinol Metab.* 1992; 74:757-65.

40. Zapf J. Physiological role of the insulin-like growth factor binding proteins. *Eur J Endocrinol.* 1995; 132:645-54.

41. Muller E E, Locatelli V, Cocchi D. Neuroendocrine control of growth hormone secretion. *Physiol Rev.* 1999; 79:511-607.

42. Clemmons D R, Van Wyk J J. Factors controlling blood concentration of somatomedin C. *Clin Endocrinol Metab.* 1984; 13:113-43.

43. Hanahan D, Weinberg R A. The hallmarks of cancer. *Cell.* 2000; 100:57-70.

44. Slamon D J, Clark G M, Wong S G, Levin W J, Ullrich A, McGuire W L. Human breast cancer: correlation of relapse and survival with amplification of the HER-2/neu oncogene. *Science.* 1987; 235:177-82.

45. Yarden Y, Ullrich A. Growth factor receptor tyrosine kinases. *Annu Rev Biochem.* 1988; 57:443-78.

46. Lukashev M E, Werb Z. ECM signalling: orchestrating cell behaviour and misbehaviour. *Trends Cell Biol.* 1998; 8:437-41.

47. Medema R H, Bos J L. The role of p21ras in receptor tyrosine kinase signaling. *Crit. Rev Oncog.* 1993; 4:615-61.

48. Kinzler K W, Vogelstein B. Life (and death) in a malignant tumour. *Nature.* 1996; 379:19-20.

49. Downward J. Mechanisms and consequences of activation of protein kinase B/Akt. *Curr Opin Cell Biol.* 1998; 10:262-7.

50. Weinberg R A. The retinoblastoma protein and cell cycle control. *Cell.* 1995; 81:323-30.

51. Cohen P. Clinical implications of the IGF-cancer connection. *Growth Horm IGF Res.* 2001; 11:336-8.

52. Kaplan P J, Mohan S, Cohen P, Foster B A, Greenberg N M. The insulin-like growth factor axis and prostate cancer: lessons from the transgenic adenocarcinoma of mouse prostate (TRAMP) model. *Cancer Res.* 1999; 59:2203-9.

53. Adhami V M, Siddiqui I A, Ahmad N, Gupta S, Mukhtar H. Oral consumption of green tea polyphenols inhibits insulin-like growth factor-1-induced signaling in an autochthonous mouse model of prostate cancer. *Cancer Res.* 2004; 64:8715-22.

54. Vijayababu M R, Arunkumar A, Kanagaraj P, Arunakaran J. Effects of quercetin on insulin-like growth factors (IGFs) and their binding protein-3 (IGFBP-3) secretion and induction of apoptosis in human prostate cancer cells. *J Carcinog.* 2006; 5:10.

55. Shukla S, Mishra A, Fu P, MacLennan G T, Resnick M I, Gupta S. Up-regulation of insulin-like growth factor binding protein-3 by apigenin leads to growth inhibition and apoptosis of 22Rv1 xenograft in athymic nude mice. *Faseb J.* 2005; 19:2042-4.

56. Rajah R, Valentinis B, Cohen P. Insulin-like growth factor (IGF)-binding protein-3 induces apoptosis and mediates the effects of transforming growth factor-beta1 on programmed cell death through a p53- and IGF-independent mechanism. *J Biol. Chem.* 1997; 272:12181-8.

57. Buckbinder L, Talbott R, Velasco-Miguel S, Takenaka I, Faha B, Seizinger B R, Eley N. Induction of the growth inhibitor IGF-binding protein 3 by p53. *Nature.* 1995; 377:646-9.

58. Grimberg A, Liu B, Bannerman P, El-Deiry W S, Cohen P. IGFBP-3 mediates p53-induced apoptosis during serum starvation. *Int J Oncol.* 2002; 21:327-35.

59. Rajah R, Lee K W, Cohen P. Insulin-like growth factor binding protein-3 mediates tumor necrosis factor-alpha-induced apoptosis: role of Bcl-2 phosphorylation. *Cell Growth Differ.* 2002; 13:163-71.

60. Rajah R, Khare A, Lee P D, Cohen P. Insulin-like growth factor-binding protein-3 is partially responsible for high-serum-induced apoptosis in PC-3 prostate cancer cells. *J Endocrinol.* 1999; 163:487-94.

61. Mannhardt B, Weinzimer S A, Wagner M, Fiedler M, Cohen P, Jansen-Durr P, Zwerschke W. Human papillomavirus type 16 E7 oncoprotein binds and inactivates growth-inhibitory insulin-like growth factor binding protein 3. *Mol Cell Biol.* 2000; 20:6483-95.

62. Prieur A, Tirode F, Cohen P, Delattre O. EWS/FLI-1 silencing and gene profiling of Ewing cells reveal downstream oncogenic pathways and a crucial role for repression of insulin-like growth factor binding protein 3. *Mol Cell Biol.* 2004; 24:7275-83.

63. Christoph F, Kempkensteffen C, Weikert S, Krause H, Schostak M, Miller K, Schrader M. Frequent epigenetic inactivation of p53 target genes in seminomatous and nonseminomatous germ cell tumors. *Cancer Lett.* 2007; 247:137-42.

64. Christoph F, Weikert S, Kempkensteffen C, Krause H, Schostak M, Miller K, Schrader M. Regularly methylated novel pro-apoptotic genes associated with recurrence in transitional cell carcinoma of the bladder. *Int J Cancer.* 2006; 119:1396-402.

65. Cohen P. Overview of the IGF-I system. *Horm Res.* 2006; 65 Suppl 1:3-8.

66. Liu B, Lee K W, Anzo M, Zhang B, Zi X, Tao Y, Shiry L, Pollak M, Lin S, Cohen P. Insulin-like growth factor-binding protein-3 inhibition of prostate cancer growth involves suppression of angiogenesis. *Oncogene.* 2007; 26:1811-9.

67. Wu J D, Haugk K, Coleman I, Woodke L, Vessella R, Nelson P, Montgomery R B, Ludwig D L, Plymate S R. Combined in vivo effect of A12, a type 1 insulin-like growth factor receptor antibody, and docetaxel against prostate cancer tumors. *Clin Cancer Res.* 2006; 12:6153-60.

68. Bruce-Keller A J, Umberger G, McFall R, Mattson M P. Food restriction reduces brain damage and improves behavioral outcome following excitotoxic and metabolic insults. *Ann Neurol.* 1999; 45:8-15.

69. Fabrizio P, Gattazzo, C., Battistella, L., Wei M, Chen, C., and Longo, V D. Sir2 Blocks Extreme Life Span Extension. *Cell.* 2005; 123:1-13.

70. Kaeberlein M, Powers R W, 3rd, Steffen K K, Westman E A, Hu D, Dang N, Kerr E O, Kirkland K T, Fields S, Kennedy B K. Regulation of yeast replicative life span by TOR and Sch9 in response to nutrients [see comment]. *Science.* 2005; 310:1193-6.

71. Lin S J, Defossez P A, Guarente L. Requirement of NAD and SIR2 for life-span extension by calorie restriction in *Saccharomyces cerevisiae. Science.* 2000; 289:2126-8.

72. Poole C J, Earl H M, Hiller L, Dunn J A, Bathers S, Grieve R J, Spooner D A, Agrawal R K, Fernando I N, Brunt A M, O'Reilly S M, Crawford S M, Rea D W, Simmonds P, Mansi J L, Stanley A, Harvey P, McAdam K, Foster L, Leonard R C, Twelves C J. Epirubicin and cyclophosphamide, methotrexate, and fluorouracil as adjuvant therapy for early breast cancer. *N Engl J. Med.* 2006; 355:1851-62.

73. Manetta J, Brun J F, Maimoun L, Callis A, Prefaut C, Mercier J. Effect of training on the GH/IGF-I axis during exercise in middle-aged men: relationship to glucose homeostasis. *Am J Physiol Endocrinol Metab.* 2002; 283:E929-36.

74. Grunberg S M. Cyclophosphamide and etoposide for non-small cell and small cell lung cancer. *Drugs.* 1999; 58 Suppl 3:11-5.

75. Mistry A R, Felix C A, Whitmarsh R J, Mason A, Reiter A, Cassinat B, Parry A, Walz C, Wiemels J L, Segal M R, Ades L, Blair I A, Osheroff N, Peniket A J, Lafage-Pochitaloff M, Cross N C, Chomienne C, Solomon E, Fenaux P, Grimwade D. DNA topoisomerase II in therapy-related acute promyelocytic leukemia. *N Engl J. Med.* 2005; 352:1529-38.

76. Vinolas N, Graus F, Mellado B, Caralt L, Estape J. Phase II trial of cisplatinum and etoposide in brain metastases of solid tumors. *J Neurooncol.* 1997; 35:145-8.

77. Kroger N, Hoffknecht M, Hanel M, Kruger W, Zeller W, Stockschlader M, de Wit M, Weh H J, Kabisch H, Erttmann R, Zander A R. Busulfan, cyclophosphamide and etoposide as high-dose conditioning therapy in patients with malignant lymphoma and prior dose-limiting radiation therapy. *Bone Marrow Transplant.* 1998; 21:1171-5.

78. Gronbaek H, Nielsen B, Schrijvers B, Vogel I, Rasch R, Flyvbjerg A. Inhibitory effects of octreotide on renal and glomerular growth in early experimental diabetes in mice. *J Endocrinol.* 2002; 172:637-43.

79. Hunter S J, Shaw J A, Lee K O, Wood P J, Atkinson A B, Bevan J S. Comparison of monthly intramuscular injections of Sandostatin LAR with multiple subcutaneous injections of octreotide in the treatment of acromegaly; effects on growth hormone and other markers of growth hormone secretion. *Clin Endocrinol (Oxf).* 1999; 50:245-51.

80. Maccario M, Aimaretti G, Grottoli S, Gauna C, Tassone F, Corneli G, Rossetto R, Wu Z, Strasburger C J, Ghigo E. Effects of 36-hour fasting on GH/IGF-I axis and metabolic parameters in patients with simple obesity. Comparison with normal subjects and hypopituitary patients with severe GH deficiency. *Int J Obes Relat Metab Disord.* 2001; 25:1233-9.

81. Ngo T H, Barnard R J, Tymchuk C N, Cohen P, Aronson W J. Effect of diet and exercise on serum insulin, IGF-I, and IGFBP-1 levels and growth of LNCaP cells in vitro (United States). *Cancer Causes Control.* 2002; 13:929-35.

82. De Bernardi B, Nicolas B, Boni L, Indolfi P, Carli M, Cordero Di Montezemolo L, Donfrancesco A, Pession A, Provenzi M, di Cataldo A, Rizzo A, Tonini G P, Dallorso S, Conte M, Gambini C, Garaventa A, Bonetti F, Zanazzo A, D'Angelo P, Bruzzi P. Disseminated neuroblastoma in children older than one year at diagnosis: comparable results with three consecutive high-dose protocols adopted by the Italian Co-Operative Group for Neuroblastoma. *J Clin Oncol.* 2003; 21:1592-601.

83. Matthay K K, Villablanca J G, Seeger R C, Stram D O, Harris R E, Ramsay N K, Swift P, Shimada H, Black C T, Brodeur G M, Gerbing R B, Reynolds C P. Treatment of high-risk neuroblastoma with intensive chemotherapy, radiotherapy, autologous bone marrow transplantation, and 13-cis-retinoic acid. Children's Cancer Group. *N Engl J. Med.* 1999; 341:1165-73.

84. Lode H N, Xiang R, Varki N M, Dolman C S, Gillies S D, Reisfeld R A. Targeted interleukin-2 therapy for spontaneous neuroblastoma metastases to bone marrow. *J Natl Cancer Inst.* 1997; 89:1586-94.

85. Susini C, Buscail L. Rationale for the use of somatostatin analogs as antitumor agents. *Ann Oncol.* 2006; 17:1733-42.

86. Zalatnai A, Schally A V. Treatment of N-nitrosobis(2-oxopropyl)amine-induced pancreatic cancer in Syrian golden hamsters with D-Trp-6-LH-RH and somatostatin analogue RC-160 microcapsules. *Cancer Res.* 1989; 49:1810-5.

87. Hejna M, Schmidinger M, Raderer M. The clinical role of somatostatin analogues as antineoplastic agents: much ado about nothing? *Ann Oncol.* 2002; 13:653-68.

88. Lin K, Dorman J B, Rodan A, Kenyon C. daf-16: An HNF-3/forkhead family member that can function to double the life-span of *Caenorhabditis elegans*. *Science.* 1997; 278:1319-22.

89. Kops G J, Dansen T B, Polderman P E, Saarloos I, Wirtz K W, Coffer P J, Huang T T, Bos J L, Medema R H, Burgering B M. Forkhead transcription factor FOXO3a protects quiescent cells from oxidative stress. *Nature.* 2002; 419:316-21.

90. Schindler D, Davies J. Inhibitors of macromolecular synthesis in yeast. *Methods Cell Biol.* 1975; 12:17-38.

91. Brunet A, Sweeney L B, Sturgill J F, Chua K F, Greer P L, Lin Y, Tran H, Ross S E, Mostoslavsky R, Cohen H Y, Hu L S, Cheng H L, Jedrychowski M P, Gygi S P, Sinclair D A, Alt F W, Greenberg M E. Stress-dependent regulation of FOXO transcription factors by the SIRT1 deacetylase. *Science.* 2004; 303:2011-5.

92. Xia Z, Dickens M, Raingeaud J, Davis R J, Greenberg M E. Opposing effects of ERK and JNK-p38 MAP kinases on apoptosis. *Science.* 1995; 270:1326-31.

93. Wang Z, Prins G S, Coschigano K T, Kopchick J J, Green J E, Ray V H, Hedayat S, Christov K T, Unterman T G, Swanson S M. Disruption of growth hormone signaling retards early stages of prostate carcinogenesis in the C3(1)/T antigen mouse. *Endocrinology.* 2005; 146:5188-96.

94. Ellwood-Yen K, Graeber T O, Wongvipat J, Iruela-Arispe M L, Zhang J, Matusik R, Thomas G V, Sawyers C L. Myc-driven murine prostate cancer shares molecular features with human prostate tumors. *Cancer Cell.* 2003; 4:223-38.

95. Hadaschik B A, Gleave M E. Therapeutic options for hormone-refractory prostate cancer in 2007. *Urol Oncol.* 2007; 25:413-9.

96. Al-Chalabi T, Figg W D. Benefits of the combination of thalidomide plus cyclophosphamide in hormone refractory prostate cancer patients. *Cancer Biol Ther.* 2007; 6:318-9.

97. Mackler N J, Pienta K J, Dunn R L, Cooney K A, Redman B G, Olson K B, Fardig J E, Smith D C. Phase II evaluation of oral estramustine, oral etoposide, and intravenous paclitaxel in patients with hormone-sensitive prostate adenocarcinoma. *Clin Genitourin Cancer.* 2007; 5:318-22.

98. Madia F, Gattazzo C, Fabrizio P, Longo V D. A simple model system for age-dependent DNA damage and cancer. *Mech Ageing Dev.* 2007; 128:45-9.

99. Lerner E C, Zhang T T, Knowles D B, Qian Y, Hamilton A D, Sebti S M. Inhibition of the prenylation of K-Ras, but not H- or N-Ras, is highly resistant to CAAX peptidomimetics and requires both a farnesyltransferase and a geranylgeranyl-transferase I inhibitor in human tumor cell lines. *Oncogene.* 1997; 15:1283-8.

100. Alessi D R, Cuenda A, Cohen P, Dudley D T, Saltiel A R. PD 098059 is a specific inhibitor of the activation of mitogen-activated protein kinase kinase in vitro and in vivo. *J Biol. Chem.* 1995; 270:27489-94.

101. Cuenda A, Rouse J, Doza Y N, Meier R, Cohen P, Gallagher T F, Young P R, Lee J C. SB 203580 is a specific inhibitor of a MAP kinase homologue which is stimulated by cellular stresses and interleukin-1. *FEBS Lett.* 1995; 364:229-33.

102. Gallagher E, Enzler T, Matsuzawa A, Anzelon-Mills A, Otero D, Holzer R, Janssen E, Gao M, Karin M. Kinase MEKK1 is required for CD40-dependent activation of the kinases Jnk and p38, germinal center formation, B cell proliferation and antibody production. *Nat. Immunol.* 2007; 8:57-63.

103. Greene L A, Shain W, Chalazonitis A, Breakfield X, Minna J, Coon H G, Nirenberg M. Neuronal properties of hybrid neuroblastoma X sympathetic ganglion cells. *Proc Natl Acad Sci USA.* 1975; 72:4923-7.

104. Corrias M V, Bocca P, Anelli E, Cilli M, Occhino M, Pistoia V, Gambini C. A novel syngeneic murine model for thoracic neuroblastoma obtained by intramediastinal injection of tumor cells. *Cancer Detect Prev.* 2002; 26:468-75.

105. Raffaghello L, Pagnan G, Pastorino F, Cosimo E, Brignole C, Marimpietri D, Montaldo P G, Gambini C, Allen T M, Bogenmann E, Ponzoni M. In vitro and in vivo antitumor activity of liposomal Fenretinide targeted to human neuroblastoma. *Int J Cancer.* 2003; 104:559-67.

106. Pastorino F, Brignole C, Marimpietri D, Sapra P, Moase E H, Allen T M, Ponzoni M. Doxorubicin-loaded Fab' fragments of anti-disialoganglioside immunoliposomes selectively inhibit the growth and dissemination of human neuroblastoma in nude mice. *Cancer Res.* 2003; 63:86-92.

107. Burbridge M F, Kraus-Berthier L, Naze M, Pierre A, Atassi G, Guilbaud N. Biological and pharmacological characterisation of three models of human ovarian carcinoma established in nude mice: use of the CA125 tumour marker to predict antitumour activity. *Int J Oncol.* 1999; 15:1155-62.

108. Liao C P, Zhong C, Saribekyan G, Bading J, Park R, Conti P S, Moats R, Berns A, Shi W, Zhou Z, Nikitin A Y, Roy-Burman P. Mouse models of prostate adenocarcinoma with the capacity to monitor spontaneous carcinogenesis by bioluminescence or fluorescence. *Cancer Res.* 2007; 67:7525-33.

The contents of all references cited herein are incorporated by reference in their entirety.

What is claimed is:

1. A method of contacting a prostate cancer cell with a chemotherapy agent, comprising:
    starving the prostate cancer cell for 24-60 hours to induce differential stress by cultivating the prostate cancer cell in a medium having a glucose level reduced by 25 to 45 percent compared to normal glucose levels for the prostate cancer cell and a reduced IGF-I level compared to normal IGF-I levels for the prostate cancer cell; and
    contacting the prostate cancer cell with the chemotherapy agent.

2. The method of claim 1, further comprising contacting the cancer cell with a cell growth inhibitor of IGFBP-1.

* * * * *